(12) United States Patent
Watanabe et al.

(10) Patent No.: US 8,106,045 B2
(45) Date of Patent: Jan. 31, 2012

(54) 2-MORPHOLINO-4-PYRIMIDONE COMPOUND

(75) Inventors: Kazutoshi Watanabe, Tokyo (JP); Fumiaki Uehara, Tokyo (JP); Shinsuke Hiki, Tokyo (JP); Toshiyuki Kohara, Tokyo (JP); Kenji Fukunaga, Tokyo (JP); Satoshi Yokoshima, Tokyo (JP)

(73) Assignees: Mitsubishi Tanabe Pharma Corporation, Osaka (JP); Sanofi-Aventis, Paris (FR)

( * ) Notice: Subject to any disclaimer, the term of this patent is extended or adjusted under 35 U.S.C. 154(b) by 1155 days.

(21) Appl. No.: 11/573,476

(22) PCT Filed: Sep. 9, 2005

(86) PCT No.: PCT/JP2005/017080
§ 371 (c)(1),
(2), (4) Date: Jul. 16, 2007

(87) PCT Pub. No.: WO2006/028290
PCT Pub. Date: Mar. 16, 2006

(65) Prior Publication Data
US 2009/0124618 A1    May 14, 2009

(30) Foreign Application Priority Data
Sep. 9, 2004    (JP) ................. 2004-296926

(51) Int. Cl.
*A61K 31/535* (2006.01)
*A61K 31/54* (2006.01)
*C07D 413/00* (2006.01)
*C07D 413/14* (2006.01)
(52) U.S. Cl. ............ 514/231.5; 514/233.5; 544/122; 544/224; 544/296
(58) Field of Classification Search ........... 514/231.5, 514/235.5; 544/122, 242, 296
See application file for complete search history.

(56) References Cited

U.S. PATENT DOCUMENTS

| | | | |
|---|---|---|---|
| 7,256,199 B1 | 8/2007 | Watanabe et al. | |
| 7,378,413 B2 * | 5/2008 | Almario Carcia et al. | ... 514/218 |
| 7,427,615 B2 * | 9/2008 | Uehara et al. | ............. 514/229.5 |
| 7,504,411 B2 * | 3/2009 | Watanabe et al. | ............. 514/273 |
| 7,572,793 B2 * | 8/2009 | Uehara et al. | ............. 514/235.8 |
| 2005/0090490 A1 | 4/2005 | Uehara et al. | |
| 2005/0130967 A1 | 6/2005 | Uehara et al. | |
| 2006/0252768 A1 | 11/2006 | Watanabe et al. | |
| 2007/0142409 A1 | 6/2007 | Usui et al. | |

FOREIGN PATENT DOCUMENTS

| | | |
|---|---|---|
| EP | 0616032 | 9/1994 |
| WO | 01/70729 | 9/2001 |
| WO | 03/027080 | 4/2003 |
| WO | 03/037888 | 5/2003 |

OTHER PUBLICATIONS

Extended European Search Report dated Nov. 4, 2010 that issued with respect to European Patent Application No. 10 179 860.
Extended European Search Report dated Nov. 16, 2010 that issued with respect to European Patent Application No. 10 179 893.
G. Glenner et al., Biochemical and Biophysical Research Communications, vol. 120, No. 3, 1984, pp. 885-890.
C.L. Masters et al., The EMBO Journal, vol. 4, No. 11, 1985, pp. 2757-2763.
C.L. Masters et al., Proc. Natl. Acad. Sci. USA, vol. 82, Jun. 1985, pp. 4245-4249.
C.M. Wischik et al., Proc. Natl. Acad. Sci. USA, vol. 85, Jun. 1988, pp. 4506-4510.
J. Kondo et al., Neuron, vol. 1, Nov. 1988, pp. 827-834.
R. Sherrington et al., Nature, vol., 375; Jun. 29, 1995, pp. 754-760.
E. Levy-Lahad et al., Science, vol. 269, Aug. 18, 1995, pp. 973-977.
E.I. Rogaev et al., Nature, vol. 376, Aug. 31, 1995, pp. 775-778.
D.R. Borchelt et al., Neuron, vol. 17, Nov. 1996, pp. 1005-1013.
T. Tomita et al., Proc. Natl. Acad. Sci. USA, vol. 94, Mar. 1997, pp. 2025-2030.
D.W. Dickson et al., Society for Neuroscience Abstracts, vol. 17, 1991, p. 1445. R. Siman et al., The Journal of Neuroscience, vol. 10, No. 7, Jul. 1990, pp. 2400-2411.
Y. Ihara et al., J. Biochem., vol. 99, 1986, pp. 1807-1810.
I. Grundke-Iqbal, et al., Proc. Natl. Acad. Sci. USA, vol. 83, Jul. 1986, pp. 4913-4917.
K. Ishiguro et al., J. Biol. Chem., vol. 267, No. 15, May 25, 1992, pp. 10897-10901.
K. Ishiguro et al., FEBS Lett., vol. 325, Jul. 1993, pp. 167-172.
B.A. Yankner et al., Science, vol. 250, 1990, pp. 279-283.
A. Takashima et al., Proc. Natl. Acad. Sci. USA, vol. 90, Aug. 1993, pp. 7789-7793.

(Continued)

*Primary Examiner* — Sabiha Qazi
(74) *Attorney, Agent, or Firm* — Greenblum & Bernstein, PLC

(57) ABSTRACT

A compound represented by the formula (I), an optically active isomer thereof, or a pharmaceutical acceptable salt thereof: wherein X represents CH or N; represents a $C_1$-$C_{12}$ alkyl; $R^2$ represents a hydrogen atom, or the like; R' represents a $C_1$-$C_6$ alkyl or the like; q represents 0 or an integer of 1 to 7; Y represents a $C_1$-$C_6$ alkyl or the like; p represents 0 or an integer of 1 to 5; R represents a 2,3-dihydroindolyl or the like, which is used for preventive and/or therapeutic treatment of a disease caused by tau protein kinase 1 hyperactivity such as a neurodegenerative diseases (e.g. Alzheimer disease).

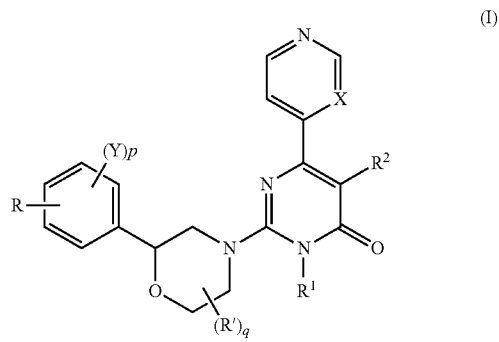

4 Claims, No Drawings

OTHER PUBLICATIONS

U.S. Appl. No. 09/787,426, which is U.S. National Stage of PCT/JP99/05224.
U.S. Appl. No. 10/489,606, which is U.S. National Stage of PCT/JP02/09685.
U.S. Appl. No. 10/489,607, which is U.S. National Stage of PCT/JP02/09684.
U.S. Appl. No. 10/538,766, which is U.S. National Stage of PCT/JP03/15968.
U.S. Appl. No. 10/550,299, which is U.S. National State of PCT/JP04/04320.

* cited by examiner

2-MORPHOLINO-4-PYRIMIDONE COMPOUND

TECHNICAL FIELD

The present invention relates to compounds that are useful as an active ingredient of a medicament for preventive and/or therapeutic treatment of diseases mainly caused by abnormal activity of tau protein kinase 1, such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "Aβ" hereinafter in the specification: Biochem. Biophys. Res. Commun., 120, 885 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of Aβ (Neuron, 17, 1005 (1996); Proc. Natl. Acad. Sci. USA, 94, 2025 (1997)). From these results, it is considered that, in Alzheimer disease, Aβ abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents.

It has been reported that kainic acid treatment that stimulates the AMPA receptor, one of glutamate receptor, increases mRNA of the amyloid precursor protein (abbreviated as "APP" hereinafter in the specification) as a precursor of Aβ (Society for Neuroscience Abstracts, 17, 1445 (1991)), and also promotes metabolism of APP (The Journal of Neuroscience, 10, 2400 (1990)). Therefore, it has been strongly suggested that the accumulation of Aβ is involved in cellular death due to ischemic cerebrovascular disorders. Other diseases in which abnormal accumulation and agglomeration of Aβ are observed include, for example, Down syndrome, cerebral bleeding due to solitary cerebral amyloid angiopathy, Lewy body disease and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like.

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced. As a result, it has been revealed that the primary structure of the rat TPK1 corresponds to that of the enzyme known as rat GSK-3 β (glycogen synthase kinase 3 β, FEBS Lett., 325, 167 (1993)).

It has been reported that Aβ, the main component of senile plaques, is neurotoxic (Science, 250, 279 (1990)). However, various theories have been proposed as for the reason why Aβ causes the cell death, and any authentic theory has not yet been established. Takashima et al. observed that the cell death was caused by Aβ treatment of fetal rat hippocampus primary culture system, and then found that the TPK1 activity was increased by Aβ treatment and the cell death by Aβ was inhibited by antisense of TPK1 (Proc. Natl. Acad. Sci. USA, 90, 7789 (1993); EP616032).

In view of the foregoing, compounds which inhibit the TPK1 activity may possibly suppress the neurotoxicity of Aβ and the formation of PHF and inhibit the nerve cell death in the Alzheimer disease, thereby cease or defer the progress of the disease. The compounds may also be possibly used as a medicament for therapeutic treatment of ischemic cerebrovascular disorder, Down syndrome, cerebral amyloid angiopathy, cerebral bleeding due to Lewy body disease and the like by suppressing the cytotoxicity of Aβ. Furthermore, the compounds may possibly be used as a medicament for therapeutic treatment of neurodegenerative diseases such as progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration and frontotemporal dementia, vascular dementia, traumatic injuries, brain and spinal cord trauma, peripheral neuropathies, retinopathies and glaucoma, as well as other diseases such as non-insulin dependent diabetes, obesity, manic depressive illness, schizophrenia, alopecia, breast cancer, non-small cell lung carcinoma, thyroid cancer, T or B-cell leukemia, and several virus-induced tumors.

As structurally similar compounds to the compounds of the present invention represented by formula (I) described later, the compounds disclosed in the International Publication Nos. WO01/70729, WO03/037888 and WO03/027080 are known. However, these compounds are not enough as medicament in the pharmacokinetics and so on.

DISCLOSURE OF THE INVENTION

An object of the present invention is to provide compounds useful as an active ingredient of a medicament for preventive and/or therapeutic treatment of diseases such as Alzheimer disease. More specifically, the object is to provide novel compounds useful as an active ingredient of a medicament that enables radical prevention and/or treatment of the neurodegenerative diseases such as Alzheimer disease by inhibiting the TPK1 activity to suppress the neurotoxicity of Aβ and the formation of the PHF and by inhibiting the death of nerve cells.

In order to achieve the foregoing object, the inventors of the present invention conducted screenings of various compounds having inhibitory activity against the phosphorylation of TPK1. As a result, they found that compounds represented by the following formula (I) had the desired activity and were useful as an active ingredient of a medicament for preventive and/or therapeutic treatment of the aforementioned diseases. The present invention was achieved on the basis of these findings.

The present invention thus provides;

1. A compound represented by the formula (I), an optically active isomer thereof, or a pharmaceutical acceptable salt thereof;

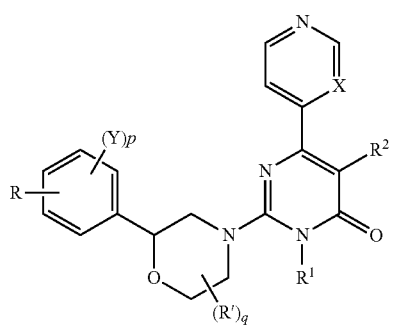

wherein each symbol is as defined below.
X represents CH or N;
$R^1$ represents a $C_1$-$C_{12}$ alkyl which may be substituted;
$R^2$ represents a hydrogen atom, a halogen or a $C_1$-$C_6$ alkyl which may be substituted;
R' represents a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a heterocyclic group which may be substituted,
a $C_1$-$C_6$ alkoxy which may be substituted,
a $C_3$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a hydroxyl,
an oxo group,
a halogen,
a nitro, or
a cyano;
q represents 0 or an integer of 1 to 3;
Y represents a $C_1$-$C_6$ alkyl which may be substituted,
a $C_2$-$C_6$ alkenyl which may be substituted,
a $C_2$-$C_6$ alkynyl which may be substituted,
a $C_3$-$C_7$ cycloalkyl which may be substituted,
a $C_3$-$C_7$ cycloalkenyl which may be substituted,
a $C_1$-$C_6$ alkoxy which may be substituted,
a $C_3$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a halogen,
a nitro,
a cyano,
an amino,
a $C_1$-$C_6$ alkylamino which may be substituted,
a $C_3$-$C_6$ alkenylamino which may be substituted,
a $C_3$-$C_6$ alkynylamino which may be substituted,
a N,N-di-$C_1$-$C_6$ alkylamino which may be substituted,
a N—$C_1$-$C_6$ alkyl-N—$C_3$-$C_6$ alkenylamino which may be substituted,
a N—$C_1$-$C_6$ alkyl-N—$C_3$-$C_6$ alkynylamino which may be substituted,
a N,N-di-$C_3$-$C_6$ alkenylamino which may be substituted,
a N—$C_3$-$C_6$ alkenyl-N—$C_3$-$C_6$ alkynylamino which may be substituted,
or
a N,N-di-$C_3$-$C_6$ alkynylamino which may be substituted,
p represents 0 or an integer of 1 to 4;
R represents
a carboxyl group,
a 2,3-dihydroindolyl,
a perhydroindolyl,
a perhydroisoindolyl,
a perhydroquinolinyl,
a perhydroisoquinolinyl, or
a formula (1) or (2);

In the formula (1), $R^3$ represents a hydrogen atom,
a $C_1$-$C_6$ alkyl which may be substituted,
a $C_3$-$C_6$ alkenyl which may be substituted,
a $C_3$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted, or
a heterocyclic group which may be substituted;
$R^4$ represents an adamantly,
a $C_3$-$C_7$ cycloalkyl which may be substituted,
a C3-C7 cycloalkenyl which may be substituted,
a $C_6$-$C_{10}$ aryl which may be substituted,
a heterocyclic group which may be substituted, or
a formula (3)

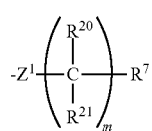

wherein m represents 0 or an integer of 1 to 4,
$Z^1$ represents a carbonyl group, a thiocarbonyl group, or a sulfonyl group, $R^{20}$ and $R^{21}$ are the same or different and each represents a hydrogen atom or a $C_1$-$C_6$ alkyl;

$R^7$ represents a $C_1$-$C_6$ alkyl which may be substituted,
a $C_3$-$C_6$ alkenyl which may be substituted,
a $C_3$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocyclic group which may be substituted,
a $C_1$-$C_6$ alkoxy which may be substituted,
a $C_3$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a heterocycle-oxy which may be substituted, or
a group represented by —NRaRb;
wherein Ra and Rb are the same or different and each represents a hydrogen atom,
a $C_1$-$C_6$ alkyl which may be substituted,
a $C_3$-$C_6$ alkenyl which may be substituted,
a $C_3$-$C_6$ alkynyl which may be substituted,
a $C_3$-$C_7$ cycloalkenyl which may be substituted,
a $C_3$-$C_7$ cycloalkyl which may be substituted,
a $C_6$-$C_{10}$ aryl which may be substituted,
a heterocyclic group which may be substituted,
a $C_1$-$C_6$ alkylcarbonyl which may be substituted,
a $C_2$-$C_6$ alkenylcarbonyl which may be substituted,
a $C_2$-$C_6$ alkynylcarbonyl which may be substituted,
a $C_3$-$C_7$ cycloalkylcarbonyl which may be substituted,
a $C_3$-$C_7$ cycloalkenylcarbonyl which may be substituted,
a $C_6$-$C_{10}$ arylcarbonyl which may be substituted,
a heterocycle-carbonyl which may be substituted,
a $C_1$-$C_6$ alkoxycarbonyl which may be substituted,
a $C_3$-$C_6$ alkenyloxycarbonyl which may be substituted,
a $C_3$-$C_6$ alkynyloxycarbonyl which may be substituted,
a $C_3$-$C_7$ cycloalkyloxycarbonyl which may be substituted,
a $C_3$-$C_7$ cycloalkenyloxycarbonyl which may be substituted,
a $C_6$-$C_{10}$ aryloxycarbonyl which may be substituted,
a $C_1$-$C_6$ alkylsulfonyl which may be substituted,
a $C_2$-$C_6$ alkenylsulfonyl which may be substituted,
a $C_2$-$C_6$ alkynylsulfonyl which may be substituted,
a $C_3$-$C_7$ cycloalkylsulfonyl which may be substituted,
a $C_3$-$C_7$ cycloalkenylsulfonyl which may be substituted,
a $C_6$-$C_{10}$ arylsulfonyl which may be substituted,
a heterocycle-sulfonyl which may be substituted,
an aminocarbonyl,
a $C_1$-$C_6$ alkylaminocarbonyl which may be substituted,
a $C_3$-$C_6$ alkenylaminocarbonyl which may be substituted,
a $C_3$-$C_6$ alkynylaminocarbonyl which may be substituted,
a $C_8$-$C_7$ cycloalkylaminocarbonyl which may be substituted,
a $C_3$-$C_7$ cycloalkenylaminocarbonyl which may be substituted,
a $C_6$-$C_{10}$ arylaminocarbonyl which may be substituted,
a heterocycle-aminocarbonyl which may be substituted,
a N,N-di-$C_1$-$C_6$ alkylaminocarbonyl which may be substituted,
a N—$C_1$-$C_6$ alkyl-N—$C_3$-$C_7$ alkenylaminocarbonyl which may be substituted,
a N—$C_1$-$C_6$ alkyl-N—$C_3$-$C_7$ alkynylaminocarbonyl which may be substituted,
a N—$C_1$-$C_6$ alkyl-N—$C_3$-$C_7$ cycloalkylaminocarbonyl which may be substituted,
a N—$C_1$-$C_6$ alkyl-N—$C_3$-$C_7$ cycloalkenylaminocarbonyl which may be substituted,
a N—$C_1$-$C_6$ alkyl-N—$C_6$-$C_{1-10}$ arylaminocarbonyl which may be substituted,
a N—$C_1$-$C_6$ alkyl-N-heterocycle-aminocarbonyl which may be substituted,
a N,N-di-$C_3$-$C_6$ alkenylaminocarbonyl which may be substituted,
a N—$C_3$-$C_6$ alkenyl-N—$C_3$-$C_6$ alkynylaminocarbonyl which may be substituted,
a N—$C_3$-$C_6$ alkenyl-N—$C_3$-$C_7$ cycloalkylaminocarbonyl which may be substituted,
a N—$C_3$-$C_6$ alkenyl-N—$C_3$-$C_7$ cycloalkenylaminocarbonyl which may be substituted,
a N—$C_3$-$C_6$ alkenyl-N—$C_6$-$C_{10}$ arylaminocarbonyl which may be substituted,
a N—$C_3$-$C_6$ alkenyl-N-heterocycle-aminocarbonyl which may be substituted,
a N,N-di-$C_3$-$C_6$ alkynylaminocarbonyl which may be substituted,
a N—$C_3$-$C_6$ alkynyl-N—$C_3$-$C_7$ cycloalkylaminocarbonyl which may be substituted,
a N—$C_3$-$C_6$ alkynyl-N—$C_3$-$C_7$ cycloalkenylaminocarbonyl which may be substituted,
a N—$C_3$-$C_6$ alkynyl-N—$C_6$-$C_{10}$ arylaminocarbonyl which may be substituted,
a N—$C_3$-$C_6$ alkynyl-N-heterocycle-aminocarbonyl which may be substituted,
a N,N-di-$C_3$-$C_7$ cycloalkylaminocarbonyl which may be substituted,
a N—$C_3$-$C_7$ cycloalkyl-N—$C_3$-$C_7$ cycloalkenylaminocarbonyl which may be substituted,
a N—$C_3$-$C_7$ cycloalkyl-N—$C_6$-$C_{10}$ arylaminocarbonyl which may be substituted,
a N—$C_3$-$C_7$ cycloalkyl-N-heterocycle-aminocarbonyl which may be substituted,
a N,N-di-$C_6$-$C_{14}$ dicycloalkenylaminocarbonyl which may be substituted,
a N—$C_3$-$C_7$ cycloalkenyl-N—$C_6$-$C_{10}$ arylaminocarbonyl which may be substituted,
a N—$C_3$-$C_7$ cycloalkenyl-N-heterocycle-aminocarbonyl which may be substituted,
a N,N-di-$C_6$-$C_{10}$ arylaminocarbonyl which may be substituted, or
a N—$C_6$-$C_{10}$ aryl-N-heterocycle-aminocarbonyl which may be substituted, or
a N,N-di-heterocycle-aminocarbonyl which may be substituted;
or Ra and Rb bind to form a nitrogen containing heterocycle which may contain sulfur atom or oxygen atom together with the adjacent nitrogen atom, or $R^7$ and $R^3$ may bind to form a cycle, and further Ra or Rb may binds $R^3$ to form a cycle together with the adjacent nitrogen atom, or $R^7$ may form a cycle together with Y;

In the formula (2), Z represents a carbonyl group, a sulfonyl group, or a group represented by —O—W— wherein W represents a $C_1$-C6 alkylene group which may be substituted;
$R^5$ and $R^6$ are the same or different and each represents a hydrogen atom,
a $C_1$-$C_6$ alkyl which may be substituted,
a $C_3$-$C_6$ alkenyl which may be substituted,
a $C_3$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted, or
a heterocyclic group which may be substituted;
or $R^3$ and $R^4$, or $R^5$ and $R^6$ may combine with the adjacent nitrogen atom to form a cyclic amino group represented by the formula (4):

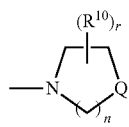
(4)

wherein R¹⁰ represents a $C_1$-$C_6$ alkyl which may be substituted,
a $C_3$-$C_6$ alkenyl which may be substituted,
a $C_3$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocyclic group which may be substituted,
a $C_1$-$C_6$ alkoxy which may be substituted,
a $C_3$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a hydroxyl,
an oxo group,
a halogen,
a nitro, or
a cyano;
r represents 0 or an integer of 1 to n+2;
n represents an integer of 1 to 4;
with the proviso that when n represents 2, then r is not 0;
Q represents a bond, an oxygen atom, sulfur atom or a formula:

wherein $R^{24}$ represents a hydrogen atom,
a $C_1$-$C_6$ alkyl which may be substituted,
a $C_3$-$C_6$ alkenyl which may be substituted,
a $C_3$-$C_6$ alkynyl which may be substituted,
a $C_3$-$C_7$ cycloalkyl which may be substituted,
a $C_3$-$C_7$ cycloalkenyl which may be substituted,
an $C_6$-$C_{10}$ aryl which may be substituted,
a heterocyclic group which may be substituted,
a $C_1$-$C_6$ alkylcarbonyl which may be substituted,
a $C_2$-$C_6$ alkenylcarbonyl which may be substituted,
a $C_2$-$C_6$ alkynylcarbonyl which may be substituted,
a $C_3$-$C_7$ cycloalkylcarbonyl which may be substituted,
a $C_3$-$C_7$ cycloalkenylcarbonyl which may be substituted,
a $C_6$-$C_{10}$ arylcarbonyl which may be substituted,
a heterocycle-carbonyl which may be substituted,
a $C_1$-$C_6$ alkoxycarbonyl which may be substituted,
a $C_3$-$C_6$ alkenyloxycarbonyl which may be substituted,
a $C_3$-$C_6$ alkynyloxycarbonyl which may be substituted,
a $C_3$-$C_7$ cycloalkyloxycarbonyl which may be substituted,
a $C_3$-$C_7$ cycloalkenyloxycarbonyl which may be substituted,
a $C_6$-$C_{10}$ aryloxycarbonyl which may be substituted,
a $C_1$-$C_6$ alkylsulfonyl which may be substituted,
a $C_2$-$C_6$ alkenylsulfonyl which may be substituted,
a $C_2$-$C_6$ alkynylsulfonyl which may be substituted,
a $C_3$-$C_7$ cycloalkylsulfonyl which may be substituted,
a $C_3$-$C_7$ cycloalkenylsulfonyl which may be substituted,
a $C_6$-$C_{10}$ arylsulfonyl which may be substituted,
an aminocarbonyl,
a $C_1$-$C_6$ alkylaminocarbonyl which may be substituted,
a $C_3$-$C_6$ alkenylaminocarbonyl which may be substituted,
a $C_3$-$C_6$ alkynylaminocarbonyl which may be substituted,
a $C_3$-$C_7$ cycloalkylaminocarbonyl which may be substituted,
a $C_3$-$C_7$ cycloalkenylaminocarbonyl which may be substituted,
a $C_6$-$C_{10}$ arylaminocarbonyl which may be substituted,
a heterocycle-aminocarbonyl which may be substituted,
a N,N-di-$C_1$-$C_6$ alkylaminocarbonyl which may be substituted,
a N—$C_1$-$C_6$ alkyl-N—$C_3$-$C_7$ alkenylaminocarbonyl which may be substituted,
a N—$C_1$-$C_6$ alkyl-N—$C_3$-$C_7$ alkynylaminocarbonyl which may be substituted,
a N—$C_1$-$C_6$ alkyl-N—$C_3$-$C_7$ cycloalkylaminocarbonyl which may be substituted,
a N—$C_1$-$C_6$ alkyl-N—$C_3$-$C_7$ cycloalkenylaminocarbonyl which may be substituted,
a N—$C_1$-$C_6$ alkyl-N—$C_6$-$C_{10}$ arylaminocarbonyl which may be substituted,
a N—$C_1$-$C_6$ alkyl-N-heterocycle-aminocarbonyl which may be substituted,
a N,N-di-$C_3$-$C_6$ alkenylaminocarbonyl which may be substituted,
a N—$C_3$-$C_6$ alkenyl-N—$C_3$-$C_6$ alkynylaminocarbonyl which may be substituted,
a N—$C_3$-$C_6$ alkenyl-N—$C_3$-$C_7$ cycloalkylaminocarbonyl which may be substituted,
a N—$C_3$-$C_6$ alkenyl-N—$C_3$-$C_7$ cycloalkenylaminocarbonyl which may be substituted,
a N—$C_3$-$C_6$ alkenyl-N—$C_6$-$C_{10}$ arylaminocarbonyl which may be substituted,
a N—$C_3$-$C_6$ alkenyl-N-heterocycle-aminocarbonyl which may be substituted,
a N,N-di-$C_3$-$C_6$ alkynylaminocarbonyl which may be substituted,
a N—$C_3$-$C_6$ alkynyl-N—$C_3$-$C_7$ cycloalkylaminocarbonyl which may be substituted,
a N—$C_3$-$C_6$ alkynyl-N—$C_3$-$C_7$ cycloalkenylaminocarbonyl which may be substituted,
a N—$C_3$-$C_6$ alkynyl-N—$C_6$-$C_{10}$ arylaminocarbonyl which may be substituted,
a N—$C_3$-$C_6$ alkynyl-N-heterocycle-aminocarbonyl which may be substituted,
a N,N-di-$C_3$-$C_7$ cycloalkylaminocarbonyl which may be substituted,
a N—$C_3$-$C_7$ cycloalkyl-N—$C_3$-$C_7$ cycloalkenylaminocarbonyl which may be substituted,
a N—$C_3$-$C_7$ cycloalkyl-N—$C_6$-$C_{10}$ arylaminocarbonyl which may be substituted,
a N—$C_3$-$C_7$ cycloalkyl-N-heterocycle-aminocarbonyl which may be substituted,
a N,N-di-$C_6$-$C_{14}$ dicycloalkenylaminocarbonyl which may be substituted,
a N—$C_3$-$C_7$ cycloalkenyl-N—$C_6$-$C_{10}$ arylaminocarbonyl which may be substituted,
a N—$C_3$-$C_7$ cycloalkenyl-N-heterocycle-aminocarbonyl which may be substituted,
a N,N-di-$C_6$-$C_{10}$ arylaminocarbonyl which may be substituted,
a N—$C_6$-$C_{10}$ aryl-N-heterocycle-aminocarbonyl which may be substituted, or
a N,N-di-heterocycle-aminocarbonyl which may be substituted;

or Q further represents a formula:

wherein $R^{30}$ and $R^{31}$ are the same or different and each represents a hydrogen atom,
a $C_1$-$C_6$ alkyl which may be substituted,
a $C_3$-$C_6$ alkenyl which may be substituted,
a $C_3$-$C_6$ alkynyl which may be substituted,
a $C_3$-$C_7$ cycloalkyl which may be substituted,
a $C_3$-$C_7$ cycloalkenyl which may be substituted,
a $C_6$-$C_{10}$ aryl which may be substituted,
a heterocyclic group which may be substituted,
a $C_1$-$C_6$ alkyloxycarbonyl which may be substituted,
a $C_3$-$C_6$ alkenyloxycarbonyl which may be substituted,
a $C_3$-$C_6$ alkynyloxycarbonyl which may be substituted,
a $C_3$-$C_7$ cycloalkyloxycarbonyl which may be substituted,
a $C_3$-$C_7$ cycloalkenyloxycarbonyl which may be substituted,
a $C_6$-$C_{10}$ aryloxycarbonyl which may be substituted,
a $C_1$-$C_6$ alkoxy which may be substituted,
a $C_3$-$C_6$ alkenyloxy which may be substituted,
a $C_3$-$C_6$ alkynyloxy which may be substituted,
a $C_3$-$C_7$ cycloalkyloxy which may be substituted,
a $C_3$-$C_7$ cycloalkenyloxy which may be substituted,
a $C_6$-$C_{10}$ aryloxy which may be substituted,
a heterocycl-oxy which may be substituted,
an amino,
a $C_1$-$C_6$ alkylamino which may be substituted,
a $C_3$-$C_6$ alkenylamino which may be substituted,
a $C_3$-$C_6$ alkynylamino which may be substituted,
a $C_3$-$C_7$ cycloalkylamino which may be substituted,
a $C_3$-$C_7$ cycloalkenylamino which may be substituted,
an $C_6$-$C_{10}$ arylamino which may be substituted,
a heterocycle-amino which may be substituted,
a N,N-di-$C_1$-$C_6$ alkylamino which may be substituted,
a N—$C_1$-$C_6$ alkyl-N—$C_3$-$C_6$ alkenylamino which may be substituted,
a N—$C_1$-$C_6$ alkyl-N—$C_3$-$C_6$ alkynylamino which may be substituted,
a N—$C_1$-$C_6$ alkyl-N—$C_3$-$C_7$ cycloalkylamino which may be substituted,
a N—$C_1$-$C_6$ alkyl-N—$C_3$-$C_7$ cycloalkenylamino which may be substituted,
a N—$C_1$-$C_6$ alkyl-N—$C_6$-$C_{10}$ arylamino which may be substituted,
a N—$C_1$-$C_6$ alkyl-N-heterocycle-amino which may be substituted,
a N,N-di-$C_3$-$C_6$ alkenylamino which may be substituted,
a N—$C_3$-$C_6$ alkenyl-N—$C_3$-$C_6$ alkynylamino which may be substituted,
a N—$C_3$-$C_6$ alkenyl-N—$C_3$-$C_7$ cycloalkylamino which may be substituted,
a N—$C_3$-$C_6$ alkenyl-N—$C_3$-$C_7$ cycloalkenylamino which may be substituted,
a N—$C_3$-$C_6$ alkenyl-N—$C_6$-$C_{10}$ arylamino which may be substituted,
a N—$C_3$-$C_6$ alkenyl-N-heterocycle-amino which may be substituted,
a N,N-di-$C_3$-$C_6$ alkynylamino which may be substituted,
a N—$C_3$-$C_6$ alkynyl-N—$C_3$-$C_7$ cycloalkylamino which may be substituted,
a N—$C_3$-$C_6$ alkynyl-N—$C_3$-$C_7$ cycloalkenylamino which may be substituted,
a N—$C_3$-$C_6$ alkynyl-N—$C_6$-$C_{10}$ arylamino which may be substituted,
a N—$C_3$-$C_6$ alkynyl-N-heterocycle-amino which may be substituted,
a N,N-di-$C_3$-$C_7$ cycloalkylamino which may be substituted,
a N—$C_3$-$C_7$ cycloalkyl-N—$C_3$-$C_7$ cycloalkenylamino which may be substituted,
a N—$C_3$-$C_7$ cycloalkyl-N—$C_6$-$C_{10}$ arylamino which may be substituted,
a N—$C_3$-$C_7$ cycloalkyl-N-heterocycle-amino which may be substituted,
a N,N-di-$C_3$-$C_7$ cycloalkenylamino which may be substituted,
a N—$C_3$-$C_7$ cycloalkenyl-N—$C_6$-$C_{10}$ arylamino which may be substituted,
a N—$C_3$-$C_7$ cycloalkenyl-N-heterocycle-amino which may be substituted,
a N,N-di-$C_6$-$C_{10}$ arylamino which may be substituted,
a N—$C_6$-$C_{10}$ aryl-N-heterocycle-amino which may be substituted,
a N.N-diheterocycle-amino which may be substituted,
a $C_1$-$C_6$ alkylcarbonyl which may be substituted,
a $C_2$-$C_6$ alkenylcarbonyl which may be substituted,
a $C_2$-$C_6$ alkynylcarbonyl which may be substituted,
a $C_3$-$C_7$ cycloalkylcarbonyl which may be substituted,
a $C_3$-$C_7$ cycloalkenylcarbonyl which may be substituted,
a $C_6$-$C_{10}$ arylcarbonyl which may be substituted,
a heterocycle-carbonyl which may be substituted,
a $C_1$-$C_6$ alkylsulfonyl which may be substituted,
a $C_2$-$C_6$ alkenylsulfonyl which may be substituted,
a $C_2$-$C_6$ alkynylsulfonyl which may be substituted,
a $C_3$-$C_7$ cycloalkylsulfonyl which may be substituted,
a $C_3$-$C_7$ cycloalkenylsulfonyl which may be substituted
a $C_6$-$C_{10}$ arylsulfonyl which may be substituted,
an aminocarbonyl,
a $C_1$-$C_6$ alkylaminocarbonyl which may be substituted,
a $C_3$-$C_6$ alkenylaminocarbonyl which may be substituted,
a $C_3$-$C_6$ alkynylaminocarbonyl which may be substituted,
a $C_3$-$C_7$ cycloalkylaminocarbonyl which may be substituted,
a $C_3$-$C_7$ cycloalkenylaminocarbonyl which may be substituted,
a $C_6$-$C_{10}$ arylaminocarbonyl which may be substituted,
a heterocycle-aminocarbonyl which may be substituted,
a N,N-di-$C_1$-$C_6$ alkylaminocarbonyl which may be substituted,
a N—$C_1$-$C_6$ alkyl-N—$C_3$-$C_7$ alkenylaminocarbonyl which may be substituted,
a N—$C_1$-$C_6$ alkyl-N—$C_3$-$C_7$ alkynylaminocarbonyl which may be substituted,
a N—$C_1$-$C_6$ alkyl-N—$C_3$-$C_7$ cycloalkylaminocarbonyl which may be substituted,
a N—$C_1$-$C_6$ alkyl-N—$C_3$-$C_7$ cycloalkenylaminocarbonyl which may be substituted,
a N—$C_1$-$C_6$ alkyl-N—$C_6$-$C_{10}$ arylaminocarbonyl which may be substituted,
a N—$C_1$-$C_6$ alkyl-N-heterocycle-aminocarbonyl which may be substituted,
a N,N-di-$C_3$-$C_6$ alkenylaminocarbonyl which may be substituted,
a N—$C_3$-$C_6$ alkenyl-N—$C_3$-$C_6$ alkynylaminocarbonyl which may be substituted,
a N—$C_3$-$C_6$ alkenyl-N—$C_3$-$C_7$ cycloalkylaminocarbonyl which may be substituted,
a N—$C_3$-$C_6$ alkenyl-N—$C_3$-$C_7$ cycloalkenylaminocarbonyl which may be substituted,
a N—$C_3$-$C_6$ alkenyl-N—$C_6$-$C_{10}$ arylaminocarbonyl which may be substituted, a N—C$_3$-C$_6$ alkenyl-N-heterocycle-aminocarbonyl which may be substituted, a N,N-di-C$_3$-C$_6$ alkynylaminocarbonyl which may be substituted, a N—C$_3$-C$_6$ alkynyl-N—C$_3$-C$_7$ cycloalkylaminocarbonyl which may be substituted, a N—C$_3$-C$_6$ alkynyl-N—C$_3$-C$_7$ cycloalkenylaminocarbonyl which may be substituted, a N—C$_3$-C$_6$ alkynyl-N—C$_6$-C$_{10}$ arylaminocarbonyl which may be substituted, a N—C$_3$-C$_6$ alkynyl-N-heterocycle-aminocarbonyl which may be substituted, a N,N-di-C$_3$-C$_7$ cycloalkylaminocarbonyl which may be substituted, a N—C$_3$-C$_7$ cycloalkyl-N—C$_3$-C$_7$ cycloalkenylaminocarbonyl which may be substituted, a N—C$_3$-C$_7$ cycloalkyl-N—C$_6$-C$_{10}$ arylaminocarbonyl which may be substituted, a N—C$_3$-C$_7$ cycloalkyl-N-heterocycle-aminocarbonyl which may be substituted, a N,N-di-C$_6$-C$_{14}$ dicycloalkenylaminocarbonyl which may be substituted, a N—C$_3$-C$_7$ cycloalkenyl-N—C$_6$-C$_{10}$ arylaminocarbonyl which may be substituted, a N—C$_3$-C$_7$ cycloalkenyl-N-heterocycle-aminocarbonyl which may be substituted, a N,N-di-C$_6$-C$_{10}$ arylaminocarbonyl which may be substituted, a N—C$_6$-C$_{10}$ aryl-N-heterocycle-aminocarbonyl which may be substituted, or a N,N-di-heterocycle-aminocarbonyl which may be substituted.

2. The compound, an optically active isomer thereof, or a pharmaceutical acceptable salt thereof according to the above 1, wherein R$^2$ is a hydrogen atom or a halogen.

3. The compound, an optically active isomer thereof, or a pharmaceutical acceptable salt thereof according to the above 1, wherein R$^2$ is a hydrogen atom.

4. The compound, an optically active isomer thereof, or a pharmaceutical acceptable salt thereof according to the above 1, wherein R$^1$ is methyl group.

5. The compound, an optically active isomer thereof, or a pharmaceutical acceptable salt thereof according to the above 1, wherein q is 0.

6. The compound, an optically active isomer thereof, or a pharmaceutical acceptable salt thereof according to the above 1, wherein Y is a C$_1$-C$_6$ alkyl which may be substituted, a C$_1$-C$_6$ alkoxy which may be substituted, a halogen, a nitro, a cyano, an amino, a C$_1$-C$_6$ alkylamino which may be substituted or a N,N-di-C$_1$-C$_6$ alkylamino which may be substituted.

7. The compound, an optically active isomer thereof, or a pharmaceutical acceptable salt thereof according to the above 1, wherein R represents a formula (1).

8. The compound, an optically active isomer thereof, or a pharmaceutical acceptable salt thereof according to the above 1, wherein R represents a formula (2).

9. The compound, an optically active isomer thereof, or a pharmaceutical acceptable salt thereof according to the above 7, wherein R$^4$ represents a formula (3).

10. The compound, an optically active isomer thereof, or a pharmaceutical acceptable salt thereof according to the above 1, wherein R$^1$ is methyl group, R$^2$ is hydrogen atom, and p is 0.

11. A compound according to claim 1 selected from the group consisting of:

2-(2-(4-((4-Pyrrolidin-1-yl)piperidin-1-yl)phenyl)morpholin-4-yl)-3-methyl-6-pyrimidin-4-yl-3H-pyrimidin-4-one, 2-(2-(4-((4-Piperidin-1-yl)piperidin-1-yl)phenyl)morpholin-4-yl)-3-methyl-6-pyrimidin-4-yl-3H-pyrimidin-4-one, 2-(2-(4-(N-Cyclohexyl-N-methylamino)phenyl)morpholin-4-yl)-3-methyl-6-pyridin-4-yl-3H-pyrimidin-4-one, 2-(2-(4-(4-(2-Hydroxyethyl)piperazin-1-yl)phenyl)morpholin-4-yl)-3-methyl-6-pyridin-4-yl-3H-pyrimidin-4-one, 2-(2-(4-((3-Pyrrolidin-1-yl)pyrrolidin-1-yl)phenyl)morpholin-4-yl)-3-methyl-6-pyrimidin-4-yl-3H-pyrimidin-4-one, 2-(2-(4-(3-N-acetyl-N-methylaminopyrrolidin-1-yl)phenyl)morpholin-4-yl)-3-methyl-6-pyridin-4-yl-3H-pyrimidin-4-one, 2-{2-[4-(3-Hydroxy-azetidin-1-yl)phenyl]morpholin-4-yl}-3-methyl-6-pyridin-4-yl-3H-pyrimidin-4-one, N-(4-(4-(1-Methyl-6-oxo-4-(pyridin-4-yl)-1,6-dihydropyrimidin-2-yl)morpholin-2-yl)-phenyl)-acetamide, N-(4-(4-(1,6-Dihydro-1-methyl-6-oxo-4,4'-bipyrimidin-2-yl)morpholin-2-yl)phenyl)-acetamide, 2-(2-(4-(2-Pyridylamino)phenyl)morpholin-4-yl)-3-methyl-6-pyrimidin-4-yl-3H-pyrimidin-4-one, 2-(2-(4-Cyclopropylcarbonylamino)phenyl)morpholin-4-yl)-3-methyl-6-pyridin-4-yl-3H-pyrimidin-4-one, 2-(2-(4-Cyclopropylcarbonylamino)phenyl)morpholin-4-yl)-3-methyl-6-pyrimidin-4-yl-3H-pyrimidin-4-one, 2-(2-(4-Tetrahydrofuran-3-ylamino)phenyl)morpholin-4-yl)-3-methyl-6-pyrimidin-4-yl-3H-pyrimidin-4-one, 2-(2-(4-(N-Tetrahydrofuran-3-yl-N-methylamino)phenyl)morpholin-4-yl)-3-methyl-6-pyrimidin-4-yl-3H-pyrimidin-4-one, N-{4-[(2S)-4-(1-Methyl-6-oxo-4-pyridin-4-yl-1,6-dihydropyrimidin-2-yl)morpholin-2-yl]phenyl}-2-pyrrolidin-1-ylacetamide, N-{4-[(2S)-4-(1-Methyl-6-oxo-1,6-dihydro-4,4'-bipyrimidin-2-yl)morpholin-2-yl]phenyl}-2-pyrrolidin-1-ylacetamide, N2,N2-Dimethyl-N1-{4-[(2S)-4-(1-methyl-6-oxo-1,6-dihydro-4,4'-bipyrimidin-2-yl-morpholin-2-yl]phenyl}glycinamide, Methyl{4-[(2S)-4-(1-methyl-6-oxo-4-pyridin-4-yl-1,6-dihydropyrimidin-2-yl)morpholin-2-yl]phenyl}carbamate, Ethyl{4-[(2S)-4-(1-methyl-6-oxo-1,6-dihydro-4,4'-bipyrimidin-2-yl)morpholin-2-yl)-phenyl}carbamate, N-{4-Methoxy-3-[(2S)-4-(1-methyl-6-oxo-4-pyridin-4-yl-1,6-dihydropyrimidin-2-yl)-morpholin-2-yl]phenyl}acetamide, N-{4-Methoxy-3-[(2S)-4-(1-methyl-6-oxo-1,6-dihydro-4,4'-bipyrimidin-2-yl)morpholin-2-yl]phenyl}acetamide, and N-{3-[(2S)-4-(1-Methyl-6-oxo-4-pyridin-4-yl-1,6-dihydropyrimidin-2-yl)morpholin-2-yl]phenyl}acetamide, an optically active isomer thereof, or a pharmaceutically acceptable salt thereof.

12. A medicament comprising as an active ingredient a substance selected from the group consisting of the compound represented by the formula (I) and an optically active isomer thereof, or a pharmaceutically acceptable salt thereof according to the above 1.

13. A tau protein kinase 1 inhibitor selected from the group consisting of the compound represented by the formula (I) and an optically active isomer thereof, or a pharmaceutically acceptable salt thereof according to the above 1.

14. The medicament according to the above 12 which is used for preventive and/or therapeutic treatment of a disease caused by tau protein kinase 1 hyperactivity.

15. The medicament according to the above 12 which is used for preventive and/or therapeutic treatment of a neurodegenerative disease.

16. The medicament according to the above 15, wherein the disease is selected from the group consisting of Alzheimer disease, ischemic cerebrovascular accidents, Down syndrome, cerebral bleeding due to cerebral amyloid angiopathy, progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration, frontotemporal dementia, vascular dementia, traumatic injuries, brain and spinal cord trauma, peripheral neuropathies, retinopathies and glaucoma.

17. The medicament according to the above 12, which is used for preventive and/or therapeutic treatment of a disease selected from the group consisting of non-insulin dependent diabetes, obesity, manic depressive illness, schizophrenia, alopecia, breast cancer, non-small cell lung carcinoma, thyroid cancer, T or B-cell leukemia, and a virus-induced tumor.

MODE FOR CARRYING OUT THE INVENTION

Unless otherwise indicated, the following definitions are set forth to illustrate and defined the meaning and scope of the various terms used to describe the invention herein.

The term "$C_1$-$C_6$ alkyl" means alkyl group having 1 to 6 carbon atoms which may be either linear or branched, for example, methyl, ethyl, n-propyl, isopropyl, n-butyl, isobutyl, sec-butyl, tert-butyl, n-pentyl, isopentyl, neopentyl, 1,1-dimethylpropyl, n-hexyl, isohexyl.

The term "$C_1$-$C_{12}$ alkyl" means alkyl group having 1 to 12 carbon atoms which may be either linear or branched, for example, methyl, ethyl, n-propyl, isopropyl, n-butyl, isobutyl, sec-butyl, tert-butyl, n-pentyl, isopentyl, neopentyl, 1,1-dimethylpropyl, n-hexyl, isohexyl, heptyl, octyl, nonyl, decyl, undecyl or dodecyl.

The term "$C_3$-$C_7$ cycloalkyl" means cycloalkyl having 3 to 7 atoms, for example, cyclopropyl, cyclobutyl, cyclopentyl, cyclohexyl, cycloheptyl.

The term "$C_6$-$C_{10}$ aryl" means a group having 6 to 10 carbon atoms derived from, for example, benzene, naphthalene, indane, indene, tetrahydronaphthalene. The bond position in the cycle is not limited.

The term "heterocyclic group" and "heterocycle" mean cyclic group derived from, for example, furan, dihydrofuran, tetrahydrofuran, pyran, dihydropyran, tetrahydropyran, benzofuran, dihydrobenzofuran, isobenzofuran, chromene, chroman, isochroman, thiophene, benzothiophene, pyrrole, pyrroline, pyrrolidine, imidazole, imidazoline, imidazolidine, pyrazole, pyrazoline, pyrazolidine, triazole, tetrazole, pyridine, pyridine oxide, piperidine, pyrazine, piperazine, pyrimidine, pyridazine, indole, indoline, isoindole, isoindoline, indazole, benzimidazole, benzotriazole, tetrahydroisoquinoline, benzothiazolinone, benzoxazolinone, purine, quinolizine, quinoline, phthalazine, naphthyridine, quinoxaline, quinazoline, cinnoline, pteridine, oxazole, oxazolidine, isoxazole, isoxazolidine, oxadiazole, thiazole, benzothiazole, thiazylidine, isothiazole, isothiazolidine, benzodioxole, dioxane, benzodioxane, dithian, morpholine, thiomorpholine, phthalimide homopiperidinyl, homopiperazinyl. The bond position in the cycle is not limited.

The term "$C_1$-$C_6$ alkoxy" means alkoxy group having 1 to 6 carbon atoms which may be either linear or branched, for example, methoxy, ethoxy, n-propoxy, isopropoxy, n-butoxy, isobutoxy, sec-butoxy, tert-butoxy, n-pentyloxy isopentyloxy, neopentyloxy, 1,1-dimethylpropoxy, n-hexyloxy, isohexyloxy.

The term "$C_2$-$C_6$ alkenyl" means alkenyl group having 2 to 6 carbon atoms, for example, vinyl, propenyl, buteny,1, pentenyl, hexenyl.

The term "$C_2$-$C_6$ alkynyl" means alkynyl group having 2 to 6 carbon atoms, for example, ethynyl, propynl, butynyl, pentynyl, hexynyl.

The term "$C_3$-$C_7$ cycloalkenyl" means cycloalkenyl group having 3 to 7 carbon atoms, for example, cyclopropenyl cyclobutenyl, cyclopentenyl, cyclohexenyl, cycloheptenyl.

The term "nitrogen containing heterocycle formed by Ra and Rb together with the adjacent nitrogen atom" means, for example, pyrrolidinyl which may be substituted, piperidinyl which may be substituted, morpholino which may be substituted, thiomorpholino which may be substituted, piperazinyl which may be substituted, homopiperazinyl which may be substituted.

The term "which may be substituted" means a group which may have one or more substituents. The substituent in the present specification means, for example, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_6$-$C_{10}$ aryl, heterocycles, $C_1$-$C_6$ alkoxy, $C_3$-$C_6$ alkenyloxy, $C_3$-$C_6$ alkynyloxy, $C_3$-$C_7$ cycloalkyloxy, $C_3$-$C_7$ cycloalkenyloxy, $C_6$-$C_{10}$ aryloxy, heterocycleoxy, halogen (chlorine, bromine, fluorine, iodine), nitro, amino, cyano, hydroxyl, oxo, $C_1$-$C_6$ alkylcarbonyl, $C_2$-$C_6$ alkenylcarbonyl, $C_2$-$C_6$ alkynylcarbonyl, $C_3$-$C_7$ cycloalkylcarbonyl, $C_3$-$C_7$ cycloalkenylcarbonyl, $C_6$-$C_{10}$ arylcarbonyl, heterocyclecarbonyl, $C_1$-$C_6$ alkylsulfonyl, $C_2$-$C_6$ alkenylsulfonyl, $C_2$-$C_6$ alkynylsulfonyl, $C_3$-$C_7$ cycloalkylsulfonyl, $C_3$-$C_7$ cycloalkenylsulfonyl, $C_6$-$C_{10}$ arylsulfonyl, heterocyclesulfonyl, $C_1$-$C_6$ alkoxycarbonyl, $C_3$-$C_6$ alkenyloxycarbonyl, $C_3$-$C_6$ alkynyloxycarbonyl, $C_3$-$C_7$ cycloalkyloxycarbonyl, $C_3$-$C_7$ cycloalkenyloxycarbonyl, $C_6$-$C_{10}$ aryloxycarbonyl, heterocycleoxycarbonyl, amino, $C_1$-$C_6$ alkylamino, $C_3$-$C_6$ alkenylamino, $C_3$-$C_6$ alkynylamino, $C_3$-$C_7$ cycloalkylamino, $C_3$-$C_7$ cycloalkenylamino, $C_6$-$C_{10}$ arylamino, heterocycle-amino, N,N-di-$C_1$-$C_6$ alkylamino, aminocarbonyl, $C_1$-$C_6$ alkylaminocarbonyl, $C_3$-$C_6$ alkenylaminocarbonyl, $C_3$-$C_6$ alkynylaminocarbonyl, $C_3$-$C_7$ cycloalkylaminocarbonyl, $C_3$-$C_7$ cycloalkenylaminocarbonyl, $C_6$-$C_{10}$ arylaminocarbonyl, heterocycle-aminocarbonyl, N,N-di-$C_1$-$C_6$ dialkylaminocarbonyl. The number of substituents as well as their types and substituting positions are not particularly limited, and when two or more substituents are present, they may be the same or different. In the above substituents, every term expressed by "$C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_6$-$C_{10}$ aryl, heterocycle or $C_1$-$C_6$ alkoxy" represents the same meaning as defined in the above. These substituents may be also substituted by the substituents described above.

$R^1$ may preferably be a $C_1$-$C_3$ alkyl group, more preferably be a methyl group.

$R^2$ may preferably be a hydrogen atom.

p may preferably be 0.

R may preferably be the group of formula (1).

The pharmaceutically acceptable salt of the compound represented by the aforementioned formula (I) may include the salt with inorganic acid such as hydrochloric acid, hydrobromic acid and the like and the salt with organic acid such as acetic acid, propionic acid, tartaric acid, fumaric acid, maleic acid, malic acid, oxalic acid, succinic acid, citric acid, benzoic acid and the like.

In addition to the compound represented by the aforementioned formula (I), an optically active isomer thereof, or a pharmaceutically acceptable salt thereof, their solvates and hydrates also fall within the scope of the present invention. The compound represented by the formula (I) may have one or more asymmetric carbon atoms. As for the stereochemistry of such asymmetric carbon atoms, they may independently be in either (R) and (S) configuration, and the pyrimidone derivative may exist as stereoisomers such as optical isomers, or diastereoisomers. Any stereoisomers of pure form, any mixtures of stereoisomers, racemates and the like fall within the scope of the present invention Examples of preferred compounds of the present invention are shown in the tables set out below. However, the scope of the present invention is not limited by the following compounds.

TABLE 1

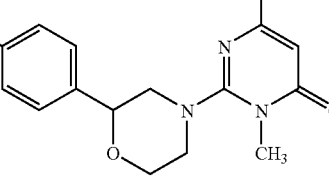

| Compound No. | $\begin{array}{c} R^3 \\ \diagdown N{-} \\ \diagup \\ R^4 \end{array}$ | X |
|---|---|---|
| 1 | 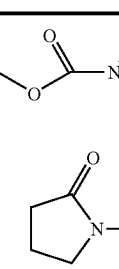 | N |
| 2 | 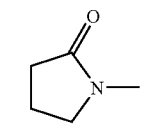 | CH |
| 3 | 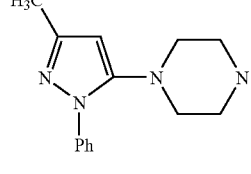 | N |
| 4 | 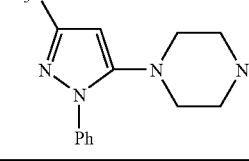 | N |
| 5 | 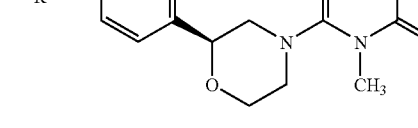 | CH |

TABLE 2

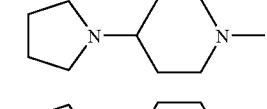

| Compound No. | $\begin{array}{c} R^3 \\ \diagdown N{-} \\ \diagup \\ R^4 \end{array}$ | X |
|---|---|---|
| 6 |  | CH |
| 7 |  | N |
| 8 | 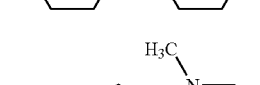 | CH |
| 9 | 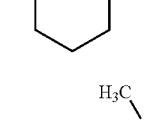 | N |
| 10 | 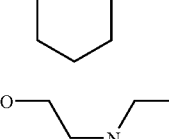 | CH |
| 11 | 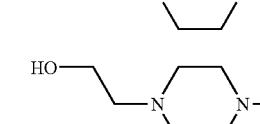 | N |
| 12 | 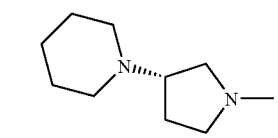 | CH |
| 13 | 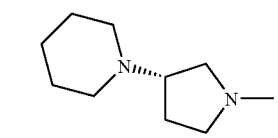 | N |
| 14 | 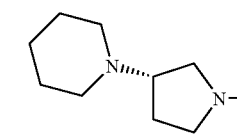 | N |
| 15 |  | CH |

TABLE 2-continued
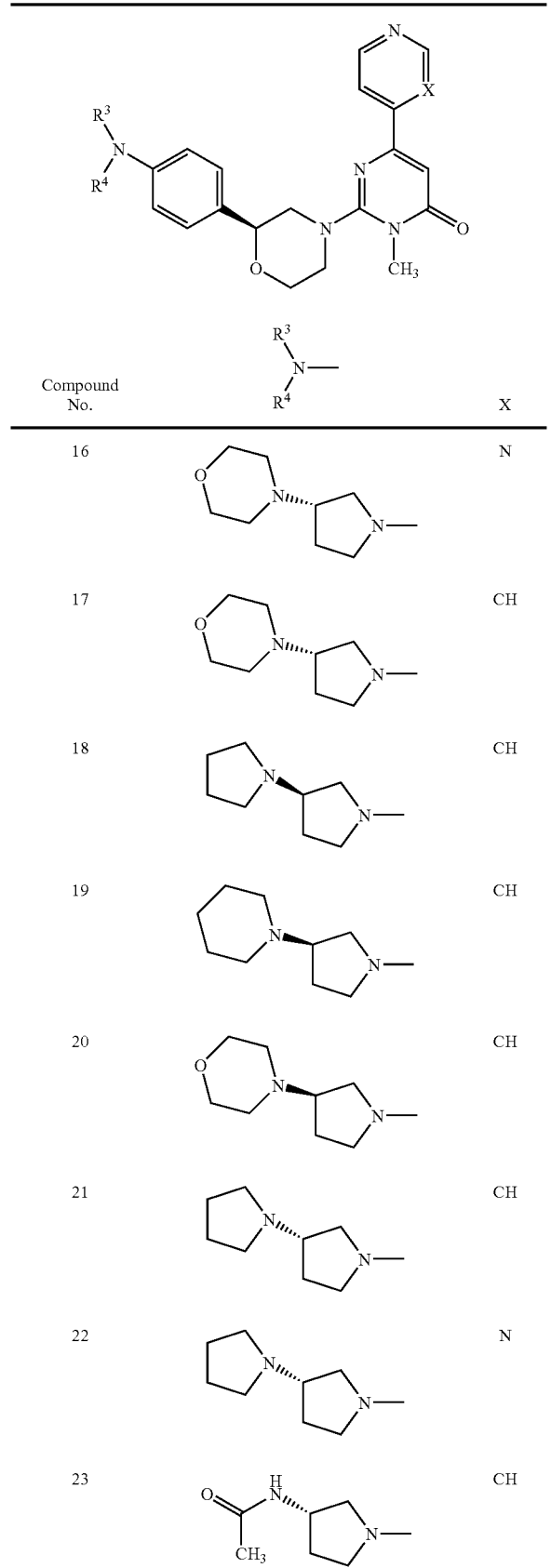
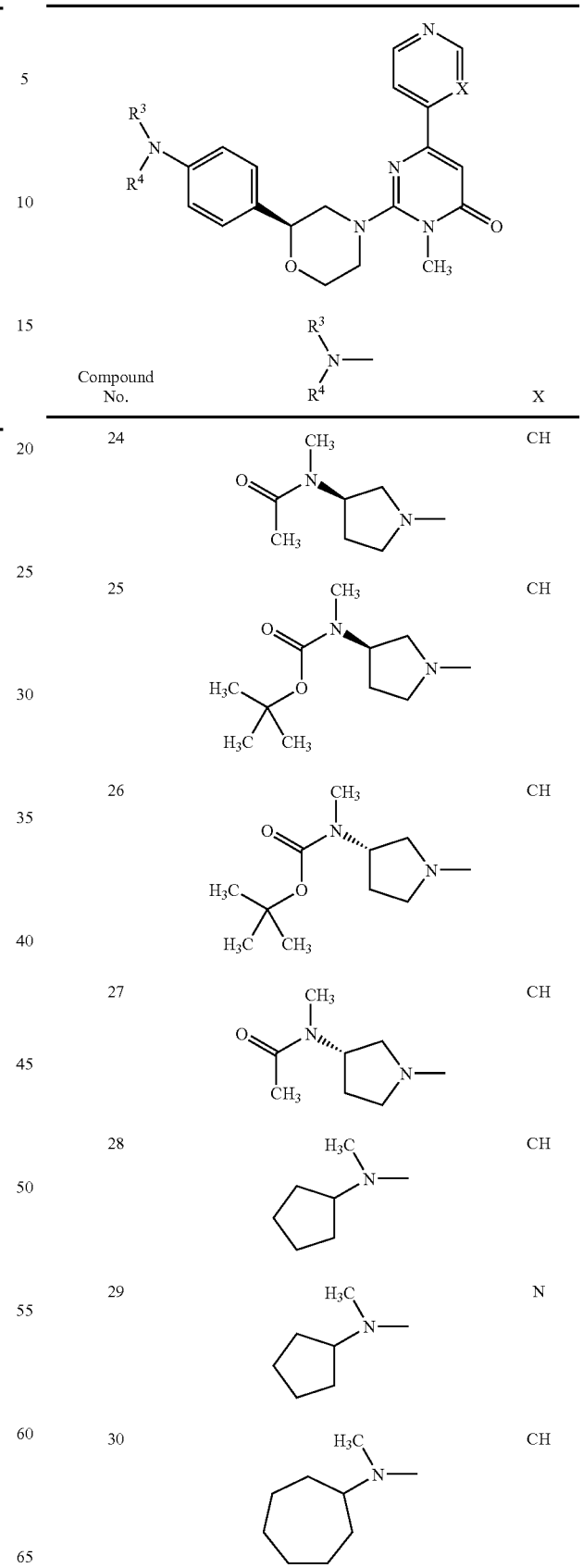

TABLE 2-continued
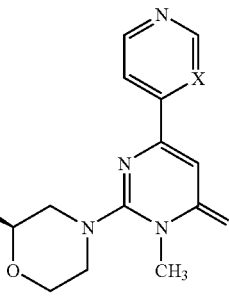
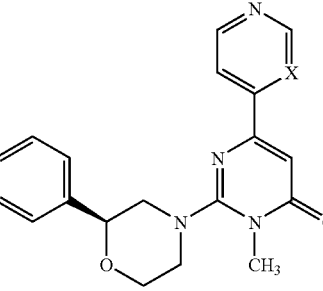

TABLE 2-continued
| Compound No. | $\underset{R^4}{\overset{R^3}{\diagdown}}N\diagup$ | X |
|---|---|---|
| 49 |  | N |
| 50 |  | CH |
| 51 |  | CH |
| 52 |  | CH |
| 53 |  | N |
| 54 |  | CH |
| 55 |  | N |
TABLE 2-continued
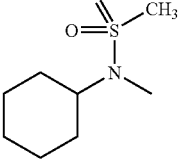
| Compound No. | $\underset{R^4}{\overset{R^3}{\diagdown}}N\diagup$ | X |
|---|---|---|
| 56 | 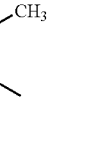 | CH |
| 57 | 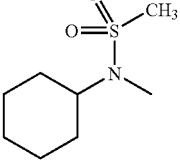 | N |
| 58 | 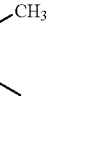 | CH |
| 59 | 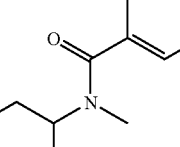 | N |
| 60 | 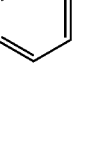 | CH |

TABLE 2-continued
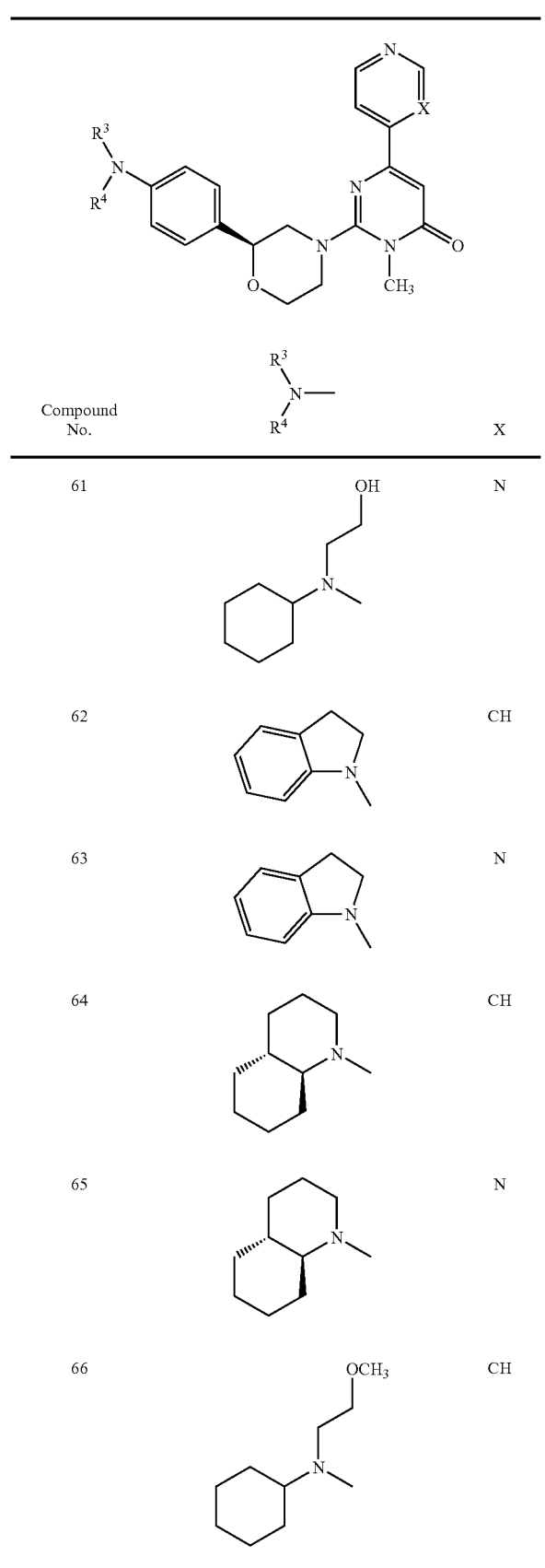
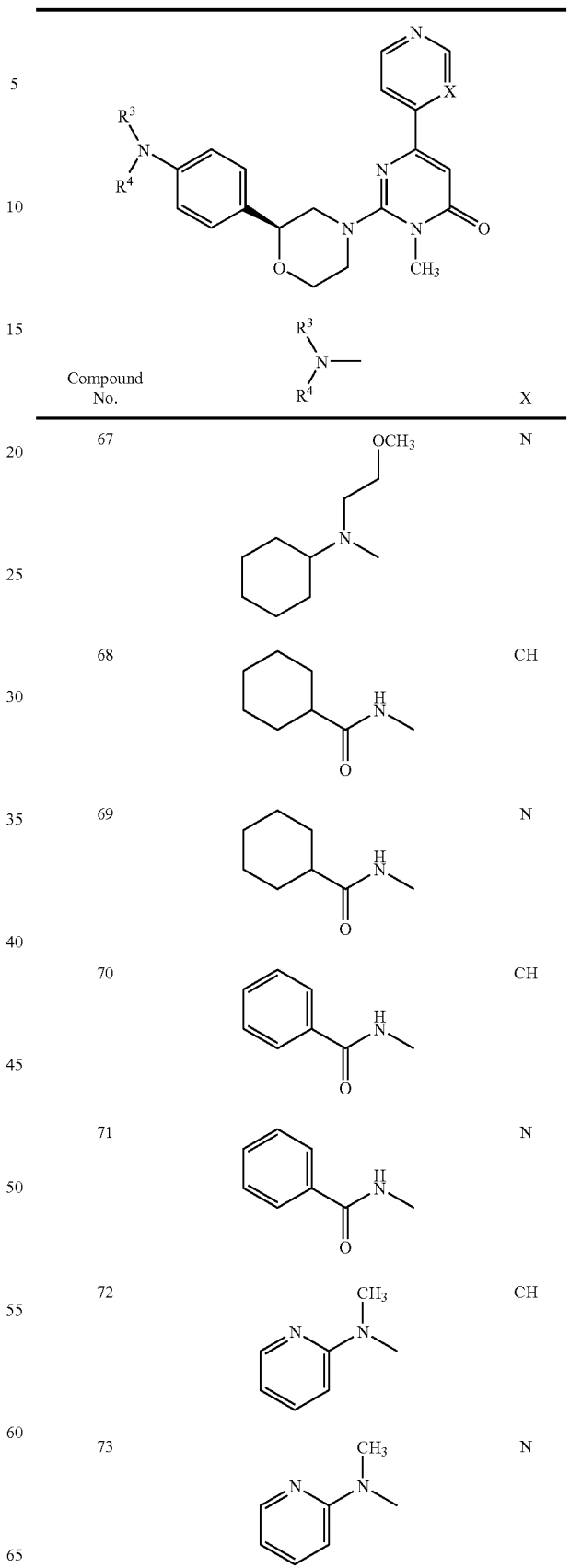

TABLE 2-continued
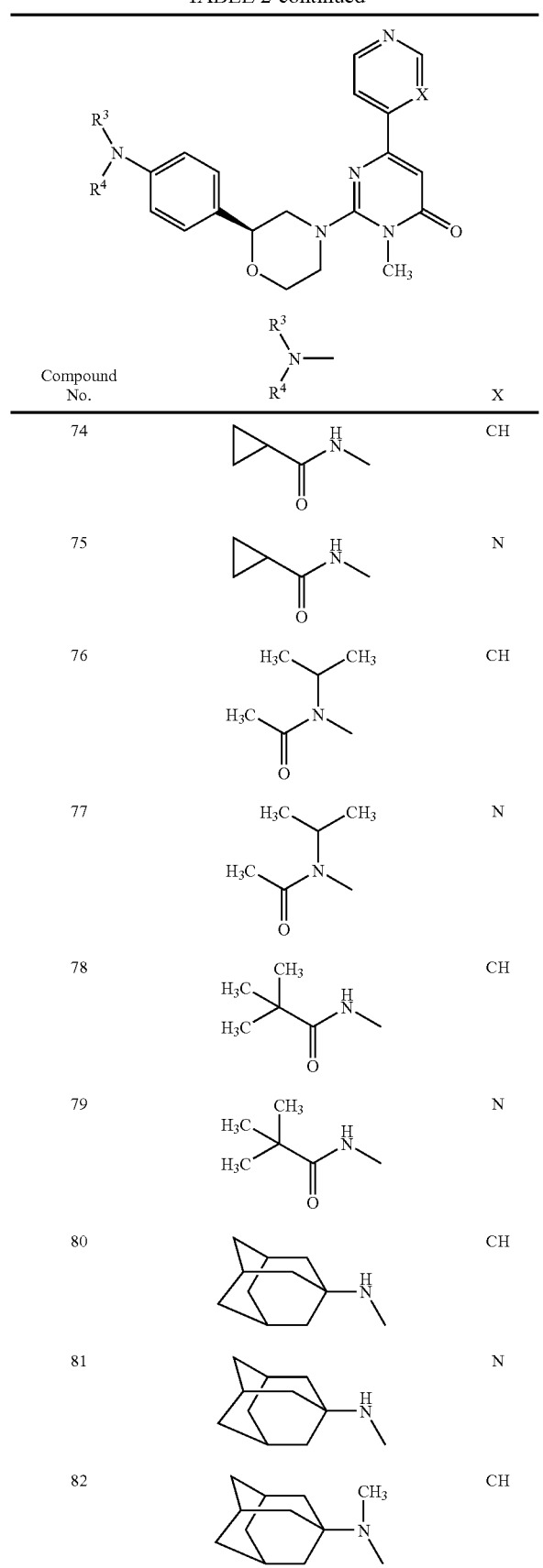
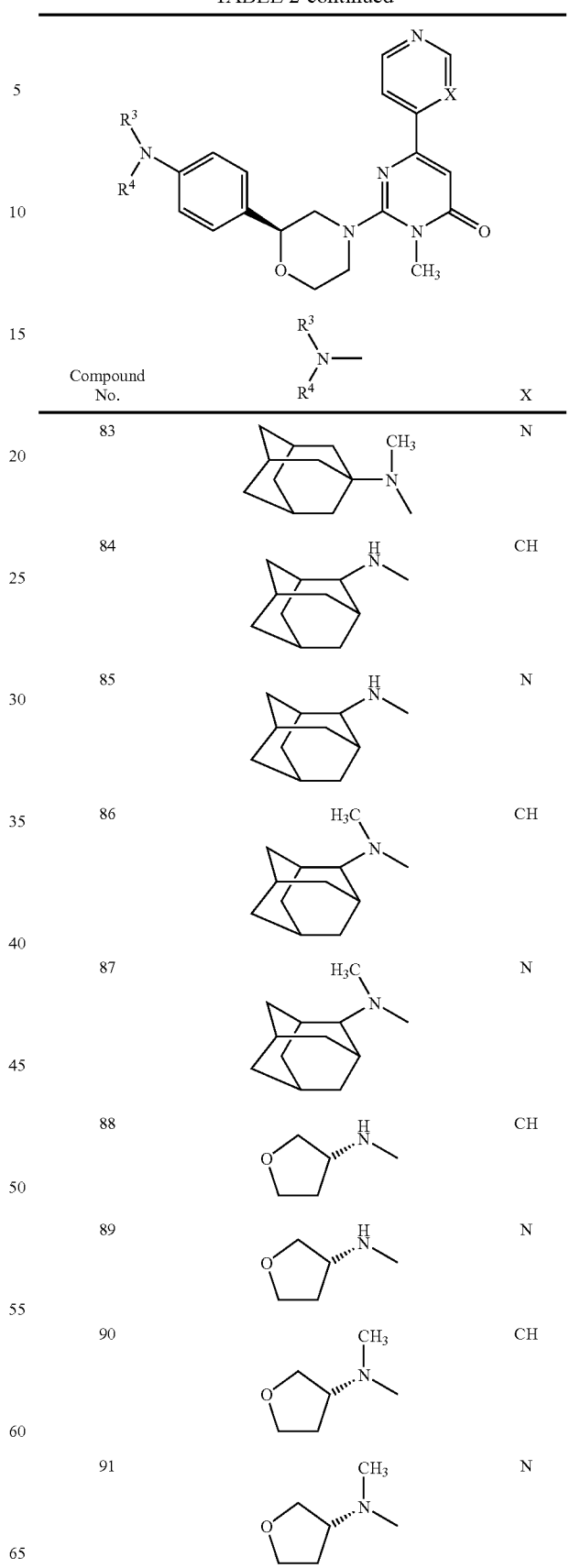

TABLE 2-continued
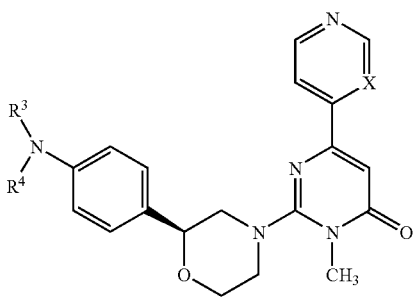
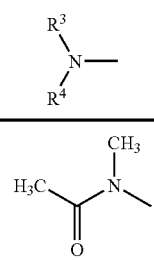
| Compound No. | $\begin{matrix}R^3\\ |\\ N-\\ |\\ R^4\end{matrix}$ | X |
|---|---|---|
| 92 | 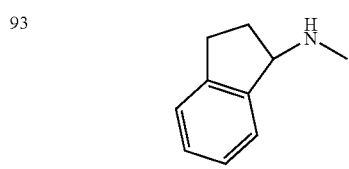 | N |
| 93 | 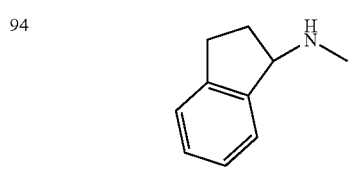 | CH |
| 94 | 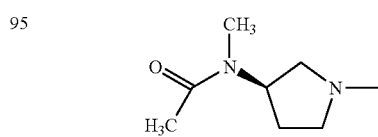 | N |
| 95 |  | N |
| 96 | 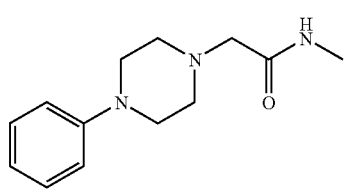 | CH |
TABLE 2-continued
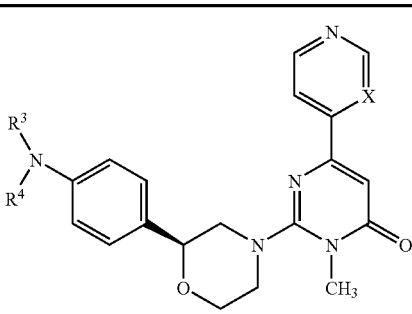
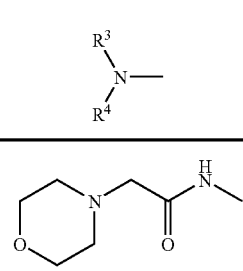
| Compound No. | $\begin{matrix}R^3\\ |\\ N-\\ |\\ R^4\end{matrix}$ | X |
|---|---|---|
| 97 | 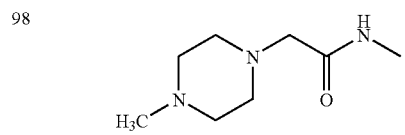 | N |
| 98 | 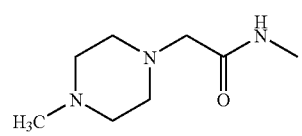 | CH |
| 99 | 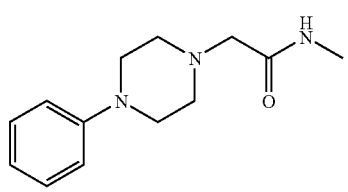 | N |
| 100 | | CH |
| 101 | | N |

| Compound No. | STRUCTURE |
|---|---|
| 201 | 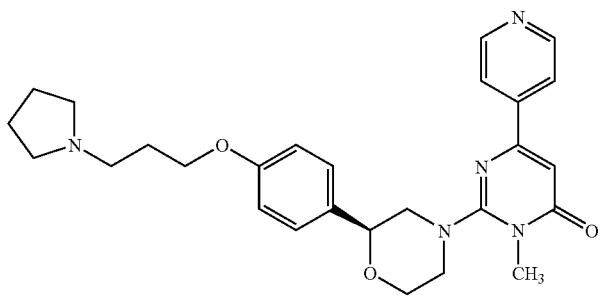 |
| 202 | 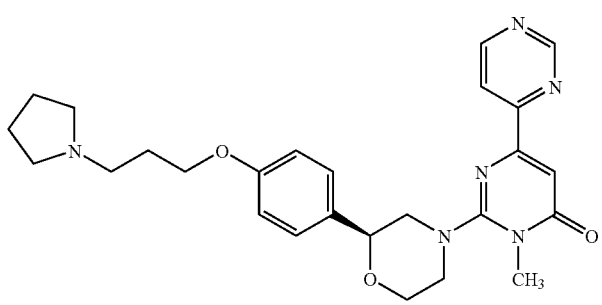 |
| 203 | 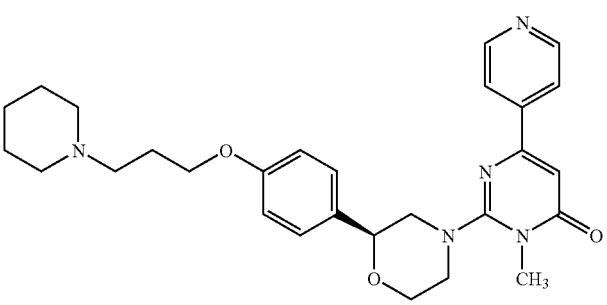 |
| 204 | 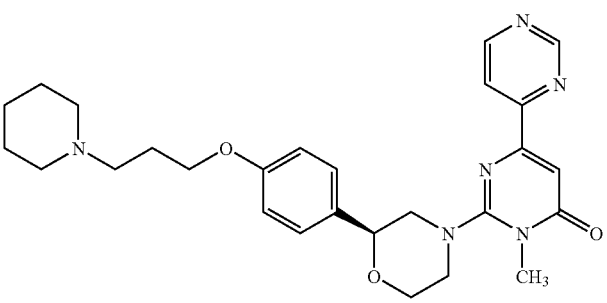 |
| 205 | 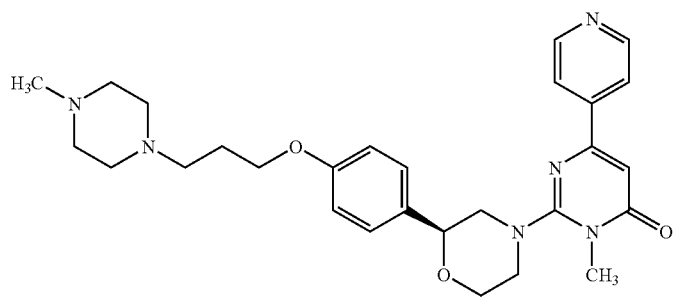 |

-continued
| Compound No. | STRUCTURE |
|---|---|
| 206 | 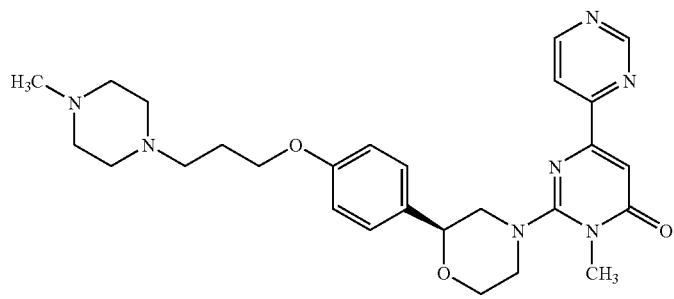 |
| 207 | 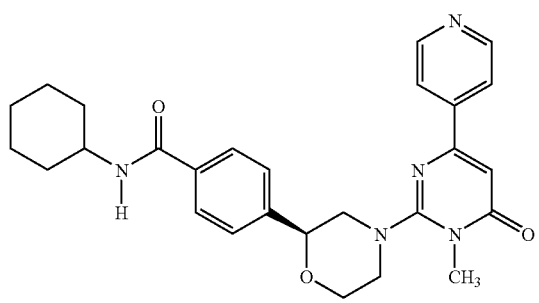 |
| 208 | 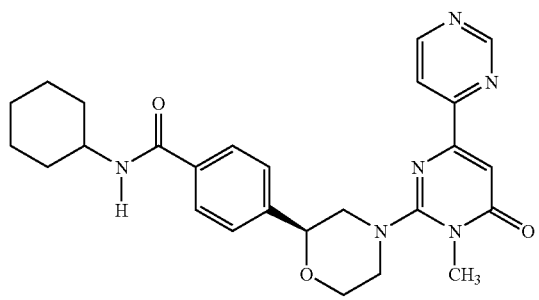 |
| 209 | 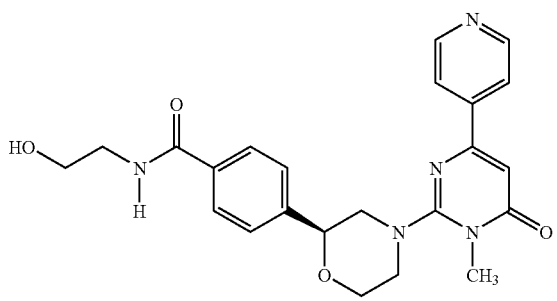 |
| 210 | 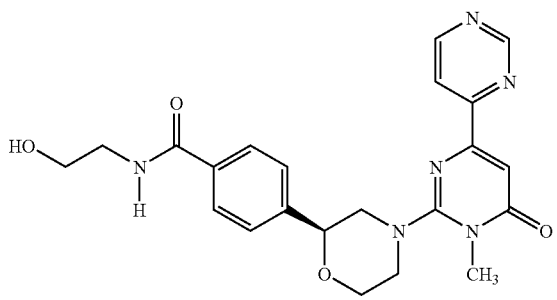 |

-continued
| Compound No. | STRUCTURE |
|---|---|
| 211 | 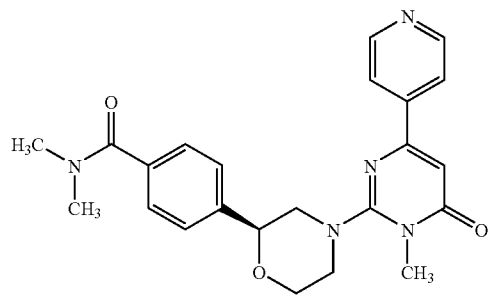 |
| 212 | 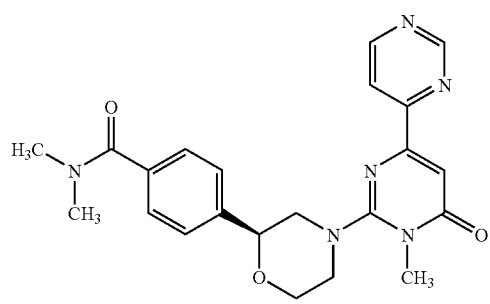 |
| 213 | 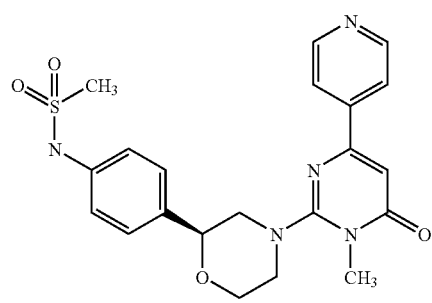 |
| 214 | 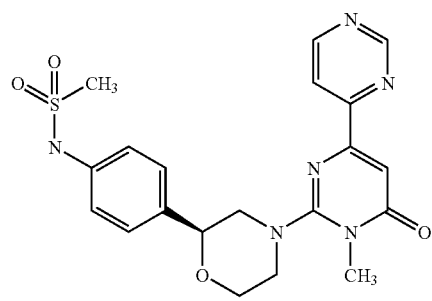 |
| 215 | 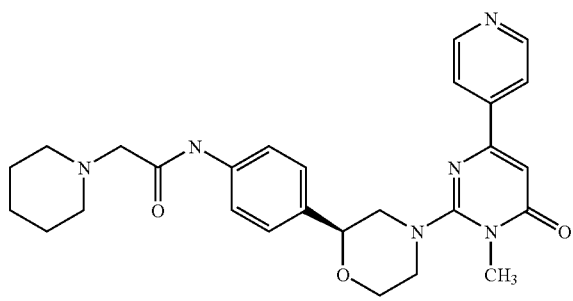 |

-continued
| Compound No. | STRUCTURE |
|---|---|
| 216 | 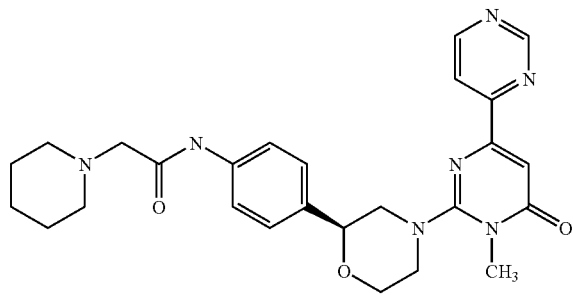 |
| 217 | 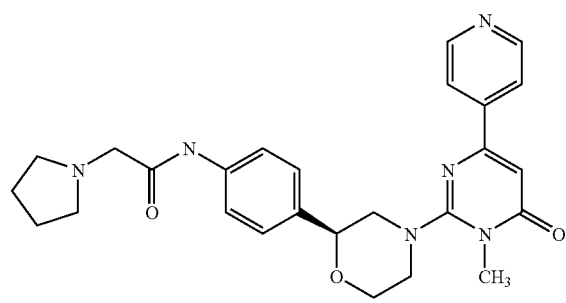 |
| 218 | 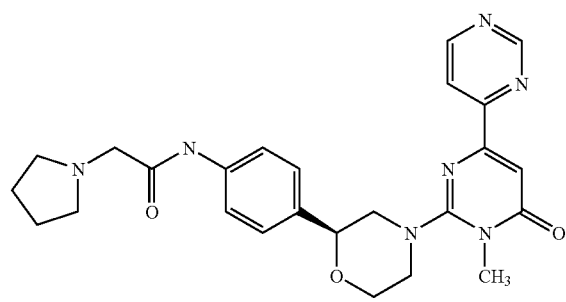 |
| 219 | 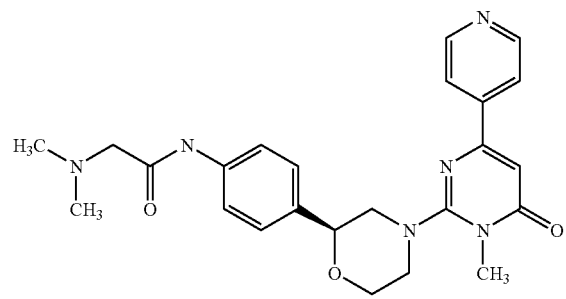 |
| 220 | 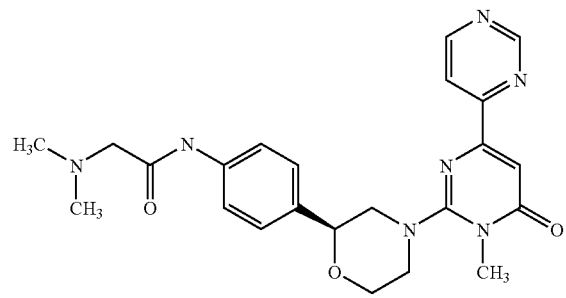 |

| Compound No. | STRUCTURE |
|---|---|
| 221 | 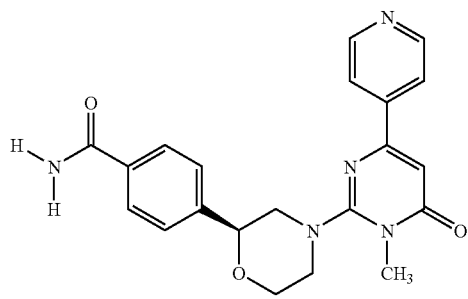 |
| 222 | 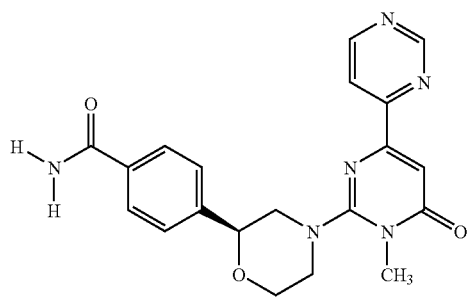 |
| 223 | 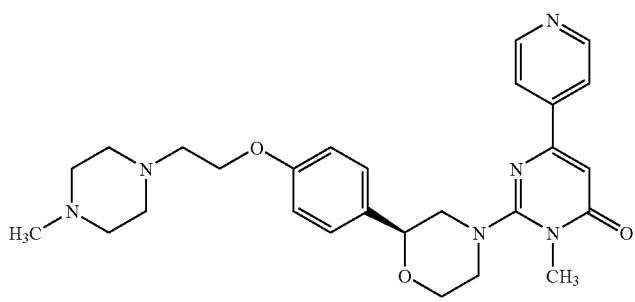 |
| 224 | 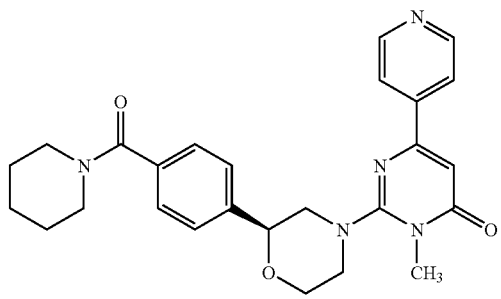 |
| 225 | 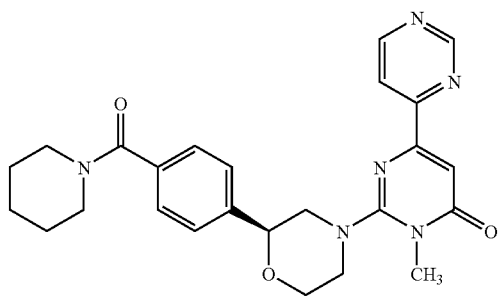 |

-continued
| Compound No. | STRUCTURE |
|---|---|
| 226 | 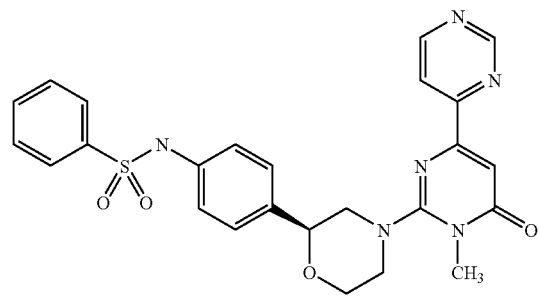 |
| 227 | 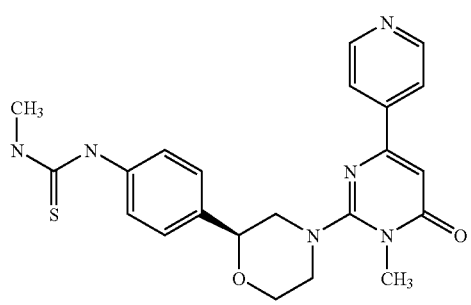 |
| 228 | 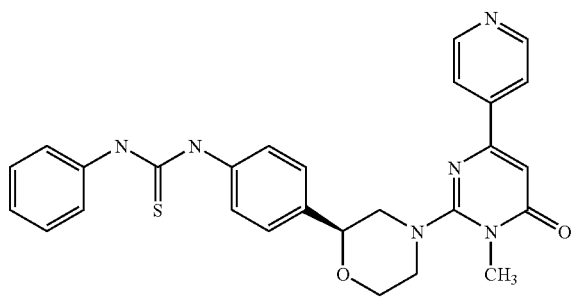 |
| 229 | 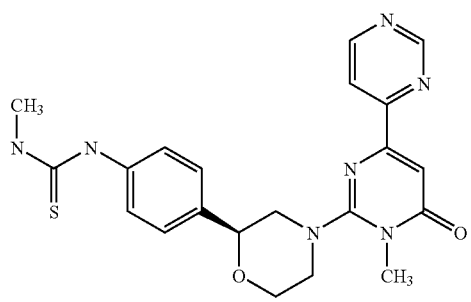 |
| 230 | 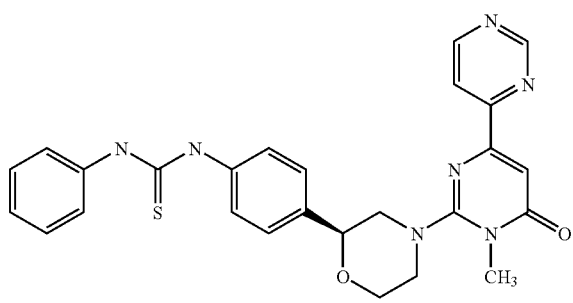 |

-continued
| Compound No. | STRUCTURE |
|---|---|
| 231 | 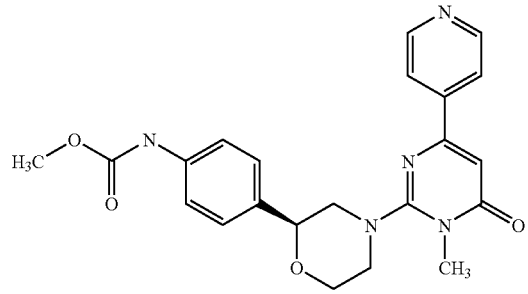 |
| 232 | 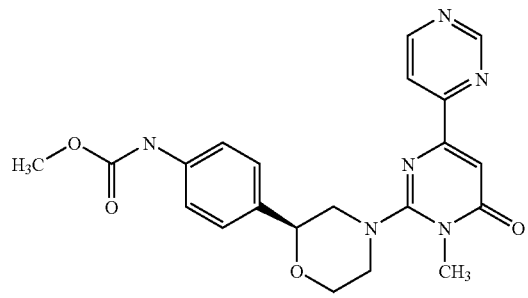 |
| 233 | 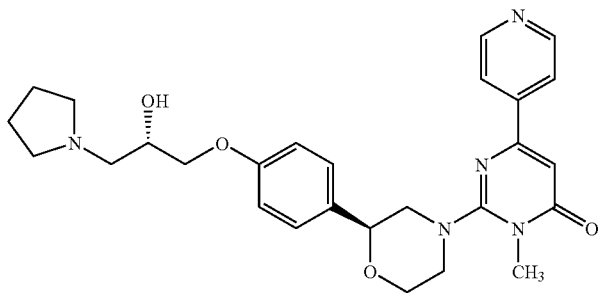 |
| 234 | 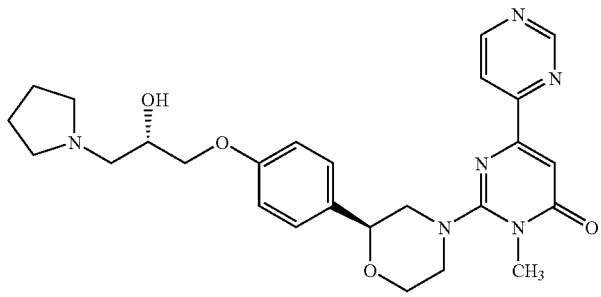 |
| 235 | 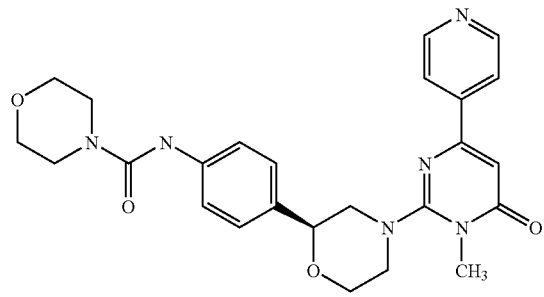 |

| Compound No. | STRUCTURE |
|---|---|
| 236 | 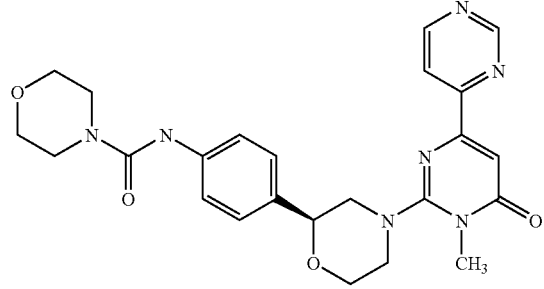 |
| 237 | 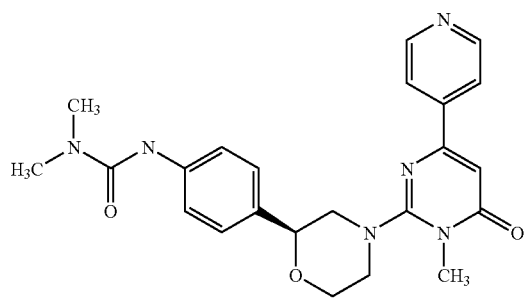 |
| 238 | 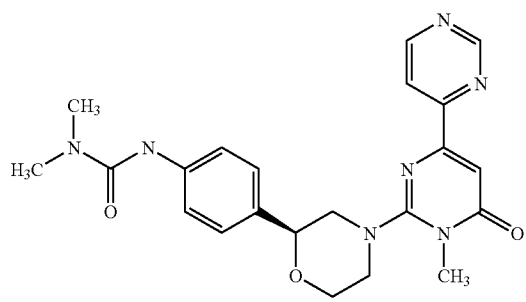 |
| 239 | 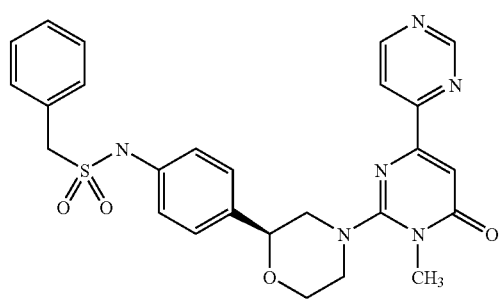 |
| 240 | 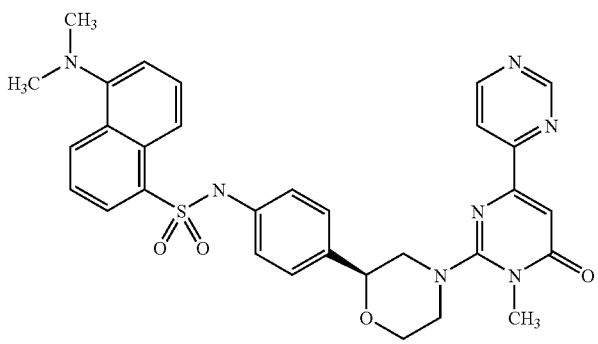 |

-continued
| Compound No. | STRUCTURE |
|---|---|
| 241 | 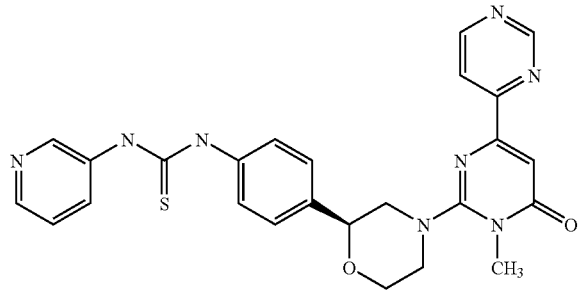 |
| 242 | 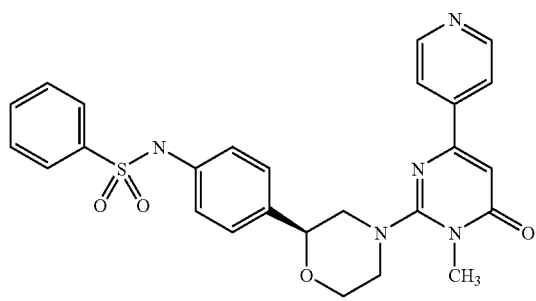 |
| 243 | 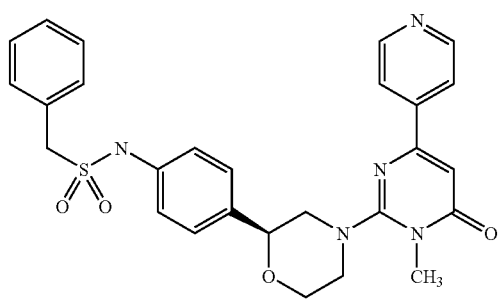 |
| 244 | 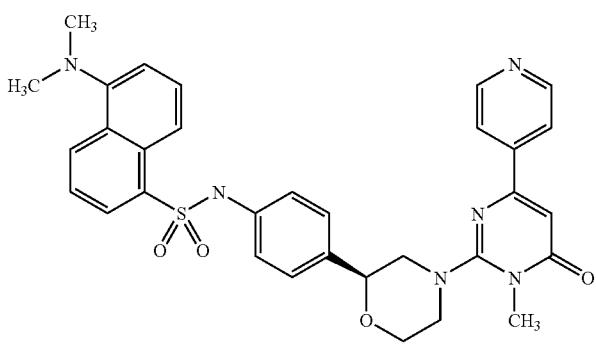 |
| 245 | 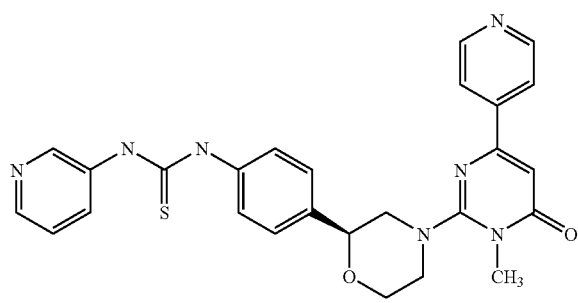 |

-continued
| Compound No. | STRUCTURE |
|---|---|
| 246 | 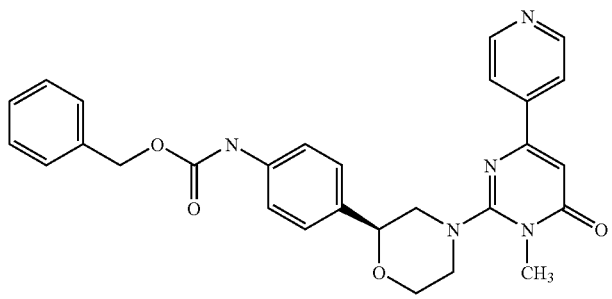 |
| 247 | 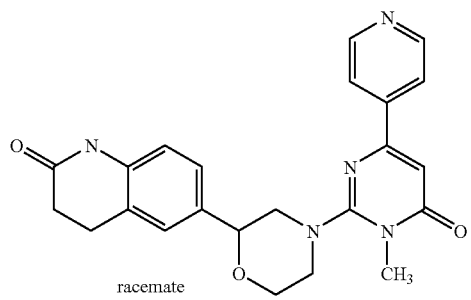 |
| 248 | 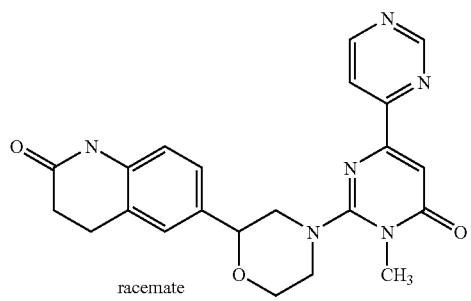 |
| 249 | 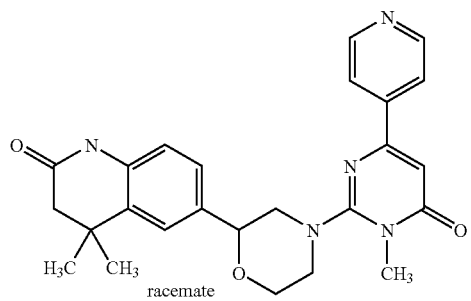 |
| 250 | 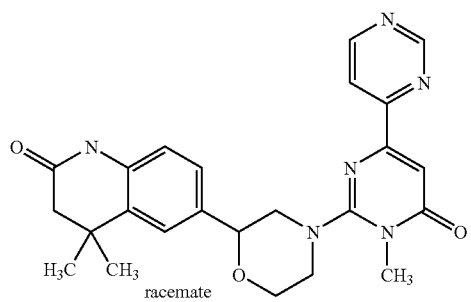 |

-continued
| Compound No. | STRUCTURE |
|---|---|
| 251 | 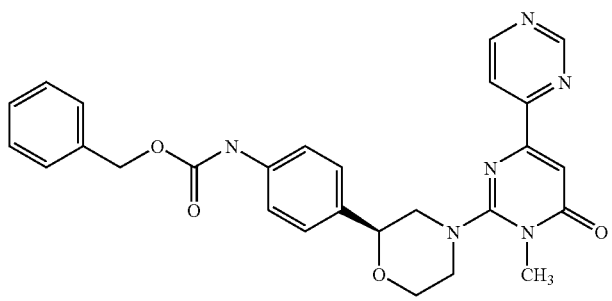 |
| 252 | 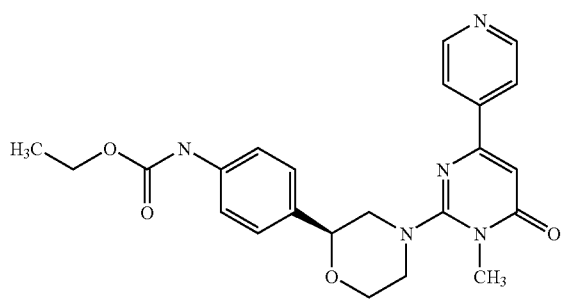 |
| 253 | 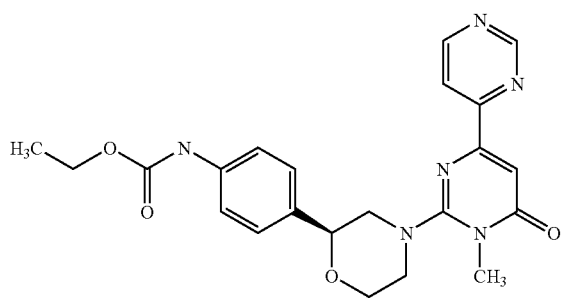 |
| 254 | 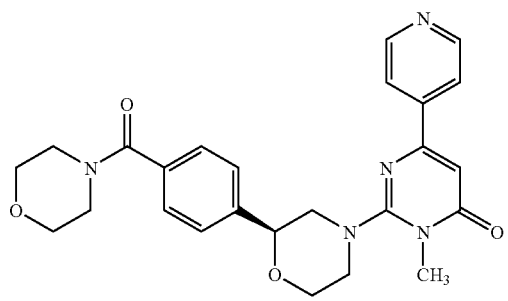 |
| 255 | 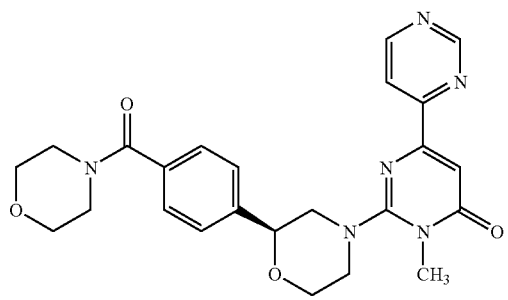 |

| Compound No. | STRUCTURE |
|---|---|
| 256 | 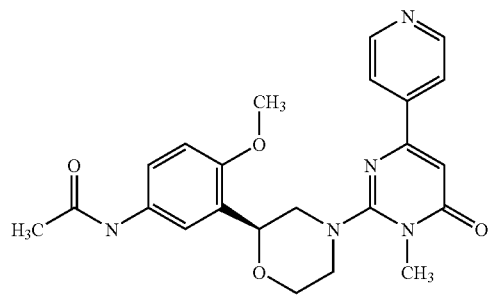 |
| 257 | 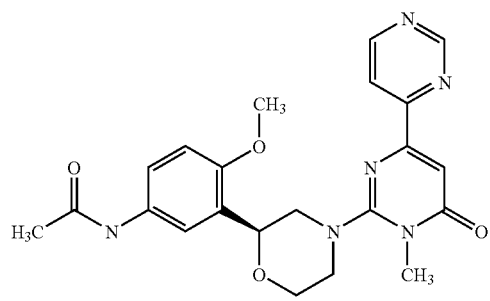 |
| 258 | 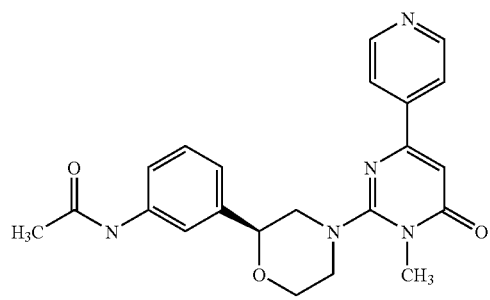 |
| 259 | 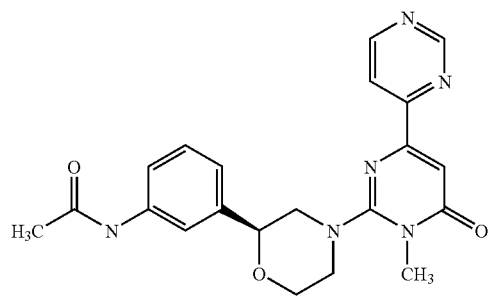 |
| 260 | 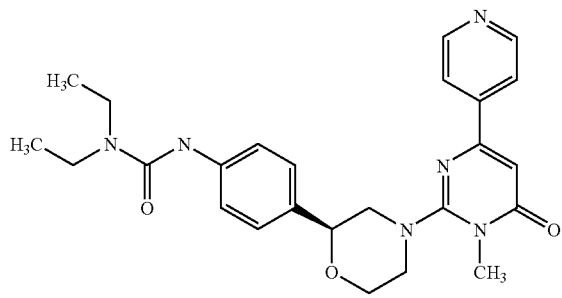 |

-continued
| Compound No. | STRUCTURE |
|---|---|
| 261 | 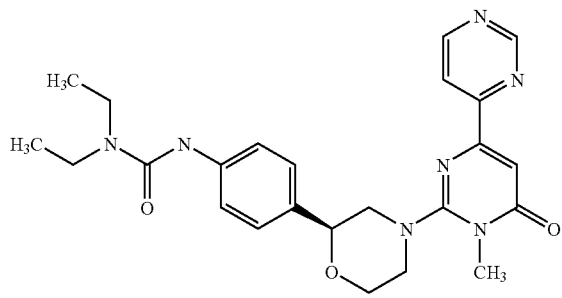 |
| 262 | 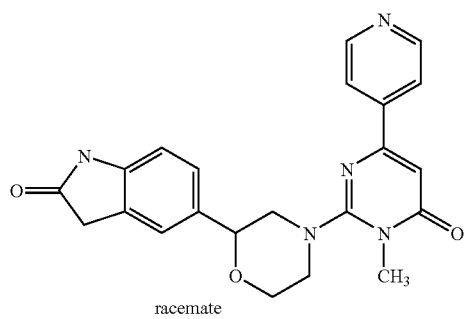<br>racemate |
| 263 | 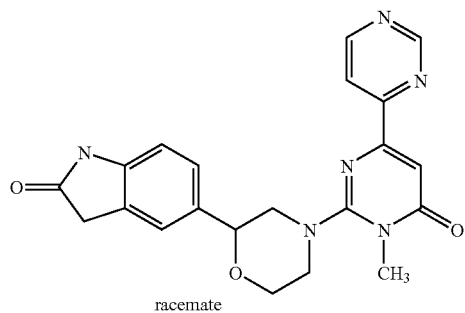<br>racemate |
| 264 | 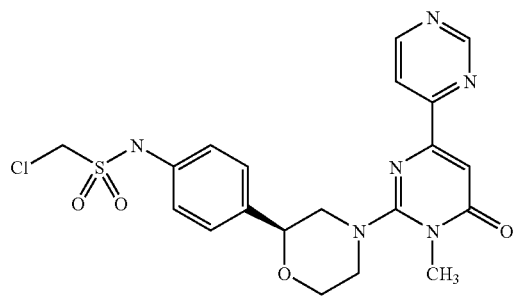 |
| 265 | 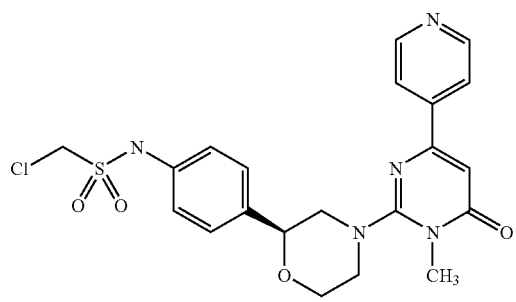 |

-continued
| Compound No. | STRUCTURE |
|---|---|
| 266 | 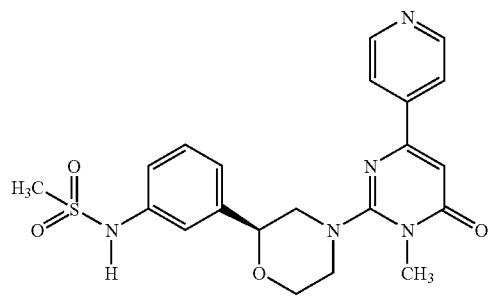 |
| 267 | 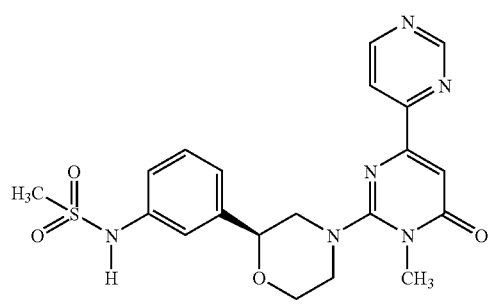 |
| 268 | 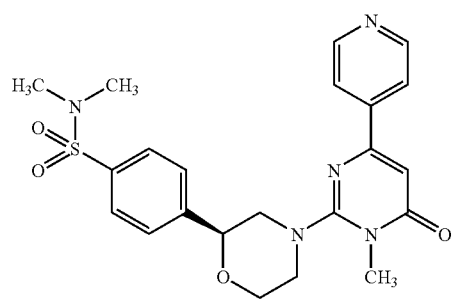 |
| 269 | 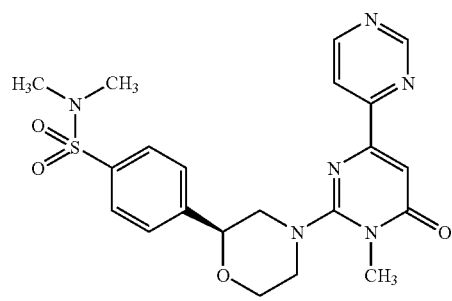 |
| 270 | 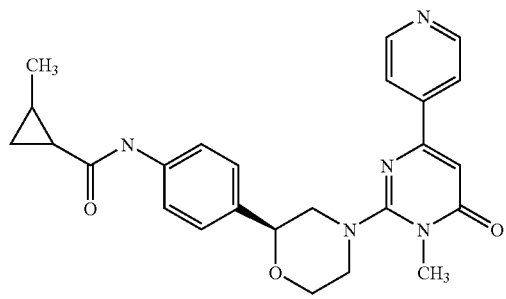 |

-continued
| Compound No. | STRUCTURE |
|---|---|
| 271 | 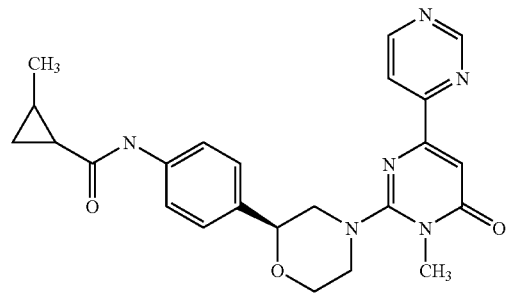 |
| 272 | 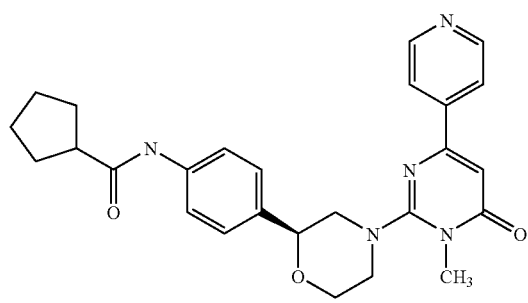 |
| 273 | 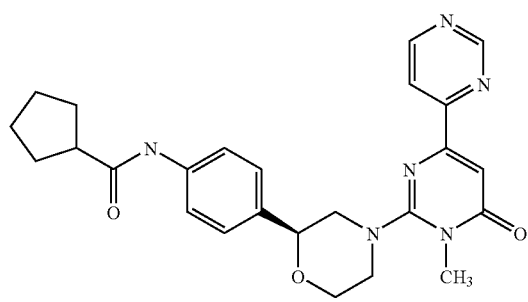 |
| 274 | 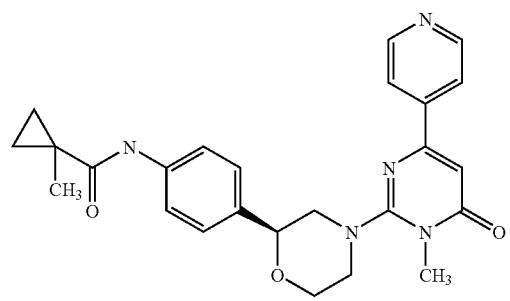 |
| 275 | 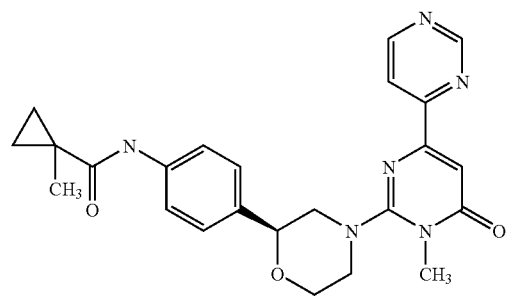 |

| Compound No. | STRUCTURE |
|---|---|
| 276 | 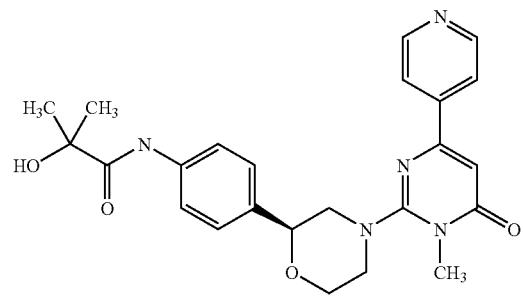 |
| 277 | 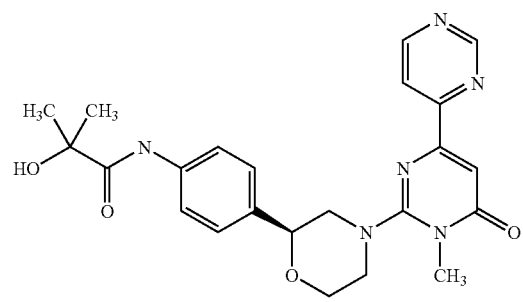 |
| 278 | 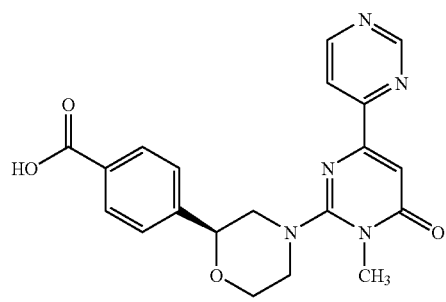 |
| 279 | 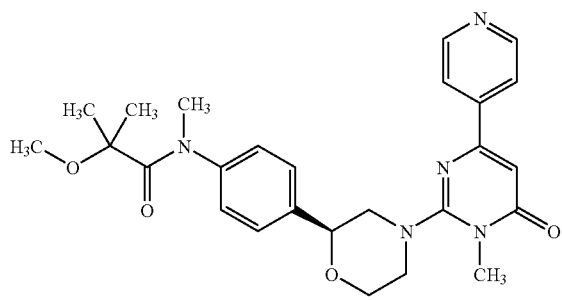 |
| 280 | 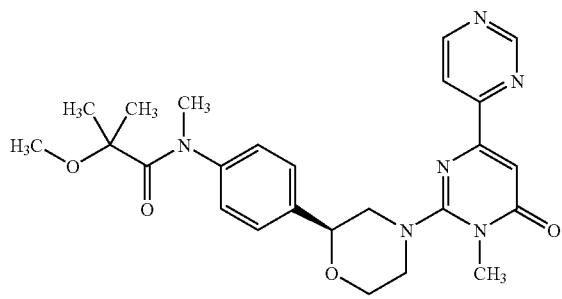 |

| Compound No. | STRUCTURE |
|---|---|
| 281 | 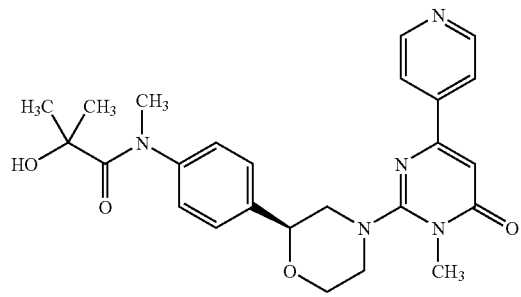 |
| 282 | 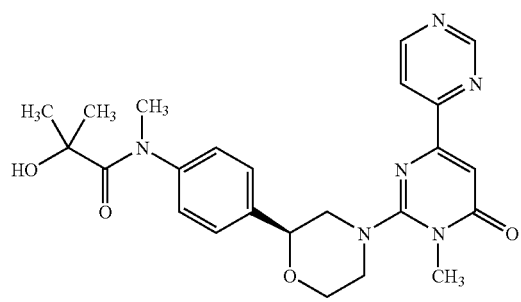 |
| 283 | 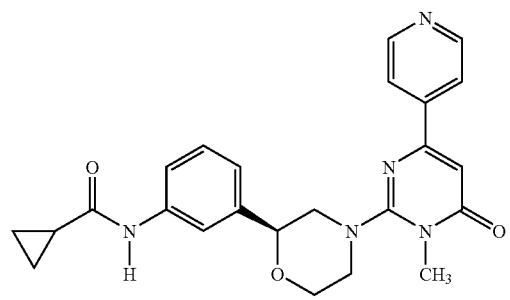 |
| 284 | 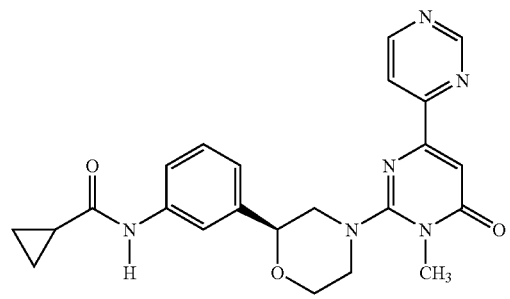 |
| 285 | 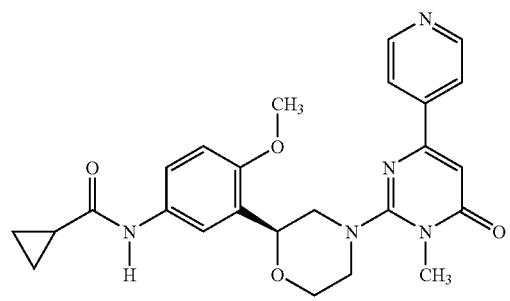 |

-continued
| Compound No. | STRUCTURE |
|---|---|
| 286 | 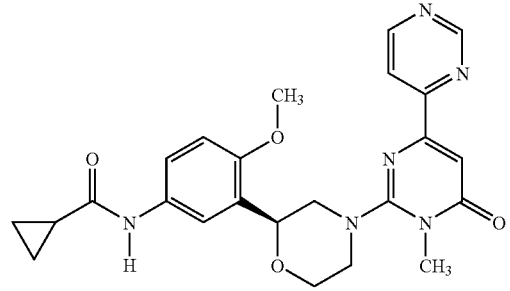 |
| 287 | 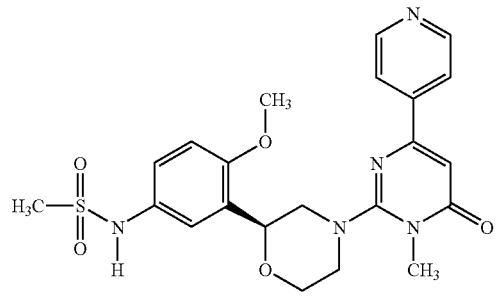 |
| 288 | 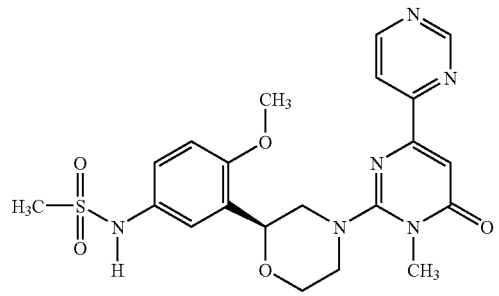 |
| 289 | 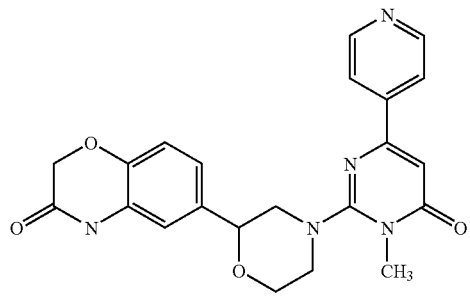<br>racemate |
| 290 | 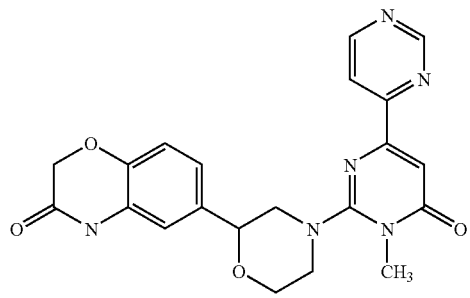<br>racemate |

| Compound No. | STRUCTURE |
|---|---|
| 291 | 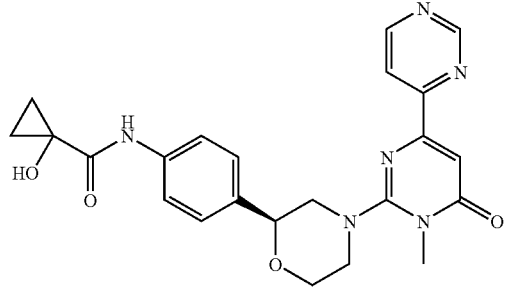 |
| 292 | 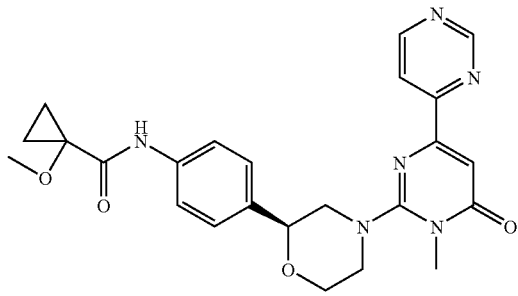 |

Particularly preferred compounds of the present invention represented by formula (I) include:

2-(2-(4-((4-Pyrrolidin-1-yl)piperidin-1-yl)phenyl)morpholin-4-yl)-3-methyl-6-pyrimidin-4-yl-3H-pyrimidin-4-one, 2-(2-(4-((4-Piperidin-1-yl)piperidin-1-yl)phenyl)morpholin-4-yl)-3-methyl-6-pyrimidin-4-yl-3H-pyrimidin-4-one, 2-(2-(4-(N-Cyclohexyl-N-methylamino)phenyl)morpholin-4-yl)-3-methyl-6-pyridin-4-yl-3H-pyrimidin-4-one, 2-(2-(4-(4-(2-Hydroxyethyl)piperazin-1-yl)phenyl)morpholin-4-yl)-3-methyl-6-pyrimidin-4-yl-3H-pyrimidin-4-one, 2-(2-(4-((3-Pyrrolidin-1-yl)pyrrolidin-1-yl)phenyl)morpholin-4-yl)-3-methyl-6-pyrimidin-4-yl-3H-pyrimidin-4-one, 2-(2-(4-(3-N-acetyl-N-methylaminopyrrolidin-1-yl)phenyl)morpholin-4-yl)-3-methyl-6-pyridin-4-yl-3H-pyrimidin-4-one, 2-{2-[4-(3-Hydroxy-azetidin-1-yl)phenyl]morpholin-4-yl}-3-methyl-6-pyridin-4-yl-3H-pyrimidin-4-one, N-(4-(4-(1-Methyl-6-oxo-4-(pyridin-4-yl)-1,6-dihydropyrimidin-2-yl)morpholin-2-yl)-phenyl)-acetamide, N-(4-(4-(1,6-Dihydro-1-methyl-6-oxo-4,4'-bipyrimidin-2-yl)morpholin-2-yl)phenyl)-acetamide, 2-(2-(4-(2-Pyridylamino)phenyl)morpholin-4-yl)-3-methyl-6-pyrimidin-4-yl-3H-pyrimidin-4-one, 2-(2-(4-Cyclopropylcarbonylamino)phenyl)morpholin-4-yl)-3-methyl-6-pyridin-4-yl-3H-pyrimidin-4-one, 2-(2-(4-Cyclopropylcarbonylamino)phenyl)morpholin-4-yl)-3-methyl-6-pyrimidin-4-yl-3H-pyrimidin-4-one, 2-(2-(4-Tetrahydrofuran-3-ylamino)phenyl)morpholin-4-yl)-3-methyl-6-pyrimidin-4-yl-3H-pyrimidin-4-one, 2-(2-(4-(N-Tetrahydrofuran-3-yl-N-methylamino)phenyl)morpholin-4-yl)-3-methyl-6-pyrimidin-4-yl-3H-pyrimidin-4-one, N-{4-[(2S)-4-(1-Methyl-6-oxo-4-pyridin-4-yl-1,6-dihydropyrimidin-2-yl)morpholin-2-yl]phenyl}-2-pyrrolidin-1-ylacetamide, N-{4-[(2S)-4-(1-Methyl-6-oxo-1,6-dihydro-4,4'-bipyrimidin-2-yl)morpholin-2-yl]phenyl}-2-pyrrolidin-1-ylacetamide, N2,N2-Dimethyl-N1-{4-[(2S)-4-(1-methyl-6-oxo-1,6-dihydro-4,4'-bipyrimidin-2-yl)morpholin-2-yl]phenyl}glycinamide, Methyl{4-[(2S)-4-(1-methyl-6-oxo-4-pyridin-4-yl-1,6-dihydropyrimidin-2-yl)morpholin-2-yl]phenyl}carbamate, Ethyl{4-[(2S)-4-(1-methyl-6-oxo-1,6-dihydro-4,4'-bipyrimidin-2-yl)morpholin-2-yl]-phenyl}carbamate, N-{4-Methoxy-3-[(2S)-4-(1-methyl-6-oxo-4-pyridin-4-yl-1,6-dihydropyrimidin-2-yl)morpholin-2-yl]phenyl}acetamide, N-{4-Methoxy-3-[(2S)-4-(1-methyl-6-oxo-1,6-dihydro-4,4'-bipyrimidin-2-yl)morpholin-2-yl]phenyl}acetamide, and N-{3-[(2S)-4-(1-Methyl-6-oxo-4-pyridin-4-yl-1,6-dihydropyrimidin-2-yl)morpholin-2-yl]phenyl}acetamide, an optically active isomer thereof, or a pharmaceutically acceptable salt thereof.

Salts of the aforementioned preferred compound, and solvates or hydrates of the aforementioned compounds and salts thereof are also preferred.

The compounds represented by the aforementioned formula (I) can be prepared, for example, according to the method explained below.

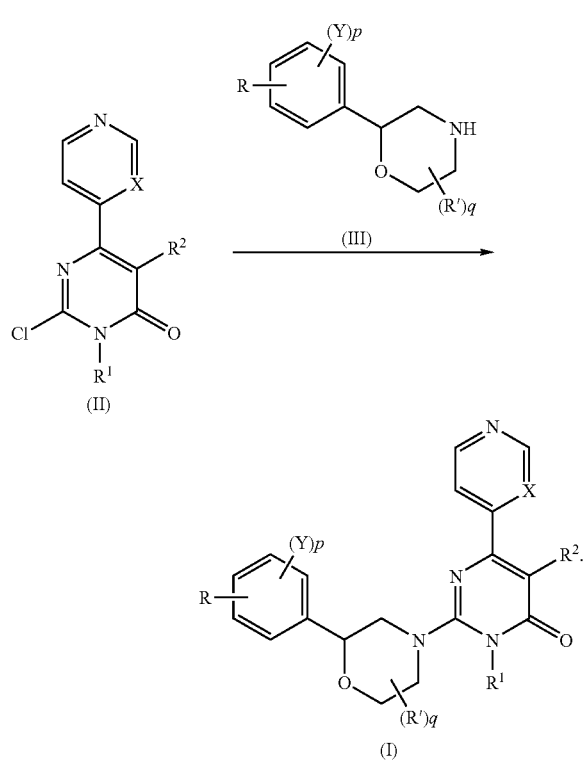

(In the above scheme, definitions of each symbol are the same as those already described.)

The 2-chloropyrimidone represented by the above formula (II) is prepared easily by the method described in the specification of WO2003/027080 and WO2003/037888.

Then the chloride derivative (II) is allowed to react with the amine (III) or salts thereof in the presence of a base such as sodium hydroxide, potassium hydroxide, sodium methoxide, sodium ethoxide, sodium carbonate, sodium hydrogencarbonate, potassium carbonate, triethylamine, diisopropylethylamine, and 1,8-diazabicyclo[5,4,0]undec-7-en for 1 to 100 hours at a suitable temperature ranging from 0° C. to 200° C. under nitrogen or argon atmosphere or under ordinary air to afford the desired compound (I).

Examples of a solvent for the reactions include, for example, alcoholic solvent such as methanol, ethanol, 1-propanol, isopropanol, tert-butanol, ethylene glycol, propylene glycol; etheric solvents such as diethyl ether, tert-butyl methyl ether, tetrahydrofuran, isopropyl ether; hydrocarbonic solvents such as benzene, toluene, xylene; halogenated hydrocarbonic solvents such as dichloromethane, chloroform, dichloroethane; aprotic polar solvents such as formamide, N,N-dimethylformamide, N,N-dimethylacetamide, N-methylpyrrolidone, dimethyl sulfoxide, sulfolane, hexamethylphosphoric triamide, water and the like. Generally, a single solvent or a mixture of two or more solvents may be used so as to be suitable to a base used.

The compounds of the present invention have inhibitory activity against TPK1, and they inhibit TPK1 activity in neurodegenerative diseases such as Alzheimer disease, thereby suppress the neurotoxicity of Aβ and the formation of PHF and inhibit the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitis, postencephalitic parkinsonism, pugilistic encephalosis, Guam parkinsonism-dementia complex, Lewy body disease, Pick's disease, corticobasal degeneration frontotemporal dementia, vascular dementia, traumatic injuries, brain and spinal cord trauma, peripheral neuropathies, retinopathies and glaucoma, non-insulin dependent diabetes, obesity, manic depressive illness, schizophrenia, alopecia, breast cancer, non-small cell lung carcinoma, thyroid cancer, T or B-cell leukemia, and several virus-induced tumors. As the compound of the present invention has good safety and good pharmacokinetics, the compound has preferable characteristics as a medicament.

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient),.and the dose may be administered once a day or several times a day as divided portions, or once in several days. When the medicament is used as an injection, administrations may preferably be performed continuously or intermittently in a daily dose of 0.001 to 3000 mg (the weight of an active ingredient) to an adult.

EXAMPLES

The present invention will be explained more specifically with reference to examples. However, the scope of the present invention is not limited to the following examples. The compound number in the examples corresponds to that in the table above.

Example 1

N-(4-((2S)-4-(1-Methyl-6-oxo-4-(pyridin-4-yl)-1,6-dihydropyrimidin-2-yl)-morpholin-2-yl)phenyl)acetamide (Compound No. 39)

2-bromo-(1S)-1-(4-bromophenyl)ethanol

A borane-tetrahydrofuran complex (1.0 M solution in tetrahydrofuran, 270 ml, 270 mmol) was added to the solution of (S)-CBS ((S)-2-Methyl-CBS-oxazaborolidine, 50 ml, 1.0M solution in toluene) at −30° C. over 15 min and the solution was stirred for 15 minutes. 4-Bromophenacyl bromide (75.0 g, 270 mmol) in dichloromethane (350 ml) was dropped over 70 minutes keeping the temperature −32 to −28° C. After one hour stirring, solution was warmed to room temperature, and methanol (10 ml) was added slowly and then 0.5 M hydrochloric acid (300 ml) was dropped over 10 minutes. The solution was filtered after 40 minutes stirring and filtrate was extracted by dichloromethane. The combined organic layer was washed with 0.5 M hydrochloric acid, 0.1M aqueous sodium hydroxide and brine and dried over anhydrous sodium sulfate. Concentration of the organic layer yielded 2-bromo-(1S)-1-(4-bromophenyl)ethanol (77 g) as a pale brown oil.

(2S)-2-(4-bromophenyl)oxirane

Aqueous sodium hydroxide (1M, 400 ml) was added to 2-bromo-(1S)-1-(4-bromophenyl)ethanol (77.0 g) in diethyl ether (400 ml) and stirred at room temperature for 5 hours. The organic layer was separated and water layer was extracted with ether. Combined organic layer was washed with brine and dried over anhydrous sodium sulfate. Removal of the solvent yielded (2S)-2-(4-bromophenyl)oxirane (55.0 g) as a pale brown oil.

(1S)-1-(4-bromophenyl)-2-((1R)-1-phenylethylamino)ethanol

A mixture of (2S)-2-(4-bromophenyl)oxirane (55.0 g) and (R)-1-phenylethylamine (98.2g, 810 mmol) was heated at 80° C. for 6 hours. Addition of isopropyl ether (200 ml) to the residue after distillation of excess phenethylamine and successive filtration yielded (1S)-1-(4-bromophenyl)-2-((1R)-1-phenylethylamino)ethanol (57.0 g) as white crystals. Further crystallization was performed by the concentration of the filtrate in vacuo and cooling the residue in refrigerator. Filtration of the crystal with isopropyl ether (30 ml) yielded additional title compound (5.60 g) as crystals (72.4% yield, 3 steps).

(6S)-6-(4-bromophenyl)-4-((1R)-1-phenyethyl)morpholin-3-one

A solution of chloroacetyl chloride (24.3g, 215 mmol) in dichloromethane (100 ml) was dropped into the ice-cooled solution of (1S)-1-(4-bromophenyl)-2-((1R)-1-phenylethylamino)ethanol (62.6 g, 215 mmol) and triethylamine (21.8 g, 215 mmol) in dichloromethane (600 ml) over 30 minutes and stirred for one hour at the same temperature. Resulting solution was washed with 0.5 M hydrochloric acid, saturated sodium hydrogen carbonate, brine and dried over anhydrous magnesium sulfate. The solvents were removed under reduced pressure and potassium hydroxide (85%, 16.1 g, 244 mmol) was added to a solution of resulting pale brown oil in isopropyl alcohol (600 ml) and stirred for 16 hour. The solvent was removed in vacuo and the residue was partitioned between water and ethyl acetate. The organic layer was washed with 0.5 M hydrochloric acid, saturated sodium hydrogen carbonate, brine and dried over anhydrous magnesium sulfate. Removal of the solvent under reduced pressure furnished (6S)-6-(4-bromophenyl)-4-((1R)-1-phenyethyl) morpholin-3-one (70.2 g) as a brown oil.

(2S)-2-(4-bromophenyl)-4-((1R)-1-phenylethyl)morpholine

A borane-tetrahydrofuran complex (1.0M solution in tetrahydrofuran, 510 ml, 510 mm) was added to the ice-cooled solution of (6S)-6-(4-bromophenyl)-4-((1R)-1-phenyethyl)-morpholin-3-one (70.2 g) in tetrahydrofuran (500 ml) over 45 minutes and the solution was stirred at the same temperature for one hour and room temperature for 30 minutes. After careful addition of methanol (60 ml) to the ice-cooled solution, the solvent was removed under reduced pressure and the residue in methanol (750 ml) and 1M aqueous sodium hydroxide (280 ml) was stirred at 80° C. for one hour with addition of 1M aqueous sodium hydroxide (70 ml) in every 15 minutes. The solvents was removed under reduced pressure and the residue was partitioned between water and ethyl acetate. The organic layer was washed with water and brine and dried over anhydrous magnesium.sulfate. Removal of the solvent yielded (2S)-2-(4-bromophenyl)-4-((1R)-1-phenylethyl)morpholine (65.0 g, 96.3% yield, 2 steps) as white crystals.

Melting point; 85-87° C.

IR : 1487, 1449, 1117, 1098, 809, 758, 699, 550 cm$^{-1}$ $^1$H-NMR(CDCl$_3$) δ: 1.35(3H,d), 2.10(2H,m), 2.60(1H,m), 3.05(1H,m), 3.35(1H,q), 3.75(1H,m), 3.89(1H,m), 4.55(1H, m), 7.25(7H,m), 7.46(2H,d)

(2S)-2-(4-aminophenyl)-4-((1R)-1-phenylethyl)morpholine

A solution of (2S)-2-(4-bromophenyl)-4-((1R)-1-phenylethyl)morpholine (15.6 g, 45 mmol), benzophenone imine (9 g, 50 mmol), tris(dibenzylideneacetone)-dipalladium(0)-chloroform adduct (0.93 g, 0.9 mmol), sodium tert-butoxide (6.0 g, 63 mmol) and 2-(di-t-butylphosphino)biphenyl (0.53 g, 1.8 mmol) in toluene (135 ml) was stirred at 95° C. for 4 hours. The solvent was removed in vacuo and the residue was partitioned between water and ethyl acetate. The organic layer was dried over anhydrous sodium sulfate and the solvent was removed under reduced pressure. To a solution of the resulting residue in tetrahydrofuran (180 ml) was added 6N hydrochloric acid (180 ml) and the mixture was stirred at room temperature for one hour. The solvent was removed in vacuo and the residue was partitioned between water and ethyl acetate. The organic layer was dried over anhydrous sodium sulfate and the solvent was evaporated. The resulting residue was purified by column chromatography on silica gel (hexane-AcOEt, 2:1) to give (2S)-2-(4-aminophenyl)-4-((1R)-1-phenylethyl)morpholine (12.2 g, 96%) as an oil.

N-(4-((2S)-4-((1R)-1-Phenylethyl)morpholin-2-yl)phenyl)acetamide

To a solution of (2S)-2-(4-aminophenyl)-4-((1R)-1-phenylethyl)morpholine (7.9 g, 28 mmol) and triethylamine (8.5 g, 84 mmol) in tetrahydrofuran (180 ml) was added acetyl chloride (4.4 g, 56 mmol). The mixture was stirred at room temperature for 2 hours and partitioned between water and chloroform. The organic extract was washed with brine and dried over anhydrous sodium sulfate. The solvent was removed under reduced pressure and the precipitated crystals were collected by filtration, washed with isopropyl ether to give N-(4-((2S)-4-((1R)-1-phenylethyl)morpholin-2-yl)phenyl)-acetamide (6.47 g, 71%) as yellow crystals.

N-(4-((2S)-morpholin-2-yl)phenyl)acetamide

To a solution of N-(4-((2S)-4-((1R)-1-phenylethyl)morpholin-2-yl)phenyl)acetamide (6.47 g, 20 mmol) and ammonium formate (6.3 g, 100 mmol) in mixture of tetrahydrofuran (136 ml), methanol (270 ml) and water (70 ml) was added 10% palladium on carbon (wet, 270 mg) and the solution was stirred at 95° C. for 3 hours. After filtration, the solvent was removed in vacuo and the residue was partitioned between water and dichloromethane. The organic layer was dried over anhydrous sodium sulfate and the solvent was evaporated under reduced pressure to give N-(4-((2S)-morpholin-2-yl)phenyl)acetamide (5.78 g, quant.) as an yellow oil.

N-(4-((2S)-4-(1-Methyl-6-oxo-4-(pyridin-4-yl)-1,6-dihydropyrimidin-2-yl)morpholin-2-yl)phenyl)acetamide A solution of N-(4-((2S)-morpholin-2-yl)phenyl)acetamide (2.63 g, 11.9 mmol), 2-chloro-1-methyl-6-oxo-4-(pyridin-4-yl)-1,6-dihydropyrimidine (2.60 g, 11.9 mmol), and triethylamine (3.60 g, 35.7 mmol) in tetrahydrofuran (100 ml) was stirred at 95° C. for one hour. The solvent was removed in vacuo and the residue was partitioned between water and dichloromethane. The organic layer was dried over anhydrous sodium sulfate and the solvent was removed under reduced pressure. The resulting residue was purified by column chromatography on silica gel (chloroform-methanol, 10:1) to afford N-(4-((2S)-4-(1-Methyl-6-oxo-4-(pyridin-4-yl)-1,6-dihydropyrimidin-2-yl)morpholin-2-yl)phenyl)acetamide (2.8 g, 58%) as pale yellow crystals.

Example 2

N-(4-((2S)-4-(1,6-Dihydro-1-methyl-6-oxo-4,4'-bipyrimidin-2-yl)-morpholin-2-yl)-phenyl)acetamide (Compound No. 40)

A solution of N-(4-((2S)-morpholin-2-yl)phenyl)acetamide (5.78 g, 26.2 mmol), 2-chloro-1,6-dihydro-1-methyl-6-oxo-4'4-bipyrimidine (4.00 g, 18 mmol), and triethylamine (6.00 g, 60 mmol) in tetrahydrofuran (100 ml) was stirred at 95° C. for one hour. The solvent was removed in vacuo and the residue was partitioned between water and dichloromethane. The organic layer was dried over anhydrous sodium sulfate and the solvent was evaporated under reduced pressure. The resulting residue was purified by column chromatography on silica gel (chloroform-methanol, 10:1) to afford N-(4-((2S)-4-(1,6-Dihydro-1-methyl-6-oxo-4,4'-bipyrimidin-2-yl)morpholin-2-yl)phenyl)acetamide (5.7 g, 30%) as pale yellow crystals.

Example 3

(S)-2-(2-(4-(N-cyclohexyl-N-methylamino)phenyl)morpholin-4-yl)-3-methyl-6-(4-pyridyl)-pyrimidin-4-one (Compound No. 10)

(2S)-2-(4-(cyclohexylamino)phenyl)-4-((1R)-1-phenylethyl)morpholine

To a suspension of (2S)-2-(4-bromophenyl)-4-((1R)-1-phenylethyl)morpholine (7.62 g, 22.0 mmol), palladium acetate (198 mg, 0.88 mmol), 2-(di-t-butylphosphino) biphenyl (525 mg, 1.76 mmol), and sodium tert-butoxide (2.96 g, 30.8 mmol) in toluene (40 ml) was added cyclohexylamine (3.78 ml, 33.0 mmol) at room temperature. After heating at 90° C. for 2.5 hours, the resulting suspension was passed through a Celite column. The filtrate was concentrated under reduced pressure, and the residue was purified by silica gel chromatography eluting 5-25% of ethyl acetate in hexane to afford (S)-2-(4-(cyclohexyl-amino)phenyl)-4-((R)-1-phenylethyl)morpholine (6.95 g, 87%) as white crystals.

(2S)-2-(4-(N-cyclohexyl-N-methylamino)phenyl)-4-((1R)-1-phenylethyl)morpholine

To a solution of (S)-2-(4-(cyclohexylamino)phenyl)-4-((R)-1-phenylethyl)morpholine (6.95 g, 19.1 mmol) and formalin (35%, 8.18 ml, 95.4 mmol) was added sodium triacetoxyborohydride (12.1 g, 57.2 mmol) at room temperature. After stirring for 30 minutes, the resulting suspension was partitioned between ethyl acetate and 1 N sodium hydroxide. The aqueous layer was extracted with ethyl acetate. The combined organic layer was washed with brine, dried over magnesium sulfate, and concentrated in vacuo. The residue was purified by silica gel chromatography eluting 5-20% ethyl acetate in hexane to furnish (2S)-2-(4-(N-cyclohexyl-N-methylamino)phenyl)-4-((1R)-1-phenylethyl)morpholine (7.27 g, quant.) as a pale yellow oil.

(2S)-2-(4-(N-cyclohexyl-N-methylamino)phenyl)morpholine

A 300-ml flask containing a solution of (S)-2-(4-(N-cyclohexyl-N-methylamino)phenyl)-4-((R)-1-phenylethyl)morpholine (7.27 g, 19.07 mmol) and 10% palladium on carbon (3.0 g) in ethanol (30 ml) was charged with hydrogen. The reaction mixture was stirred vigorously at 50° C. for 10 hours. The catalyst was filtered off with a Celite pad, and the filtrate was concentrated under reduced pressure to yield (2S)-2-(4-(N-cyclohexyl-N-methylamino)phenyl)morpholine (4.95 g, 95%) as a clear oil.

2-((2S)-2-(4-(N-cyclohexyl-N-methylamino)phenyl)morpholin-4-yl)-3-methyl-6-(4-pyridvl)-pyrimidin-4-one To a solution of (2S)-2-(4-(N-cyclohexyl-N-methylamino)phenyl)morpholine (4.47 g, 16.30 mmol) and triethylamine (3.1 ml, 22.2 mmol) in tetrahydrofuran (50 ml) was added 2-chloro-3-methyl-6-(4-pyridyl)-3H-pyrimidin-4-one (3.28 g, 14.82 mmol) portionwise. Upon disappearance of the chloropyrimidone, the reaction mixture was condensed under reduced pressure. The residue was partitioned between 1 N sodium hydroxide and dichloromethane. The organic layer was washed with water, dried over anhydrous sodium sulfate, filtered, and concentrated under reduced pressure to give a pale yellow solid, which was recrystallized from ethanol to afford 2-((2S)-2-(4-(N-cyclohexyl-N-methylamino)-phenyl)morpholin-4-yl)-3-methyl-6-(4-pyridyl)-pyrimidin-4-one (5.15 g, 75.7%) as white crystals.

Example 4

3-Methyl-2-((2S)-2-(4-((pyridin-2-yl)amino)phenyl)morpholin-2-yl)-6-(pyridin-4-yl)-pyrimidin-4(3H)-one (Compound No. 48)

N-(4-((2S)-4-((1R)-1-Phenylethyl)morpholin-2-yl)phenyl)pyridin-2-amine

A solution of (2S)-2-(4-aminophenyl)-4-((1R)-1-phenylethyl)morpholine (1.5 g, 5.31 mmol), 2-chloropyridine (1.21 g, 10.6 mmol), tris(dibenzylideneacetone)-dipalladium(0) (52.6 mg, 0.05 mmol), potassium tert-butoxide (0.88 g, 7.8 mmol) and 1,3-bis(2,6-di-i-propylphenyl)imidazolium chloride (89.6 mg, 0.21 mmol) in dioxane (17 ml) was stirred at 90° C. for 15 hours. The solvent was removed under reduced pressure and the residue was partitioned between water and ethyl acetate. The organic layer was dried over anhydrous sodium sulfate and the solvent was evaporated under reduced pressure. The resulting residue was purified by column chromatography on silica gel (hexane-ethyl acetate, 1:2) to afford N-(4-((2S)-4-((1R)-1-Phenylethyl)-morpholin-2-yl)phenyl)pyridin-2-amine (0.68 g, 36%) as red crystals.

N-(4-((2S)-Morpholin-2-yl)phenyl)pyridin-2-amine

To a solution of N-(4-((2S)-4-((1R)-1-phenylethyl)morpholin-2-yl)phenyl)-pyridin-2-amine (0.89 g, 2.5 mmol) and ammonium formate (0.78 g, 12.5 mmol) in tetrahydrofuran (15ml)-methanol (24 ml)-water (18 ml) was added 10% palladium on carbon (wet, 200 mg) and the mixture was stirred at 95° C. for one hour. After filtration, the solvent was removed in vacuo and the residue was partitioned between water and dichloromethane. The organic layer was dried over anhydrous sodium sulfate and the solvent was concentrated under reduced pressure to yield N-(4-((2S)-Morpholin-2-yl)phenyl)pyridin-2-amine (0.60 g, 94%) as a yellow oil.

3-Methyl-2-((2S)-2-(4-((pyridin-2-yl)amino)phenyl)morpholin-4-yl)-6-(pyridin-4-yl)pyrimidin-4(3H)-one A solution of N-{4-[(2S)-morpholin-2-yl]phenyl}pyridin-2-amine (0.2 g, 0.78 mmol), 2-chloro-1-methyl-6-oxo-4-(pyridin-4-yl)-1,6-dihydropyrimidine (0.13 g, 0.62 mmol), and triethylamine (0.23 g, 2.3 mmol) in tetrahydrofuran (10 ml) was stirred at 95° C. for 3 hours. The solvent was removed under reduced pressure and the residue was partitioned between water and dichloromethane. The organic layer was dried over anhydrous sodium sulfate and the solvent was concentrated under reduced pressure. The resulting residue was purified by column chromatography on silica gel (chloroform-methanol, 10:1) to afford 3-Methyl-2-((2S)-2-(4-((pyridin-2-yl)amino)phenyl)morpholin-4-yl)-6-(pyridin-4-yl)-pyrimidin-4(3H)-one (100 mg, 37%) as a yellow oil.

Example 5

3-Methyl-2-((2S)-2-(4-(methyl(pyridin-2-yl)amino)phenyl)morpholin-4-yl)-6-(pyridin-4-yl)pyrimidin-4(3H)-one (Compound No. 72)

N-Methyl-N-(4-((2S)-4-((1R)-1-phenylethyl)morpholin-2-yl)phenyl)pyridin-2-amine

To a solution of N-(4-((2S)-4-((1R)-1-phenylethyl)morpholin-2-yl)phenyl)pyridin-2-amine (0.57 g, 1.5 mmol) and iodomethane (1.6 g, 11.2 mmol) in tetrahydrofuran (50 ml) was added potassium tert-butoxide (1.6 g, 9.45 mmol). After stirring at room temperature for 4 hours, water was added and the mixture was extracted with ethyl acetate. The organic layer was washed with brine, dried over anhydrous sodium sulfate, and evaporated. The crude product was purified by column chromatography on silica gel (hexane-ethyl acetate, 1:1) to afford N-Methyl-N-(4-((2S)-4-((1R)-1-phenylethyl)-morpholin-2-yl)phenyl)pyridin-2-amine (0.57 g, 81%) as a yellow oil.

N-Methyl-N-(4-((2S)-morpholin-2-yl)phenyl)pyridin-2-amine

To a solution of N-Methyl-N-(4-((2S)-4-((1R)-1-phenylethyl)morpholin-2-yl)-phenyl)pyridin-2-amine (0.57 g, 1.5 mmol) and ammonium formate (0.48 g, 7.6 mmol) in tetrahydrofuran (15 ml)-methanol (30 ml)-water (16 ml) was added 10% palladium on carbon (wet, 200 mg) and stirred at 95° C. for one hour. After filtration, the solvent was removed under reduced pressure and the residue was partitioned between water and dichloromethane. The organic layer was dried over anhydrous sodium sulfate and the solvent was concentrated under reduced pressure to give N-Methyl-N-(4-((2S)-morpholin-2-yl)phenyl)pyridin-2-amine (0.38 g, 94%) as a yellow oil.

3-Methyl-2-((2S)-2-(4-(methyl(pyridin-2-yl)amino)phenyl)morpholin-4-yl)-6-(pyridin-4-yl)pyrimidin-4(3H)-one A solution of N-Methyl-N-(4-((2S)-morpholin-2-yl)phenyl)pyridin-2-amine (0.12 g, 0.46 mmol), 2-chloro-1-methyl-6-oxo-4-(pyridin-4-yl)-1,6-dihydropyrimidine (0.08 g, 0.37 mmol), and triethylamine (0.23 g, 2.3 mmol) in tetrahydrofuran (10 ml) was stirred at 95° C. for 3 hours. The solvent was removed under reduced pressure and the residue was partitioned between water and dichloromethane. The organic layer was dried over anhydrous sodium sulfate and the solvent was concentrated under reduced pressure. The resulting residue was purified by column chromatography on silica gel (chloroform-methanol, 10:1) to give 3-Methyl-2-((2S)-2-(4-(methyl(pyridin-2-yl)amino)phenyl)morpholin-4-yl)-6-(pyridin-4-yl)-pyrimidin-4(3H)-one (65 mg, 13%) as a yellow oil.

Example 6

2-((2S)-2-(4-(N-methyl-N-((3R)-tetrahydrofuran-3yl)amino)phenyl)morpholin-4-yl)-3-methyl-6-(pyrimidin-4-yl)-3H-pyrimidin-4-one (Compound No. 091)

4-((1R)-1-phenylethyl)-(2S)-2-(4-(N-((3R)-tetrahydrofuran-3-yl)amino)phenyl)-morpholine (R)-(+)-3-Aminotetrahydrofuran toluene-4-sulfonate (2.0 g, 7.7 mmol) was added to a suspension of (2S)-2-(4-bromophenyl)-4-((1R)-1-phenylethyl)morpholine (2.4 g, 6.9 mmol), palladium acetate (65 mg, 0.29 mmol), 2-(di-t-butylphosphino)biphenyl (170 mg, 0.57 mmol), and sodium tert-butoxide (3.4 g, 35.4 mmol) in tert-butanol (50 ml) at room temperature. After heating at 90° C. for 6 hours, the resulting suspension was passed through a Celite column. The filtrate was concentrated under reduced pressure, and the residue was purified by silica gel chromatography eluting 5-10% methanol in chloroform to afford 4-((1R)-1-phenylethyl)-(2S)-2-(4-(N-((3R)-tetrahydrofuran-3-yl)amino)phenyl)morpholine (1.3 g, 53%) as white crystals.

$^1$H-NMR(CDCl$_3$) δ: 1.35 (3H, d, J=6.8 Hz), 2.04-2.16 (4H, m), 2.55-2.62 (1H, m), 3.08-3.12 (1H, m), 3.33-3.38 (1H, m), 3.67-3.93 (5H, m), 3.98-4.02 (1H, m), 4.46-4.58 (2H, m), 6.57 (2H, d, J=7.2 Hz), 6.83 (1H, d, J=9.0 Hz), 7.21-7.33 (7H, m)

(2S)-2-(4-(N-methyl-N-((3R)-tetrahydrofuran-3-yl)amino)phenyl)-4-((1R)-1-phenylethyl)morpholine Sodium triacetoxyborohydride (2.4 g, 11.3 mmol) was added to a solution of 4-((1R)-1-phenylethyl)-(2S)-2-(4-(N-

((3R)-tetrahydrofuran-3yl)amino)phenyl)morpholine (1.3 g, 3.69 mmol) and formalin (35%, 1.6 g, 18.6 mmol) in dichloroethane (50 mL) at room temperature. After stirring for 2 hours, the resulting suspension was partitioned between ethyl acetate and 1 N sodium hydroxide. The aqueous layer was extracted with ethyl acetate. The combined organic layer was washed with brine, dried over magnesium sulfate, and concentrated in vacuo. The residue was purified by silica gel chromatography eluting 5-10% methanol in chloroform to furnish (2S)-2-(4-(N-methyl-N-((3R)-tetrahydrofuran-3-yl)amino)phenyl)-4-((1R)-1-phenylethyl)morpholine (1.35 g, 100%) as a pale yellow oil.

$^1$H-NMR(CDCl$_3$) δ:1.33 (3H, d, J=6.8 Hz), 2.02-2.13(4H, m), 2.53-2.60 (1H, m), 3.00(3H, s),3.08-3.12 (1H, m), 3.30-3.34 (1H, m), 3.70-3.98 (5H, m), 4.00-4.06 (1H, m), 4.46-4.58 (2H, m), 6.60 (2H, d, J=7.2 Hz), 7.28-7.37 (7H, m)

(2S)-2-(4-(N-methyl-N-((3R)-tetrahydrofuran-3-yl)amino)phenyl)morpholine hydrochloride A solution of 10% palladium on carbon (1.0 g) and ((2S)-2-(4-(N-methyl-N-((3R)-tetrahydrofuran-3yl) amino)phenyl)-4-((1R)-1-phenylethyl)morpholine (3.69 mmol) in methanol (10 ml) was stirred under hydrogen atmosphere vigorously at 50° C. for 10 hours. The catalyst was filtered off with a Celite pad, and the filtrate was concentrated under reduced pressure. The residue was treated with 4N hydrogen chloride in ethyl acetate and concentrated under reduced pressure to give a pale yellow solid, which was recrystallized from ethanol to afford (2S)-2-(4-(N-methyl-N-((3R)-tetrahydrofuran-3yl)amino)phenyl)morpholine hydrochloride (0.9 g, 73%) as white crystals.

$^1$H-NMR(DMSO-d6) δ:2.99 (3H, s), 3.00-3.12 (2H, m), 3.23-3.28 (1H, m), 3.61-4.02 (9H, m), 4.51-4.53 (1H, m), 4.79 (1H, d, J=10.1 Hz), 7.42-7.48 (4H ,m), 9.63 (2H, br)

2-((2S)-2-(4-(N-methyl-N-((3R)-tetrahydrofuran-3-yl)amino)phenyl)morpholin-4-yl)-3-methyl-6-(pyrimidin-4-yl)-3H-pyrimidin-4-one A solution of 2-chloro-3-methyl-6-(4-pyrimidin-4-yl)-3H-pyrimidin-4-one (0.24 g, 1.08 mmol), (2S)-2-(4-(N-methyl-N-((3R)-tetrahydrofuran-3yl)amino)phenyl) morpholine hydrochloride (0.4 g, 1.19 mmol) and triethylamine (0.6 g, 5.93 mmol) in tetrahydrofuran (20 ml) was stirred for 15 hours at room temperature. The mixture was partitioned between water and chloroform, and the organic layer was washed with brine, dried over magnesium sulfate, and concentrated in vacuo. The residue was purified by silica gel column chromatography eluting 5-10% methanol in chloroform to furnish (2-((2S)-2-(4-(N-methyl-N-((3R)-tetrahydrofuran-3-yl)amino)phenyl)-morpholin-4-yl)-3-methyl-6-(pyrimidin-4-yl)-pyrimidin-4-one (0.23 g, 47%) as pale yellow crystals.

Example 7

2-((2S)-2-(4-(3-(pyrrolidin-1-yl)propyloxy)phenyl)morpholine-4-yl)-3-methyl-6-(pyrimidin-4-yl)-pyrimidin-4-one (Compound No. 202)

2-Bromo-1-(4-hydroxyphenyl)-ethan-1-one

Phenyltrimethylammonium tribromide (276 g, 734 mmol) was added to a suspension of 4-hydroxyacetophenone (100 g, 734 mmol) in tetrahydrofuran (1000 ml) at room temperature. After stirring for 3 hours, the resulting suspension was filtered, and the filtrate was concentrated under reduced pressure. The residue was washed with diisopropyl ether to afford 2-bromo-1-(4-hydroxyphenyl)-ethan-1-one (85 g, 54%) as white crystals.

$^1$H-NMR(CDCl$_3$) δ: 3.84 (1H, br), 4.40 (2H, s), 6.98 (2H, d, J=7.2 Hz), 7.91 (2H, d, J=7.2 Hz)

4-(2-Bromoacetyl)phenyl methanesulfonate

Methanesulfonyl chloride (50 g, 436 mmol) was added to a solution of 2-bromo-1-(4-hydroxyphenyl)-ethan-1-one (85 g, 395 mmol) and triethylamine (48 g, 474 mmol in tetrahydrofuran (1000 ml) at 0° C. and the mixture was stirred for 30 minutes at room temperature. The mixture was partitioned between water and ethyl acetate, and the organic layer was washed with brine, dried over magnesium sulfate. The solvent was evaporated under reduced pressure and the residue was washed with diisopropyl ether to afford 4-(2-bromoacetyl)phenyl methanesulfonate (96 g, 83%) as white crystals.

$^1$H-NMR(CDCl$_3$) δ: 3.22 (3H, s), 4.41 (2H, s), 7.41 (2H, d, J=7.2 Hz), 8.06 (2H, d, J=7.2 Hz)

4-((2S)-2-Bromo-1-hydroxyethyl)phenyl methanesulfonate

Borane-tetrahydrofuran complex (1.0 M solution in tetrahydrofuran, 330 ml) was added to a solution of (S)-CBS ((S)-2-Methyl-CBS-oxazaborolidine, 50 ml, 1.0 M solution in toluene) at −30° C. over 15 minutes and the solution was stirred for 30 minutes. 4-(2-Bromoacetyl)phenyl methanesulfonate (96 g, 328 mmol) in tetrahydrofuran (500 ml) was dropped over 70 minutes keeping the temperature −32 to −28° C. After stirring for one hour, the solution was warmed to room temperature, and methanol (10 ml) was added slowly and then 0.5 M hydrochloric acid (300 ml) was dropped over 10 minutes. The solution was filtered after 40 minutes stirring and filtrate was extracted with ethyl acetate. The combined organic layer was washed with 0.5 M hydrochloric acid, 0.1M aqueous sodium hydroxide, and brine and dried over anhydrous sodium sulfate. Concentration of the organic layer yielded 4-((2S)-2-bromo-1-hydroxyethyl)phenyl methanesulfonate as a pale brown oil.

$^1$H-NMR(CDCl$_3$) δ: 2.72 (1H, d, J=1.2 Hz), 3.10 (3H, s), 3.44-3.58 (2H, m), 4.93-4.97 (1H, m), 7.30 (2H, d, J=7.2 Hz), 7.46 (2H, d, J=7.2 Hz)

4-((S)-Oxiranyl)phenyl methane sulfonate

An aqueous sodium hydroxide (1M, 600 ml) was added to 4-((2S)-2-bromo-1-hydroxyethyl)phenyl methanesulfonate (328 mmol) in diethyl ether (400 ml) and the solution was stirred at room temperature for 5 hours. The organic layer was separated and the aqueous layer was extracted with ethyl acetate. Combined organic layer was washed with brine and dried over anhydrous sodium sulfate. The solvent was evaporated under reduced pressure and the residue was washed with diisopropyl ether to afford 4-((S)-oxiranyl)phenyl methanesulfonate (69 g, 98%) as white crystals.

$^1$H-NMR(CDCl$_3$) ε: 2.75 (1H, dd, J=1.2 Hz, 6.8 Hz), 3.14-3.16 (4H, m), 3.88 (1H, dd, J=1.2 Hz, 7.2 Hz), 7.28 (2H, d, J=7.2 Hz), 7.42 (2H, d, J=7.2 Hz)

4-((1S)-2-benzylamino-1-hydroxyethyl)phenyl methanesulfonate

A mixture of 4-((S)-oxiranyl)phenyl methanesulfonate (69 g, 322 mmol) and benzylamine (104 g, 971 mmol) was heated at 80° C. for 3 hours. An excess benzylamine was evaporated under reduced pressure and the residue was washed with diisopropyl ether to afford 4-((1S)-2-benzylamino-1-hydroxyethyl)phenyl methanesulfonate (71.0 g, 69%) as white crystals.

$^1$H-NMR(CDCl$_3$) δ: 2.68-2.72 (1H, m), 2.96 (1H, dd, J=4.8 Hz, 10.2 Hz), 3.12 (3H, s), 3.84 (2H, d, J=1.2 Hz), 4.72 (1H, dd, J=1.2 Hz, 10.2Hz), 7.23-7.43 (9H, m)

4-((2S)-4-Benzyl-5-oxo-morpholin-2-yl)phenyl methanesulfonate

Chloroacetyl chloride (27.5 g, 243 mmol) was dropped to a solution of 4-((1S)-2-benzylamino-1-hydroxyethyl)phenyl methanesulfonate (71 g, 221 mmol) in 1N aqueous sodium hydroxide (330 ml) and stirred for one hour at room temperature. Resulting solution was extracted with chloroform, and dried over anhydrous sodium sulfate. The solvent was removed under reduced pressure. Potassium hydroxide (85%, 17.5 g, 265 mmol) was added to a solution of the resulting pale brown oil in 2-propanol (600 ml), and the mixture was stirred for 10 hours. The solvent was removed in vacuo and the residue was partitioned between water and chloroform. The organic layer was washed with 0.5 M hydrochloric acid, saturated sodium hydrogen carbonate, brine and dried over anhydrous magnesium sulfate. Removal of the solvent under reduced pressure furnished 4-((2S)-4-benzyl-5-oxo-morpholin-2-yl)phenyl methanesulfonate (79.8 g, 100%) as a brown oil.

$^1$H-NMR(CDCl$_3$) δ: 3.13 (3H, s), 3.29-3.36 (2H, m), 4.36-4.46 (4H, m), 4.81 (1H, dd, J=1.2 Hz, 10 Hz), 7.24-7.42 (9H, m)

(2S)-4-Benzyl-2-(4-hydroxyphenyl)morpholine

Chlorotrimethylsilane (96 g, 884 mmol) was added to a solution of lithium borohydride (9.6 g, 441 mmol) in tetrahydrofuran (500 ml) and stirred for one hour at room temperature. A solution of 4-((2S)-4-benzyl-5-oxo-morpholin-2-yl) phenyl methanesulfonate (79.8 g, 221 mmol) in tetrahydrofuran (200 ml) was added to the solution and stirred at room temperature for one hour. After careful addition of methanol (60 ml) under ice-cooling, the solvent was removed under reduced pressure. Potassium hydroxide (145 g, 2.2 mol) was added to a solution of the residue in ethanol (300 ml) and water (300 ml) and the mixture was stirred at 80° C. for 2 hours. The solvent was removed under reduced pressure and the residue was extracted with ethyl acetate and dried over anhydrous magnesium sulfate. Removal of the solvent yielded (2S)-4-benzyl-2-(4-hydroxyphenyl)morpholine (39.8 g, 67%) as white crystals.

$^1$H-NMR(CDCl$_3$) δ: 2.05-2.31 (2H, m), 2.72-2.89 (2H, m), 3.54 (2H, s), 3.81-3.86 (1H, m), 3.96-4.00 (1H, m), 4.50 (1H, dd, J=1.2 Hz, 10.2 Hz), 5.12 (1H, br), 6.75 (2H, d, 7.2 Hz), 7.19-1.32 (7H, m)

tert-Butyl(2S)-2-(4-Hydroxyphenyl)morpholine-4-carboxylate

A solution of 10% palladium on carbon (1.0 g) and (2S)-4-benzyl-2-(4-hydroxyphenyl)morpholine (10 g, 37.1 mmol) in methanol (100 ml) was stirred under hydrogen atmosphere vigorously at 50° C. for 10 hours. The catalyst was filtered off with a Celite pad, and the filtrate was concentrated under reduced pressure. Di-tert-butyldicarbonate (9.7 g, 44.4 mmol) was added to a solution of the residue in 1N aqueous sodium hydroxide (200 ml) at 0° C. and the mixture was stirred for one hour at room temperature. The mixture was partitioned between water and ethyl acetate. The organic layer was washed with brine, dried over magnesium sulfate, and concentrated in vacuo. The residue was purified by silica gel chromatography eluting 5-10% methanol in chloroform to furnish tert-butyl (2S)-2-(4-hydroxyphenyl)morpholine-4-carboxylate (8.6 g, 83%) as white crystals.

$^1$H-NMR(CDCl$_3$) δ: 1.48 (9H, s), 2.80-3.07 (2H, m), 3.62-3.70 (1H, m), 3.86-4.02 (3H, m), 4.33 (1H, dd, J=1.2 Hz, 10.2 Hz), 5.72 (1H, br), 6.81 (2H, d, J=7.2 Hz), 7.22 (2H, d, J=7.2 Hz)

tert-Butyl (2S)-2-(4-(3-bromopropyloxy)phenyl) morpholine-4-carboxylate

Diisopropyl azodicarboxylate (40% in toluene, 13.6 g, 26.9 mmol) was added to a solution of tert-butyl (2S)-2-(4-hydroxyphenyl)morpholine-4-carboxylate (5.0 g, 17.9 mmol), triphenylphosphine (7.1 g, 27.1 mmol) and 3-bromopropanol (3.75 g, 27.0 mmol) in tetrahydrofuran (100 ml) and the solution was stirred for 10 hours at room temperature. The mixture was partitioned between water and ethyl acetate. The organic layer was washed with brine, dried over magnesium sulfate and concentrated in vacuo. The residue was purified by silica gel chromatography eluting 5-10% methanol in chloroform to furnish tert-butyl (2S)-2-(4-(3-bromopropyloxy)phenyl)morpholine-4-carboxylate (7.16 g, 100%) as a colorless oil.

$^1$H-NMR(CDCl$_3$) δ: 1.48 (9H, s), 2.29-2.35 (2H, m), 2.83-3.08 (2H, m), 3.58-3.70 (3H, m), 3.98-4.13 (5H, m), 4.36 (1H, d, J=1.2 Hz, 10.2 Hz), 6.90 (2H, d, J=7.2 Hz), 7.28 (2H, d, J=7.2 Hz)

tert-Butyl (2S)-2-(4-(3-(pyrrolidin-1-yl)propvloxy) phenyl)morpholine-4-carboxylate tert-Butyl (2S)-2-(4-(3-bromopropyloxy)phenyl)morpholine-4-carboxylate (2.0 g, 5.0 mmol) was added to a solution of sodium hydride (60% in oil, 0.22 g, 5.50 mmol) and pyrrolidine (0.43 g, 6.05 mmol) in tetrahydrofuran (40 ml) at room temperature and the mixture was stirred at 80° C. for 5 hours. The mixture was partitioned between water and chloroform. The organic layer was washed with brine, dried over magnesium sulfate and concentrated in vacuo. The residue was purified by silica gel column chromatography eluting 5-10% methanol in chloroform to furnish tert-butyl (2S)-2-(4-(3-(pyrrolidin-1-yl)propyloxy)phenyl)morpholine-4-carboxylate (1.13 g, 58%) as a colorless oil.

$^1$H-NMR(CDCl$_3$) δ: 1.48 (9H, s), 1.78-1.82 (4H, m), 1.99-2.03 (2H, m), 2.53-2.67 (6H, m), 2.80-3.06 (2H, m), 3.62-3.68 (1H, m), 3.97-4.05 (5H, m), 4.36 (1H, dd, J=1.2 Hz, 10.2 Hz), 6.88 (2H, d, J–7.2 Hz), 7.26 (2H, d, J=7.2 Hz)

(2S)-2-(4-(3-(pyrrolidin-1-yl)propyloxy)phenyl)morpholine hydrochloride

Hydrogen chloride in ethyl acetate solution (4N) was added to a solution of tert-butyl (2S)-2-(4-(3-(pyrrolidin-1-yl)propyloxy)phenyl)morpholine-4-carboxylate (1.13 g, 2.89 mmol) in methanol. The mixture was stirred for one hour at room temperature and the solvent was evaporated under reduced pressure to give a white solid, which was recrystallized from ethanol to afford (2S)-2-(4-(3-(pyrrolidin-1-yl) propyloxy)phenyl)morpholine hydrochloride (0.9 g, 86%) as white crystals.

$^1$H-NMR(DMSO-d6) δ: 1.88-2.18 (6H, m), 2.96-3.02 (4H, m), 3.01-3.22 (4H, m), 3.51-3.54 (2H, m), 3.91-3.96 (1H, m), 4.05-4.09 (3H, m), 4.74 (1H, dd, J=1.2 Hz, 10.2 Hz), 6.94 (2H, d, J=7.2 Hz), 7.30 (2H, d, J=7.2 Hz), 9.60 (2H, br), 10.94 (1H, br)

2-((2S)-2-(4-(3-(pyrrolidin-1-yl)propyloxy)phenyl)morpholine-4-yl)-3-methyl-6-(pyrimidin-4-yl)-3H-pyrimidin-4-one A solution of 2-chloro-3-methyl-6-(4-pyrimidin-4-yl)-3H-pyrimidin-4-one (0.15 g, 0.67 mmol), (2S)-2-(4-(3-(pyrrolidin-1-yl)propyloxy)phenyl)morpholine hydrochloride (0.25 g, 0.69 mmol) and triethylamine (0.42 g, 4.15 mmol) in tetrahydrofuran (10 ml) was stirred for 15 hours at room temperature. The mixture was partitioned between water and chloroform. The organic layer was washed with brine, dried over magnesium sulfate and concentrated in vacuo. The residue was purified by silica gel column chromatography eluting 5-10% methanol in chloroform to furnish 2-((2S)-2-(4-(3-(pyrrolidin-1-yl)propyloxy)phenyl)morpholine-4-yl)-3-methyl-6-(pyrimidin-4-yl)-pyrimidin-4-one (90 mg, 28%) as white crystals.

Example 8

N-(2-hydroxy-ethyl)-4-[(2S)-4-(1-methyl-6-oxo-4-pyridin-4-yl-1,6-dihydro-pyrimidin-2-yl)-morpholin-2-yl]-benzamide (Compound No. 209)

4-[(2S)-4-((1R)-1-phenyl-ethy)-morpholin-2-yl]-benzoic acid

To a suspension of (2S)-2-(4-bromophenyl)-4-((1R)-1-phenylethyl)morpholine (3.46 g, 10.0 mmol) in tetrahydrofuran (80 ml) was added n-butyllithium (7.7 ml, 12.0 mmol, 1.56 M in hexane) at −78° C. After stirring the mixture for 10 minutes, excess of dry ice was added to the mixture and the reaction mixture was maintained at −78° C. for 1.5 hours and then partitioned between diethyl ether and 0.2 N aqueous sodium hydroxide. The aqueous layer was washed with diethyl ether and neutralized with 1N hydrochloric acid. The resulting aqueous layer was extracted with ethyl acetate. The organic layer was washed with brine, dried over sodium sulfate and concentrated in vacuo. Filtration of the precipitate gave 4-[(2S)-4-((1R)-1-phenyl-ethy)-morpholin-2-yl]-benzoic acid (3.05 g, 98%) as white crystals.

$^1$H-NMR(CDCl$_3$) δ: 1.39(3H, d, J=6.9 Hz), 2.10-2.18(2H, m), 2.63(1H,m), 3.15(1H, m), 3.41(1H, q, J=6.9 Hz), 3.78 (1H, m), 3.93(1H, m), 4.55(1H, dd, J=10.2, 2.1 Hz), 7.25-7.39(5H,m), 7.47(2H, d, J=8.4 Hz), 8.07(2H, d, J=8.4 Hz).

N-(2-hydroxy-ethyl)-4-[(2S)-4-((1R)-1-phenyl-ethy)-morpholin-2-yl]-benzamide 1,1'-Carbonyldiimidazole (540 mg, 3.30 mmol) was added to a solution of 4-[(2S)-4-((1R)-1-phenyl-ethy)-morpholin-2-yl]-benzoic acid (944 mg, 3.03 mmol) in dichloromethane at 0° C. After stirring for 2 hours, ethanolamine (0.36 ml, 6.0 mmol) was added to the reaction mixture and the mixture was stirred over night. The resulting suspension was concentrated in vacuo and the residue was purified by silica gel chromatography (ethyl acetate-hexane) to afford N-(2-hydroxy-ethyl)-4-[(2S)-4-((1R)-1-phenyl-ethy)-morpholin-2-yl]-benzamide (789 mg, 73%.) as a colorless oil.

$^1$H-NMR(CDCl$_3$) δ: 1.36(3H, d, J=6.9 Hz), 2.10-2.15(2H, m), 2.61(1H, dd, J=11.7, 1.5 Hz), 3.11(1H,m), 3.36(1H, q, J=6.9 Hz), 3.59-3.64(2H, m), 3.73-3.77(1H, m), 3.78-3.83 (2H, m), 3.84-3.91(1H, m), 4.63(1H, dd, J=10.2, 2.4 Hz), 7.26-7.39(2H,m), 7.41(2H, d, J=8.4 Hz), 7.65(3H,m), 7.75 (2H, d, J=8.4 Hz).

N-(2-hydroxy-ethyl)-[(2S)-4-morpholin-2-yl]-benzamide

A solution of N-(2-hydroxy-ethyl)-4-[(2S)-4-((1R)-1-phenyl-ethy)-morpholin-2-yl]-benzamide (789 mg, 2.20 mmol) and 20% palladium hydroxide on carbon (0.30 g) in ethanol (6.0 ml) was stirred under hydrogen atmosphere for 10 hours at room temperature. The mixture was filtered through celite and the filtrate was concentrated under reduced pressure to yield N-(2-hydroxy-ethyl)-[(2S)-4-morpholin-2-yl]-benzamide (550 mg, 100%) as a clear oil.

$^1$H-NMR(CD$_3$OD) δ: 2.80(1H, dd, J=12.6, 11.1 Hz), 3.02-3.06(1H,m), 3.16-3.21(1H, m), 3.51(2H, d, J=5.7 Hz), 3.72 (2H, d, J=5.7 Hz), 3.80-3.97(1H, m), 4.08-4.12(1H, m), 4.65 (1H, dd, J=10.8, 2.4 Hz), 7.46(2H, d, J=8.4 Hz), 7.84(2H, d, J=8.4 Hz).

N-(2-hydroxy-ethyl)-4-[(2S)-4-(1-methyl-6-oxo-4-pyridin-4-yl-1,6-dihydro-pyrimidin-2-yl)-morpholin-2-yl]-benzamide A solution of N-(2-hydroxy-ethyl)-[(2S)-4-morpholin-2-yl]-benzamide (190 mg, 0.76 mmol), 2-chloro-3-methyl-6-(4-pyridyl)-pyrimidine-4-one (111 mg, 0.50 mmol) and triethylamine (0.28 ml, 2.0 mmol) in tetrahydrofuran (6.0 ml) was stirred at room temperature for 6 hours. The reaction mixture was evaporated in vacuo and the residue was partitioned between dichloromethane and water. The whole was extracted with dichloromethane. The organic layer was washed with water, dried and concentrated in vacuo. Washing the precipitate with diethyl ether and dichloromethane gave N-(2-hydroxy-ethyl)-4-[(2S)-4-(1-methyl-6-oxo-4-pyridin-4-yl-1,6-dihydro-pyrimidin-2-yl)-morpholin-2-yl]-benzamide (90.8 mg, 42%) as white crystals.

Example 9

N-(2-hydroxy-ethyl)-4-[(2S)-4-(1-methyl-6-oxo-1,6-dihydro-[4,4']bipyrimidinyl-2-yl)-morpholin-2-yl]-benzamide (Compound No. 210)

A solution of N-(2-hydroxy-ethyl)-[(2S)-4-morpholin-2-yl]-benzamide (190 mg, 0.76 mmol), 2-chloro-3-methyl-6-(4-pyrimidyl)-pyrimidine-4-one (111 mg, 0.50 mmol) and triethylamine (0.28 m, 2.0 mmol) in tetrahydrofuran (6 ml) was stirred at room temperature for 6 hours. The reaction mixture was evaporated in vacuo and the residue was partitioned between dichloromethane and water. The whole was extracted with dichloromethane. The organic layer was washed with water, dried and concentrated in vacuo. Purification of the residue by preparative high performance liquid chromatography gave N-(2-hydroxy-ethyl)-4-[(2S)-4-(1-methyl-6-oxo-4-pyridin-4-yl-1,6-dihydro-pyrimidin-2-yl)-morpholin-2-yl]-benzamide (49.8 mg, 23%) as white crystals.

Example 10

N$^2$,N$^2$-Dimethyl-N$^1$-{4-[(2S)-4-(1-methyl-6-oxo-1,6-dihydro-4,4'-bipyrimidin-2-yl)morpholin-2-yl]phenyl}glycinamide (Compound No. 220)

2-Chloro-N-{4-[(2S)-4-((1R)-1-phenylethyl)morpholin-2-yl]phenyl}acetamide

To a solution of (2S)-2-(4-aminophenyl)-4-((1R)-1-phenylethyl)morpholine (2.93 g, 10 mmol) and triethylamine (3.0 g, 30 mmol) in tetrahydrofuran (50 ml) was added chloroacetyl chloride (2.26 g, 20 mmol). The mixture was stirred at room temperature for 2 hours and partitioned between water and chloroform. The organic extract was washed with brine and dried over anhydrous sodium sulfate. The solvent was removed under reduced pressure and the precipitated crystals were collected by filtration, washed with isopropyl ether to give 2-chloro-N-{4-[(2S)-4-((1R)-1-phenylethyl)morpholin-2-yl]phenyl}acetamide (3.5 g, 97%) as yellow crystals.

$^1$H-NMR(CDCl$_3$) δ: 1.35 (3H, d, J=6.6 Hz), 2.02-2.17 (2H, m), 2.60 (1H, d, J=11.1 Hz), 3.08 (1H, d, J=11.1 Hz), 3.36 (1H, q, J=6.9 Hz), 3.75 (1H, td, J=11.4 Hz, 2.4 Hz), 3.91 (1H, dd, J=9.9 Hz, 1.5 Hz), 4.19 (2H, s), 4.57 (1H, dd, J=10.2 Hz, 2.1Hz), 7.23-7.32 (5H, m), 7.36 (2H, d, J=8.4 Hz), 7.51 (2H, d, J=8.1 Hz), 8.21 (1H, br.s).

N$^2$,N$^2$-Dimethyl-N$^1$-{4-[(2S)-4-((1R)-1-phenylethyl)morpholin-2-yl]phenyl}glycinamide A solution of 2-chloro-N-{4-[(2S)-4-((1R)-1-phenylethyl)morpholin-2-yl]phenyl}acetamide (0.9 g, 2.5 mmol), potassium carbonate (1.72 g, 12.5 mmol), and dimethylamine hydrochloride (1.00 g, 12.5 mmol) in tetrahydrofuran (40 ml) and acetonitrile (80 ml) was stirred at 95° C. for 10 hours. After filtration, the solvent was removed in vacuo and the residue was partitioned between water and dichloromethane. The organic layer was dried over anhydrous sodium sulfate and the solvent was evaporated under reduced pressure to give N$^2$,N$^2$-dimethyl-N$^1$-{4-[(2S)-4-((1R)-1-phenylethyl)morpholin-2-yl]phenyl}glycinamide (1.15 g, quant.) as a yellow oil.

$^1$H-NMR(CDCl$_3$) δ: 1.35 (3H, d, J=6.6 Hz), 2.05-2.13 (2H, m), 2.38 (6H, s), 2.57 (1H, m), 3.07 (2H, s), 3.10 (1H, m), 3.35 (1H, q, J=6.6 Hz), 3.72 (1H, m), 3.90 (1H, m), 4.56 (1H, dd, J=10.2 Hz, 2.1 Hz), 7.20-7.39 (7H, m), 7.56 (2H, d, J=8.4 Hz), 9.90 (1H, br.s).

N$^2$,N$^2$-Dimethyl-N$^1$-{4-[(2S)-morpholin-2-yl]phenyl}glycinamide

To a solution of N$^2$,N$^2$-dimethyl-N$^1$-{4-[(2S)-4-((1R)-1-phenylethyl)morpholin-2-yl]phenyl}glycinamide (0.91 g, 2.5 mmol) and ammonium formate (0.79 g, 12.5 mmol) in tetrahydrofuran (20 ml), methanol (40 ml) and water (7 ml) was added 10% palladium on carbon (wet, 300 mg) and the mixture was stirred at 95° C. for 3 hours. After filtration, the solvent was removed in vacuo and the residue was partitioned between water and dichloromethane. The organic layer was dried over anhydrous sodium sulfate and the solvent was evaporated under reduced pressure to give N$^2$,N$^2$-dimethyl-N$^1$-{4-[(2S)-morpholin-2-yl]phenyl}glycinamide (0.63 g, 96%) a colorless oil.

$^1$H-NMR(CDCl$_3$) δ: 2.05-2.13 (2H, m), 2.38 (6H, s), 2.57 (1H, m), 3.07 (2H, s), 3.10 (1H, m), 3.72 (1H, m), 3.90 (1H, m), 4.56 (1H, dd, J=10.2 Hz, 2.1 Hz), 7.35 (2H, d, J=8.4 Hz), 7.56 (2H, d, J=8.4 Hz), 9.90 (1H, br.s).

N$^2$,N$^2$-Dimethyl-N$^1$-{4-[(2S)-4-(1-methyl-6-oxo-1,6-dihydro-4,4'-bipyrimidin-2-yl)morpholin-2-yl]phenyl}glycinamide A solution of N$^2$,N$^2$-dimethyl-N$^1$-{4-[(2S)-morpholin-2-yl]phenyl}glycinamide (0.21 g, 0.8 mmol), 2-chloro-1,6-dihydro-1-methyl-6-oxo-4'4-bipyrimidine (0.14 g, 0.64 mmol), and triethylamine (0.40 g, 4 mmol) in tetrahydrofuran (10 ml) was stirred at 95° C. for one hour. The solvent was removed in vacuo and the residue was partitioned between water and dichloromethane. The organic layer was dried over anhydrous sodium sulfate and the solvent was removed under reduced pressure. The resulting residue was purified by column chromatography on silica gel (chloroform/methanol=10/1) to afford N$^2$,N$^2$-dimethyl-N$^1$-{4-[(2S)-4-(1-methyl-6-oxo-1,6-dihydro-4,4'-bipyrimidin-2-yl)morpholin-2-yl]phenyl}glycinamide (0.17 g, 47%) as white crystals.

Example 11

Methyl (4-((2S)-4-(3-methyl-4-oxo-6-(pyridin-4-yl)-3H-pyrimidin-2-yl)morpholin-2-yl)-phenyl)carbamate(Compound No. 231)

4-((2S)-Morpholin-2-yl)phenylamine

To a solution of (2S)-2-(4-aminophenyl)-4-((1R)-1-phenylethyl)morpholine (17.45 g, 61.8 mmol) and ammonium formate (11.7 g, 185.4 mmol) in mixture of tetrahydrofuran (180 ml), methanol (180 ml) and water (45 ml) was added 10% palladium on carbon (wet, 1.8 g) and the mixture was stirred at 95° C. for 3 hours. After filtration, the solvent was removed in vacuo and the residue was partitioned between water and dichloromethane. The organic layer was dried over anhydrous sodium sulfate and the solvent was evaporated under reduced pressure to give 4-((2S)-morpholin-2-yl)phenylamine (10.45 g, 95%) as pale yellow crystals.

$^1$H-NMR(CDCl$_3$) δ: 2.46-2.50 (2H, m), 2.68 (2H, d, J=5.8 Hz), 2.76 (1H, d, J=12.2 Hz), 3.52 (1H, m), 3.79 (1H, d, J=10.9 Hz), 4.13 (1H, d, J=9.7 Hz), 4.95 (2H, br.s), 6.49 (2H, d, J=8.1 Hz), 6.94 (2H, d, J=8.1 Hz).

2-[(2S)-2-(4-Aminophenyl)morpholin-4-yl]-3-methyl-6-(pyridin-4-yl)-pyrimidin-4(3H)-one A solution of 4-((2S)-morpholin-2-yl)phenylamine (0.17 g, 0.95 mmol), 2-chloro-3-methyl-4-oxo-6-(pyridin-4-yl)-3,4-dihydropyrimidine (0.17 g, 0.76 mmol), and triethylamine (0.25 g, 2.85 mmol) in tetrahydrofuran (10 ml) was stirred at 95° C. for one hour. The solvent was removed in vacuo and the residue was partitioned between water and dichloromethane. The organic layer was dried over anhydrous sodium sulfate and the solvent was removed under reduced pressure. The resulting residue was purified by silica gel column chromatography (chloroform/methanol=10/1) to afford 2-[(2S)-2-(4-aminophenyl)morpholin-4-yl]-3-methyl-6-(pyridin-4-yl)-pyrimidin-4(3H)-one (0.15 g, 54%) as pale yellow crystals.

Methyl chloroformate (0.13 g, 1.38 mmol) was added to a solution of 2-((2S)-2-(4-aminophenyl)morpholine-4-yl)-3-methyl-6-(pyridin-4-yl)-3H-pyrimidin-4-one (0.45 g, 1.24 mmol) and triethylamine (0.25 g, 2.47 mmol) in tetrahydrofuran (20 ml) and stirred for one hour at room temperature. The mixture was partitioned between water and chloroform. The organic layer was washed with brine, dried over magnesium sulfate and concentrated in vacuo. The residue was purified by silica gel column chromatography eluting 5-10% methanol in chloroform to furnish methyl (4-((2S)-4-(3-methyl-4-oxo-6-(pyridin-4-yl)-3H-pyrimidin-2-yl)morpholin-2-yl)carbamate (0.35 g, 67%) as white crystals.

Example 12

1,1-Dimethyl-3-{4-[4-(1-methyl-6-oxo-4-pyridin-4-yl-1,6-dihydro-pyrimidin-2-yl)-morpholin-2-yl]-phenyl}-urea (Compound No. 237)

N,N-Dimethylcarbamoyl chloride (0.24 g, 2.23 mmol) was added to a solution of 2-[(2S)-2-(4-aminophenyl)morpholin-4-yl]-3-methyl-6-(pyridin-4-yl)-pyrimidin-4(3H)-one (0.40 g, 1.10 mmol) and triethylamine (1.1 g, 10.9 mmol) in tetrahydrofuran (20 ml) and the solution was stirred at 50° C. for 48 hours. The mixture was partitioned between water and chloroform. The organic layer was washed with brine, dried over magnesium sulfate and concentrated in vacuo. The residue was purified by silica gel chromatography eluting 5-10% methanol in chloroform to furnish 1,1-Dimethyl-3-{4-[4-(1-methyl-6-oxo-4-pyridin-4-yl-1,6-dihydro-pyrimidin-2-yl)morpholin-2-yl]-phenyl}-urea (0.14 g, 30%) as white crystals.

The compounds in the following table were prepared in the same manner as the methods described above. The compound numbers in the following table correspond to those shown in the above-described table of preferred compounds.

TABLE 4

| Compound No. | $^1$H-NMR δ: | LC-MS (M + 1) |
|---|---|---|
| 1 | 1.48 (9H, s), 309-3.17 (5H, m), 3.30 (1H, m), 3.57-3.62 (9H, m), 3.98 (1H, td, J = 2.4, 10.8 Hz), 4.14 (1H, dd, J = 1.8, 10.8 Hz), 4.65 (1H, dd, J = 2.4, 10.8 Hz), 6.94 (2H, d, J = 9.0 Hz), 7.26-7.41 (3H, m), 8.14 (1H, dd, J = 1.2, 4.8 Hz), 8.85 (1H, d, J = 5.1 Hz), 9.27 (1H, d, J = 1.2 Hz) (CDCl$_3$) | 534 |
| 2 | 2.19 (2H, quintet, J = 7.1 Hz), 2.64 (2H, t, J = 7.1 Hz), 3.11 (1H, dd, J = 10.5, 12.9 Hz), 3.30 (1H, td, J = 11.6, 2.1 Hz), 3.55 (1H, d, J = 11.6 Hz), 3.58 (3H, s), 3.64 (1H, d, J = 12.9 Hz), 3.89 (2H, t, J = 7.1 Hz), 4.00 (1H, td, J = 11.6, 2.1 Hz), 4.19 (1H, dd, J = 11.6, 2.1 Hz), 4.73 (1H, dd, J = 10.5, 2.1 Hz), 6.71 (1H, s), 7.42 (2H, d, J = 8.4 Hz), 7.66 (2H, d, J = 8.4 Hz), 7.80 (2H, d, J = 5.1 Hz), 8.74 (2H, br s) (CDCl$_3$) | |
| 3 | 2.19 (2H, quintet, J = 7.0 Hz), 2.63 (2H, t, J = 7.0 Hz), 3.10 (1H, dd, J = 13.0, 10.8 Hz), 3.27 (1H, td, J = 12.7, 2.3 Hz), 3.53 (1H, d, J = 12.7 Hz), 3.58 (3H, s), 3.63 (1H, d, J = 13.0 Hz), 3.88 (2H, t, J = 7.0 Hz), 4.00 (1H, td, J = 12.7, 2.3 Hz), 4.18 (1H, d, J = 12.7 Hz), 4.72 (1H, d, J = 10.8 Hz), 7.35 (1H, s), 7.43 (2H, d, J = 8.6 Hz), 7.66 (2H, d, J = 8.6 Hz), 8.14 (1H, d, J = 5.1 Hz), 8.87 (1H, d, J = 5.1 Hz), 9.27 (1H, s) (CDCl$_3$) | |
| 4 | 2.29 (3H, s), 3.01-3.05 (4H, m), 3.12 (1H, dd, J = 10.8, 12.9 Hz), 3.21-3.23 (5H, m), 3.58 (3H, s), 3.52-3.61 (2H, m), 3.99 (1H, m), 4.13 (1H, m), 4.64 (1H, d, J = 9.0 Hz), 5.74 (1H, s), 6.92 (1H, d, J = 4.2 Hz), 6.95 (1H, s), 7.26-7.30 (5H, m), 7.41 (1H, dd, J = 7.5, 8.1 Hz), 7.80 (2H, d, J = 7.5 Hz), 8.14 (1H, d, J = 5.4 Hz), 8.86 (1H, d, J = 5.1 Hz), 9.28 (1H, d, J = 1.25 Hz) (CDCl$_3$) | 590 |
| 5 | 2.29 (3H, s), 3.01-3.05 (4H, m), 3.12 (1H, dd, J = 10.8, 12.9 Hz), 3.21-3.23 (5H, m), 3.58 (3H, s), 3.52-3.61 (2H, m), 3.99 (1H, m), 4.13 (1H, m), 4.64 (1H, d, J = 9.0 Hz), 5.73 (1H, s), 6.69 (1H, s), 6.93 (2H, d, J = 8.8 Hz), 7.26-7.32 (4H, m), 7.41 (1H, dd, J = 7.5, 8.1 Hz), 7.77-7.81 (4H, m), 8.71 (2H, d, J = 5.9 Hz) (CDCl$_3$) | 589 |
| 6 | 1.67-2.18 (9H, m), 2.62-2.83 (6H, m), 3.09-3.17 (1H, m), 3.26-3.33 (1H, m), 3.53-3.74 (7H, m), 3.93-4.00 (1H, m), 4.13-4.17 (1H, m), 4.62 (1H, dd, J = 1.2, 10.2 Hz), 6.69 (1H, s), 6.93 (2H, d, J = 7.3 Hz), 7.26 (2H, d, J = 7.3 Hz), 7.79 (2H, d, J = 4.2 Hz), 8.71 (2H, d, J = 4.2 Hz) (CDCl$_3$) | 501 |
| 7 | 1.64-2.15 (9H, m), 2.61-2.83 (6H, m), 3.09-3.17 (1H, m), 3.26-3.33 (1H, m), 3.51-3.70 (7H, m), 3.93-4.00 (1H, m), 4.13-4.17 (1H, m), 4.61 (1H, dd, J = 1.2, 10.2 Hz), 6.94 (2H, d, J = 7.3 Hz), 7.28 (2H, d, J = 7.3 Hz), 7.34 (1H, s), 8.14 (1H, d, J = 4.2 Hz), 8.86 (1H, d, J = 4.2 Hz), 9.27 (1H, s) (CDCl$_3$) | 502 |
| 8 | 1.44-1.89 (10H, m), 2.30-2.38 (1H, m), 2.51-2.55 (4H, m), 2.70-2.76 (2H, m), 3.13-3.17 (1H, m), 3.26-3.32 (1H, m), 3.53-3.59 (5H, m), 3.75-3.79 (2H, m), 3.92-4.00 (1H, m), 4.12-4.16 (1H, m), 4.62 (1H, dd, J = 1.2, 10.2 Hz), 6.69 (1H, s), 6.92 (2H, d, J = 7.3 Hz), 7.29 (2H, d, J = 7.3 Hz), 7.78 (2H, d, J = 4.2 Hz), 8.71 (2H, d, J = 4.2 Hz) (CDCl$_3$) | 515 |
| 9 | 1.46-1.97 (10H, m), 2.59-2.78 (7H, m), 3.08-3.16 (1H, m), 3.26-3.32 (1H, m), 3.51-3.62 (5H, m), 3.75-3.79 (2H, m), 3.92-4.00 (1H, m), 4.12-4.16 (1H, m), 4.64 (1H, dd, J = 1.2, 10.2 Hz), 6.93 (2H, d, J = 7.3 Hz), 7.26-7.33 (3H, m), 8.13 (1H, d, J = 4.2 Hz), 8.86 (1H, d, J = 4.2 Hz), 9.27 (1H, s) (CDCl$_3$) | 516 |
| 10 | 1.14 (1H, m), 1.40 (4H, m), 1.66 (2H, m), 1.81 (3H, m), 2.79 (3H, s), 3.16 (1H, dd, J = 12.9, 10.8 Hz), 3.29 (1H, td, J = 11.4, 1.5 Hz), 3.53 (3H, s), 3.54 (3H, m), 3.95 (1H, td, J = 11.4, 1.5 Hz), 4.14 (1H, td, J = 11.4, 1.5 Hz), 4.61 (1H, dd, J = 10.8, 2.4 Hz), 6.69 (1H, s), 6.77 (2H, d, J = 8.9 Hz), 7.25 (2H, d, J = 8.9 Hz), 7.80 (2H, J = 4.8, 1.5 Hz, 2H), 8.71 (2H, dd, J = 4.8, 1.5 Hz) (CDCl$_3$) | 460 |
| 11 | 1.10-1.18 (1H, m), 1.35-1.49 (4H, m), 1.62-1.80 (5H, m), 2.71 (3H, s), 2.98-3.06 (2H, m), 3.46 (3H, s), 3.59-3.76 (3H, m), 3.83-3.89 (1H, m), 4.01-4.04 (1H, m), 4.60 (1H, d, 10.2 Hz), 6.75 (2H, d, J = 7.2 Hz), 6.88 (1H, s), 7.23 (2H, d, J = 7.3 Hz), 8.19 (1H, d, J = 4.2 Hz), 9.00 (1H, d, J = 4.2 Hz), 9.29 (1H, s) (CDCl$_3$) | 461 |

TABLE 4-continued

| Compound No. | ¹H-NMR δ: | LC-MS (M + 1) |
|---|---|---|
| 12 | 1.62 (1H, br.s), 2.62 (1H, t, J = 5.3 Hz), 2.68 (4H, t, J = 4.9 Hz), 3.14 (1H, dd, J = 10.8, 12.9 Hz), 3.23 (4H, t, J = 4.7 Hz), 3.31 (1H, m), 3.53-3.69 (5H, m), 3.57 (3H, s), 3.98 (1H, m), 4.14 (1H, m), 4.64 (1H, dd, J = 1.9, 10.4 Hz), 6.70 (1H, s), 6.95 (2H, d, J = 8.7 Hz), 7.31 (2H, d, J = 8.6 Hz), 7.79 (2H, d, J = 6.0 Hz), 8.71 (2H, d, J = 6.0 Hz) (CDCl₃) | 477 |
| 13 | 1.61 (1H, br.s), 2.61 (1H, t, J = 5.3 Hz), 2.68 (4H, t, J = 4.9 Hz), 3.13 (1H, dd, J = 10.8, 12.9 Hz), 3.24 (4H, t, J = 4.7 Hz), 3.31 (1H, m), 3.53-3.69 (5H, m), 3.57 (3H, s), 3.98 (1H, m), 4.16 (1H, m), 4.63 (1H, dd, J = 1.9, 10.4 Hz), 6.97 (2H, d, J = 8.7 Hz), 7.30 (1H, s), 8.14 (2H, d, J = 5.4 Hz), 8.86 (2H, d, J = 5.1 Hz), 9.28 (1H, s) (CDCl₃) | 478 |
| 14 | 1.50 (8H, m), 2.20 (1H, m), 2.55 (3H, m), 3.00 (1H, m), 3.15 (1H, dd, J = 10.8, 12.9 Hz), 3.28-3.31 (3H, m), 3.45-3.60 (4H, m), 3.57 (3H, s), 3.98 (1H, m), 4.16 (1H, m), 4.60 (1H, dd, J = 1.9, 10.4 Hz), 6.97 (2H, d, J = 8.7 Hz), 7.30 (1H, s), 8.14 (2H, d, J = 5.4 Hz), 8.86 (2H, d, J = 5.1 Hz), 9.28 (1H, s) (CDCl₃) | 502 |
| 15 | 1.47-1.65 (8H, m), 2.20 (1H, m), 2.55 (3H, m), 3.00 (1H, m), 3.15 (1H, dd, J = 10.8, 12.9 Hz), 3.28-3.31 (3H, m), 3.45-3.60 (4H, m), 3.57 (3H, s), 3.98 (1H, m), 4.16 (1H, m), 4.60 (1H, dd, J = 1.9, 10.4 Hz), 6.55 (2H, d, J = 8.7 Hz), 6.68 (1H, s), 7.31 (2H, d, J = 8.6 Hz), 7.79 (2H, d, J = 6.0 Hz), 8.71 (2H, d, J = 6.0 Hz) (CDCl₃) | 501 |
| 16 | 1.94 (1H, m), 2.20 (1H, m), 2.54 (4H, m), 3.00 (1H, m), 3.16-3.62 (8H, m), 3.56 (3H, s), 3.74 (4H, t, J = 4.6 Hz), 3.97 (1H, m), 4.16 (1H, m), 4.61 (1H, dd, J = 1.9, 10.4 Hz), 6.55 (2H, d, J = 8.7 Hz), 7.27 (2H, d, J = 8.7 Hz), 7.35 (1H, s), 8.15 (1H, d, J = 5.4 Hz), 8.85 (1H, d, J = 5.1 Hz), 9.27 (1H, s) (CDCl₃) | 504 |
| 17 | 1.90 (1H, m), 2.20 (1H, m), 2.54 (4H, m), 3.00 (1H, m), 3.14-3.60 (8H, m), 3.57 (3H, s), 3.76 (4H, t, J = 4.6 Hz), 3.97 (1H, m), 4.17 (1H, m), 4.61 (1H, dd, J = 1.9, 10.4 Hz), 6.55 (2H, d, J = 8.7 Hz), 6.69 (1H, s), 7.27 (2H, d, J = 8.6 Hz), 7.79 (2H, d, J = 6.0 Hz), 8.70 (2H, d, J = 6.0 Hz) (CDCl₃) | 503 |
| 18 | 1.83-2.05 (5H, m), 2.20 (1H, m), 2.55 (4H, m), 3.00 (1H, m), 3.15-3.63 (8H, m), 3.56 (3H, s), 3.97 (1H, m), 4.16 (1H, m), 4.61 (1H, dd, J = 1.9, 10.4 Hz), 6.56 (2H, d, J = 8.7 Hz), 6.69 (1H, s), 7.31 (2H, d, J = 8.6 Hz), 7.80 (2H, d, J = 6.0 Hz), 8.71 (2H, d, J = 6.0 Hz) (CDCl₃) | 486 |
| 19 | 1.47-1.94 (7H, m), 2.20 (1H, m), 2.55 (4H, m), 3.00 (1H, m), 3.15-3.63 (8H, m), 3.56 (3H, s), 3.97 (1H, m), 4.16 (1H, m), 4.61 (1H, dd, J = 1.9, 10.4 Hz), 6.55 (2H, d, J = 8.7 Hz), 6.69 (1H, s), 7.31 (2H, d, J = 8.6 Hz), 7.80 (2H, d, J = 6.0 Hz), 8.71 (2H, d, J = 6.0 Hz) (CDCl₃) | 500 |
| 20 | 1.94 (1H, m), 2.20 (1H, m), 2.54 (4H, m), 3.00 (1H, m), 3.16-3.62 (8H, m), 3.56 (3H, s), 3.74 (4H, t, J = 4.6 Hz), 3.97 (1H, m), 4.16 (1H, m), 4.61 (1H, dd, J = 1.9, 10.4 Hz), 6.55 (2H, d, J = 8.7 Hz), 6.69 (1H, s), 7.27 (2H, d, J = 8.6 Hz), 7.79 (2H, d, J = 6.0 Hz), 8.70 (2H, d, J = 6.0 Hz) (CDCl₃) | 502 |
| 21 | 1.68-1.73 (4H, m), 1.80-1.86 (1H, m), 2.12-2.18 (1H, m), 2.81-3.26 (10H, m), 3.44 (3H, s), 3.63-3.66 (3H, m), 3.84-4.00 (2H, m), 4.58 (1H, dd, J = 1.2 Hz, 10.2 Hz), 6.51 (2H, d, J = 7.2 Hz), 6.82 (1H, s), 7.21 (2H, d, J = 7.2 Hz), 7.96 (2H, d, J = 4.2 Hz), 8.68 (2H, d, J = 4.2 Hz) (DMSO-d6) | 487 |
| 22 | 1.68-1.72 (4H, m), 1.87-1.91 (1H, m), 2.07-2.11 (1H, m), 2.98-3.18 (10H, m), 3.42 (3H, s), 3.45-3.60 (3H, m), 3.86-4.02 (2H, m), 4.57 (1H, dd, J = 1.2 Hz, 10.2 Hz), 6.51 (2H, d, J = 7.2 Hz), 7.00 (1H, s), 7.23 (2H, d, J = 7.2 Hz), 8.19 (1H, dd, J = 1.2 Hz, 4.2 Hz), 9.00 (1H, d, J = 4.2 Hz), 9.29 (1H, d, J = 1.2 Hz) (DMSO-d6) | 488 |
| 23 | 1.97-2.20 (2H, m), 1.98 (3H, s), 3.13-3.62 (9H, m), 3.58 (3H, s), 3.97 (1H, m), 4.60-4.64 (2H, m), 6.58 (2H, d, J = 8.7 Hz), 6.69 (1H, s), 7.32 (2H, d, J = 9.0 Hz), 7.79 (2H, d, J = 6.0 Hz), 8.71 (2H, d, J = 6.0 Hz) (CDCl₃) | 475 |
| 24 | 2.04-2.23 (2H, m), 2.12 (3H, s), 2.94 (3H, s), 3.15 (1H, dd, J = 10.8, 12.8 Hz), 3.25-3.35 (3H, m), 3.47-3.63 (4H, m), 3.56 (3H, s), 3.98 (1H, t, J = 4.6 Hz), 4.12 (1H, m), 4.16 (1H, m), 4.62 (1H, d, J = 10.5 Hz), 5.40 (1H, m), 6.59 (2H, d, J = 8.7 Hz), 6.69 (1H, s), 7.29 (2H, d, J = 8.6 Hz), 7.80 (2H, d, J = 6.0 Hz), 8.70 (2H, d, J = 6.0 Hz) (CDCl₃) | 488 |
| 25 | 1.48 (9H, s), 2.04-2.23 (2H, m), 2.80 (3H, s), 3.15 (1H, dd, J = 10.8, 12.8 Hz), 3.25-3.35 (3H, m), 3.47-3.63 (4H, m), 3.56 (3H, s), 3.98 (1H, t, J = 4.6 Hz), 4.13 (1H, m), 4.62 (1H, dd, J = 1.7, 10.3 Hz), 4.91 (1H, m), 6.59 (2H, d, J = 8.7 Hz), 6.68 (1H, s), 7.29 (2H, d, J = 8.6 Hz), 7.80 (2H, d, J = 6.0 Hz), 8.70 (2H, d, J = 6.0 Hz) (CDCl₃) | 546 |
| 26 | 1.48 (9H, s), 2.10-2.20 (2H, m), 2.81 (3H, s), 3.14-4.62 (9H, m), 3.98 (1H, m), 6.58 (2H, d, J = 8.7 Hz), 6.69 (1H, s), 7.28 (2H, d, J = 8.7 Hz), 7.79 (2H, dd, J = 4.8, 1.5 Hz), 8.71 (2H, dd, J = 4.5, 1.2 Hz) (CDCl₃) | 547 |
| 27 | 2.04-2.21 (2H, m), 2.07 (3H, s), 2.94 (3H, s), 3.15-3.58 (7H, m), 3.56 (3H, s), 3.98-4.15 (2H, m), 4.61-4.64 (2H, m), 5.44 (1H, m), 6.59 (2H, m), 6.70 (1H, s), 7.30 (2H, m), 7.80 (2H, d, J = 5.4 Hz), 8.71 (2H, d, J = 5.4 Hz) (CDCl₃) | 489 |
| 28 | 1.60 (4H, m), 1.72 (2H, m), 1.86 (2H, m), 2.80 (3H, s), 3.16 (1H, dd, J = 12.8, 10.8 Hz), 3.30 (1H, dd, J = 11.4, 2.0 Hz), 3.56 (3H, s), 3.57 (2H, m), 3.97 (1H, td, J = 11.4, 2.0 Hz), 3.56 (3H, s), 3.57 (2H, m), 3.97 (1H, td, J = 11.4, 2.4 Hz), 4.18 (2H, m), 4.61 (1H, dd, J = 10.4, 2.2 Hz), 6.68 (1H, s), 6.82 (2H, d, J = 8.0 Hz), 7.25 (2H, d, J = 8.0 Hz), 7.80 (2H, dd, J = 4.8, 1.2 Hz), 8.71 (2H, dd, J = 4.8, 1.2 Hz) (CDCl₃) | 446 |
| 29 | 1.59 (4H, m), 1.72 (2H, m), 1.88 (2H, m), 2.80 (3H, s), 3.15 (1H, dd, J = 12.7, 10.5 Hz), 3.30 (1H, td, J = 11.4, 2.0 Hz), 3.56 (2H, | 447 |

TABLE 4-continued

| Compound No. | $^1$H-NMR δ: | LC-MS (M + 1) |
|---|---|---|
| | m), 3.57 (3H, s), 3.97 (1H, td, J = 11.4, 2.0 Hz), 4.17 (2H, m), 4.61 (1H, dd, J = 10.6, 2.1 Hz), 6.82 (2H, d, J = 8.7 Hz), 7.25 (2H, d, J = 8.7 Hz), 7.32 (1H, s), 8.15 (1H, d, J = 5.2 Hz), 8.86 (1H, d, J = 5.2 Hz), 9.27 (1H, s) (CDCl$_3$) | |
| 30 | 1.51 (4H, m), 1.62 (4H, m), 1.72 (2H, m), 1.82 (2H, m), 2.77 (3H, s), 3.16 (1H, dd, J = 12.8, 10.4 Hz), 3.13 (1H, td, J = 11.4, 2.0 Hz), 3.56 (3H, s), 3.60 (2H, m), 3.77 (1H, m), 3.97 (1H, td, J = 11.4, 2.0 Hz), 4.14 (1H, dd, J = 11.4, 2.0 Hz), 4.60 (1H, dd, J = 10.4, 2.0 Hz), 6.68 (1H, s), 6.75 (2H, d, J = 9.2 Hz), 7.25 (2H, d, J = 9.2 Hz), 7.80 (2H, dd, J = 4.4, 1.6 Hz), 8.71 (2H, dd, J = 4.4, 1.6 Hz) (CDCl$_3$) | 474 |
| 31 | 1.52 (4H, m), 1.64 (4H, m), 1.72 (2H, m), 1.83 (2H, m), 2.77 (3H, s,) 3.16 (1H, dd, J = 13.2, 10.8 Hz), 3.29 (1H, td, J = 11.4, 2.0 Hz), 3.56 (3H, s), 3.57 (3H, s), 3.97 (2H, m), 3.97 (1H, td, J = 11.4, 2.0 Hz), 4.17 (1H, dd, J = 11.4, 2.0 Hz), 4.60 (1H, dd, J = 10.8, 2.0 Hz), 6.75 (2H, d, J = 8.4 Hz), 7.25 (2H, d, J = 8.4 Hz), 7.34 (1H, s), 8.15 (1H, dd, J = 5.2, 1.2 Hz), 8.86 (1H, d, J = 5.2 Hz), 9.27 (1H, d, J = 1.2 Hz) (CDCl$_3$) | 475 |
| 32 | 1.17 (3H, m), 1.36 (2H, m), 1.62 (1H, m), 1.75 (2H, m), 2.03 (2H, m), 3.14 (1H, dd, J = 12.9, 10.8 Hz), 3.29 (2H, m), 3.56 (3H, s), 3.57 (3H, m), 3.97 (1H, t, J = 11.7 Hz), 4.14 (1H, d, J = 11.7 Hz), 4.58 (1H, dd, J = 10.5, 1.8 Hz), 6.59 (2H, d, J = 8.4 Hz), 6.69 (1H, s), 7.19 (2H, d, J = 8.4 Hz), 7.80 (2H, dd, J = 4.5, 1.8 Hz), 8.71 (2H, dd, J = 4.5, 1.8 Hz) (CDCl$_3$) | 446 |
| 33 | 1.44 (2H, m), 1.62 (2H, m), 1.74 (2H, m), 2.02 (2H, m), 3.14 (1H, dd, J = 12.8, 10.8 Hz), 3.30 (1H, td, J = 11.4, 2.8 Hz), 3.56 (3H, s), 3.58 (2H, m), 3.71 (br s, 1H), 3.79 (1H, m), 3.96 (1H, td, J = 11.4, 2.0 Hz), 4.13 (1H, td, 11.4, 2.0 Hz), 4.58 (1H, dd, J = 10.4, 2.0 Hz), 6.60 (2H, d, J = 8.4 Hz), 6.68 (1H, s), 7.20 (2H, d, J = 8.4 Hz), 7.80 (2H, dd, J = 6.0, 1.2 Hz), 8.71 (2H, dd, J = 6.0, 1.2 Hz) (CDCl$_3$) | 432 |
| 34 | 3.13 (1H, dd, J = 10.8, 12.9 Hz), 3.30 (1H, m), 3.56 (3H, s), 3.50-3.72 (4H, m), 3.97-4.22 (5H, m), 4.60 (1H, dd, J = 1.9, 10.4 Hz), 4.80 (1H, m), 6.49 (2H, d, J = 8.7 Hz), 6.69 (1H, s), 7.26 (2H, d, J = 8.6 Hz), 7.79 (2H, d, J = 6.0 Hz), 8.71 (2H, d, J = 6.0 Hz) (CDCl$_3$) | 420 |
| 35 | 1.16 (3H, t, J = 6.9 Hz), 1.16 (1H, m), 1.39 (4H, m), 1.69 (1H, m), 1.85 (4H, m), 3.18 (1H, dd, J = 12.9, 10.8 Hz), 3.30 (3H, m), 3.56 (3H, s), 3.57 (3H, m), 3.97 (1H, t, J = 12.9 Hz), 4.15 (1H, d, J = 12.9 Hz), 4.59 (1H, dd, J = 10.8, 2.1 Hz), 6.69 (1H, s), 6.72 (2H, d, J = 8.7 Hz), 7.24 (2H, d, J = 8.7 Hz), 7.81 (2H, dd, J = 6.4, 2.0 Hz), 8.72 (2H, dd, J = 6.4, 2.0 Hz) (CDCl$_3$) | 474 |
| 36 | 0.92 (3H, t, J = 8.0 Hz), 1.17 (1H, m), 1.38 (4H, m), 1.54 (2H, m), 1.70 (1H, d, J = 13.3 Hz), 1.83 (4H, m), 3.11 (2H, t, J = 8.0 Hz), 3.17 (1H, dd, J = 12.8, 10.8 Hz), 3.30 (1H, td, J = 11.4, 2.0 Hz), 3.59 (3H, s), 3.61 (2H, m), 3.96 (1H, td, J = 11.4, 1.2 Hz), 4.16 (1H, d, J = 11.4 Hz), 4.59 (1H, dd, J = 19.4, 2.0 Hz), 6.68 (1H, s), 6.70 (2H, d, J = 8.8 Hz), 7.23 (2H, d, J = 8.8 Hz), 7.79 (2H, d, J = 6.0 Hz), 8.71 (2H, d, J = 6.0 Hz) (CDCl$_3$) | 488 |
| 37 | 1.43 (2H, m), 1.58 (2H, m), 1.79 (2H, m), 2.08 (2H, m), 2.77 (3H, s), 3.15 (1H, dd, J = 13.2, 11.2 Hz), 3.30 (1H, td, J = 11.4, 2.0 Hz), 3.59 (4H, m), 3.97 (1H, td, J = 11.4, 1.2 Hz), 4.14 (1H, d, J = 11.4 Hz), 4.61 (1H, dd, J = 10.8, 2.4 Hz), 6.68 (1H, s), 6.78 (2H, d, J = 8.8 Hz), 7.26 (2H, d, J = 8.8 Hz), 7.80 (2H, d, J = 4.8 Hz), 8.71 (2H, d, J = 4.8 Hz) (CDCl$_3$) | 476 |
| 38 | 1.45 (2H, m), 2.03 (2H, d, J = 12.8 Hz), 3.13 (1H, dd, J = 13.2, 10.8 Hz), 3.30 (1H, t, J = 11.4 Hz), 3.54 (6H, m), 4.00 (3H, m), 4.12 (1H, d, J = 11.4 Hz), 4.59 (1H, d, J = 11.4 Hz), 6.62 (2H, d, J = 8.4 Hz), 6.68 (1H, s), 7.21 (2H, d, J = 8.4 Hz), 7.79 (2H, dd, J = 4.8, 1.6 Hz), 8.71 (2H, dd, J = 4.8, 1.6 Hz) (CDCl$_3$) | 448 |
| 39 | 2.20 (3H, s), 3.15 (1H, dd, J = 10.8, 12.9 Hz), 3.29 (1H, m), 3.525-3.65 (2H, m), 3.58 (3H, s), 3.98 (1H, m), 4.16 (1H, m), 4.70 (1H, dd, J = 1.9, 10.4 Hz), 6.70 (1H, s), 6.91 (1H, s), 7.38 (2H, d, J = 8.4 Hz), 7.54 (2H, d, J = 8.4 Hz), 7.79 (2H, d, J = 6.0 Hz), 8.71 (2H, d, J = 6.0 Hz) (CDCl$_3$) | 406 |
| 40 | 2.20 (3H, s), 3.15 (1H, dd, J = 10.8, 12.9 Hz), 3.29 (1H, m), 3.52-3.65 (2H, m), 3.63 (3H, s), 3.98 (1H, m), 4.16 (1H, m), 4.70 (1H, dd, J = 1.9, 10.4 Hz), 7.26 (1H, s), 7.36 (2H, d, J = 8.7 Hz), 7.39 (1H, s), 7.55 (2H, d, J = 8.7 Hz), 8.14 (1H, d, J = 5.4 Hz), 8.87 (1H, d, J = 5.1 Hz), 9.27 (1H, s) (CDCl$_3$) | 407 |
| 41 | 1.88 (3H, s), 3.15 (1H, dd, J = 10.8, 12.9 Hz), 3.28 (3H, s), 3.34 (1H, m), 3.55-3.71 (2H, m), 3.59 (3H, s), 4.01 (1H, m), 4.16 (1H, m), 4.77 (1H, dd, J = 1.9, 10.4 Hz), 6.71 (1H, s), 7.22 (2H, d, J = 8.4 Hz), 7.48 (2H, d, J = 8.4 Hz), 7.79 (2H, d, J = 6.0 Hz), 8.72 (2H, d, J = 6.0 Hz) (CDCl$_3$) | 420 |
| 42 | 1.68 (2H, dd, J = 11.2, 4.4 Hz), 1.84 (2H, qd, J = 11.2, 4.4 Hz), 2.81 (3H, s), 3.15 (1H, dd, J = 12.8, 10.4 Hz), 3.29 (1H, td, J = 11.4, 2.0 Hz), 3.51 (3H, m), 3.56 (3H, s), 3.62 (1H, d, J = 13.2 Hz), 3.83 (1H, m), 3.97 (1H, td, J = 11.4, 2.4 Hz), 4.07 (2H, dd, J = 11.2, | 462 |

TABLE 4-continued

| Compound No. | $^1$H-NMR δ: | LC-MS (M + 1) |
|---|---|---|
|  | 4.4 Hz), 4.14 (1H, dd, J = 11.4, 2.4 Hz), 4.62 (1H, dd, J = 10.8, 2.4 Hz), 6.68 (1H, s), 6.82 (2H, d, J = 9.2 Hz), 7.27 (2H, d, J = 9.2 Hz), 7.79 (2H, d, J = 6.0 Hz), 8.71 (2H, d, J = 6.0 Hz) (CDCl$_3$) |  |
| 43 | 1.68 (2H, dd, J = 11.2, 4.4 Hz), 1.85 (2H, qd, J = 11.2, 4.4 Hz), 3.14 (1H, dd, J = 12.8, 10.8 Hz), 3.28 (1H, td, J = 11.4, 2.0 Hz), 3.45 (2H, t, J = 11.8 Hz), 3.57 (3H, s), 3.58 (2H, m), 3.82 (1H, m), 3.98 (1H, td, J = 11.4, 2.4 Hz), 4.07 (2H, dd, J = 11.2, 4.4 Hz), 4.16 (1H, dd, J = 11.2, 4.4 Hz), 4.62 (1H, dd, J = 10.4, 2.0 Hz), 6.82 (2H, d, J = 11.6 Hz), 7.27 (2H, d, J = 11.6 Hz), 7.34 (1H, s), 8.14 (1H, dd, J = 4.8, 1.2 Hz), 8.85 (1H, d, J = 4.8 Hz), 9.27 (1H, d, J = 1.2 Hz) (CDCl$_3$) | 463 |
| 44 | 2.38 (2H, t, J = 7.3 Hz), 3.13 (1H, dd, J = 10.8, 12.9 Hz), 3.30 (1H, m), 3.56 (3H, s), 3.50-3.59 (2H, m), 3.88 (4H, t, J = 7.3 Hz), 3.96 (1H, td, J = 2.2, 11.6 Hz), 4.14 (1H, d, J = 11.8 Hz), 4.61 (1H, dd, J = 2.1, 10.4 Hz), 6.45 (2H, d, J = 8.6 Hz), 6.68 (1H, s), 7.24 (2H, d, J = 8.6 Hz), 7.96 (2H, d, J = 6.0 Hz), 8.71 (2H, d, J = 6.0 Hz) (CDCl$_3$) | 404 |
| 45 | 2.38 (2H, t, J = 7.3 Hz), 3.13 (1H, dd, J = 10.8, 12.9 Hz), 3.30 (1H, m), 3.56 (3H, s), 3.50-3.59 (2H, m), 3.88 (4H, t, J = 7.3 Hz), 3.96 (1H, td, J = 2.2, 11.6 Hz), 4.14 (1H, d, J = 11.8 Hz), 4.61 (1H, dd, J = 2.1, 10.4 Hz), 6.47 (2H, d, J = 8.7 Hz), 7.26 (2H, d, J = 8.7 Hz), 7.34 (1H, s), 8.14 (1H, d, J = 5.4 Hz), 8.87 (1H, d, J = 5.1 Hz), 9.27 (1H, s) (CDCl$_3$) | 405 |
| 46 | 0.82 (1H, m), 1.00 (2H, m), 1.39 (2H, m), 1.68 (1H, m), 1.71 (2H, m), 1.73 (3H, s), 1.81 (2H, m), 3.14 (1H, dd, J = 13.1, 10.6 Hz), 3.36 (1H, td, J = 11.4, 2.4 Hz), 3.57 (1H, d, J = 11.4 Hz), 3.60 (3H, s), 3.72 (1H, d, J = 13.1 Hz), 4.01 (m, td, J = 11.4, 2.4 Hz), 4.20 (1H, dd, J = 11.4, 1.8 Hz), 4.59 (1H, m), 4.79 (1H, dd, J = 10.6, 1.8 Hz), 6.70 (1H, s), 7.13 (2H, d, J = 8.3 Hz), 7.46 (2H, d, J = 8.3 Hz), 7.79 (2H, dd, J = 4.8, 1.4 Hz), 8.72 (2H, dd, J = 4.8, 1.4 Hz), (CDCl$_3$) | 488 |
| 47 | 0.88 (1H, m), 1.01 (2H, m), 1.39 (2H, m), 1.68 (1H, m), 1.70 (2H, m), 1.73 (3H, s), 1.81 (2H, m), 3.14 (1H, dd, J = 12.8, 10.6 Hz), 3.33 (1H, td, J = 12.0, 2.4 Hz), 3.56 (1H, d, J = 12.0), 3.61 (3H, s), 3.69 (1H, d, J = 12.8 Hz), 4.03 (1H, td, J = 12.0, 2.4 Hz), 4.21 (1H, td, J = 12.0, 2.4 Hz), 4.60 (1H, m), 4.79 (1H, dd, J = 10.6, 1.6 Hz), 7.14 (2H, d, J = 8.4 Hz), 7.36 (1H, s), 7.47 (2H, d, J = 8.4 Hz), 8.14 (1H, dd, J = 4.8, 1.2 Hz), 8.88 (1H, d, J = 4.8 Hz), 9.28 (1H, d, J = 1.2 Hz) (CDCl$_3$) | 489 |
| 48 | 3.14 (1H, dd, J = 10.8, 12.9 Hz), 3.31 (1H, m), 3.52-3.65 (2H, m), 3.61 (3H, s), 3.99 (1H, m), 4.16 (1H, m), 4.69 (1H, dd, J = 1.9, 10.4 Hz), 6.58 (1H, br.s), 6.69-6.77 (1H, m), 6.87 (1H, d, J = 8.4 Hz), 7.19 (1H, m), 7.38 (4H, m), 7.49-7.51 (1H, m), 7.80 (2H, d, J = 6.2 Hz), 8.21 (1H, d, J = 6.0 Hz), 8.72 (2H, d, J = 6.2 Hz) (CDCl$_3$) | 441 |
| 49 | 3.14 (1H, dd, J = 10.8, 12.9 Hz), 3.31 (1H, m), 3.52-3.65 (2H, m), 3.61 (3H, s), 3.99 (1H, m), 4.16 (1H, m), 4.69 (1H, dd, J = 1.9, 10.4 Hz), 6.58 (1H, br.s), 6.69-6.77 (1H, m), 6.87 (1H, d, J = 8.4 Hz), 7.38 (4H, m), 7.49-7.51 (1H, m), 8.21 (1H, d, J = 6.0 Hz), 8.14 (1H, dd, J = 1.2, 4.8 Hz), 8.86 (1H, d, J = 5.1 Hz), 9.28 (1H, d, J = 1.2 Hz) (CDCl$_3$) | 442 |
| 50 | 3.14 (1H, dd, J = 10.8, 12.9 Hz), 3.30 (1H, m), 3.58-3.67 (2H, m), 3.59 (3H, s), 4.00 (1H, m), 4.16 (1H, m), 4.70 (1H, dd, J = 1.9, 10.4 Hz), 6.70 (1H, s), 7.23 (1H, s), 7.38 (2H, d, J = 8.3 Hz), 7.55 (2H, d, J = 8.3 Hz), 7.80 (4H, m), 8.72 (4H, m) (CDCl$_3$) | 441 |
| 51 | 3.15 (1H, dd, J = 10.8, 13.2 Hz), 3.32 (1H, m), 3.54-3.67 (2H, m), 3.58 (3H, m), 4.00-4.16 (3H, m), 4.68 (1H, dd, J = 2.4, 10.8 Hz), 5.78 (1H, s), 6.70 (1H, s), 7.10 (2H, d, J = 8.4 Hz), 7.20-7.22 (1H, m), 7.35 (2H, d, J = 8.7 Hz), 7.36 (1H, m), 7.80 (2H, d, J = 6.0 Hz), 8.20 (1H, dd, J = 1.5, 4.5 Hz), 8.41 (1H, d, J = 2.7 Hz), 8.72 (2H, d, J = 6.0 Hz) (CDCl$_3$) | 441 |
| 52 | 0.85 (1H, m), 1.27 (2H, m), 1.37 (2H, m), 1.58 (1H, m), 1.78 (2H, m), 1.97 (2H, m), 2.97 (3H, s), 3.14 (1H, dd, J = 13.2, 10.8 Hz), 3.32 (1H, td, J = 11.2, 2.0 Hz), 3.56 (1H, d, J = 11.2 Hz), 3.59 (3H, s), 3.71 (1H, d, J = 13.2 Hz), 4.01 (1H, td, J = 11.2, 2.0 Hz), 4.08 (1H, m), 4.19 (1H, dd, J = 11.2, 2.0 Hz), 4.78 (1H, dd, J = 10.8, 2.4 Hz), 6.71 (1H, s), 7.29 (2H, d, J = 8.4 Hz), 7.46 (2H, d, J = 8.4 Hz), 7.80 (2H, dd, J = 4.8, 1.2 Hz), 8.73 (2H, dd, J = 4.8, 1.2 Hz) (CDCl$_3$) | 524 |
| 53 | 0.87 (1H, m), 1.18 (2H, m), 1.39 (2H, m), 1.69 (1H, m), 1.78 (2H, m), 1.97 (2H, m), 2.98 (3H, m), 3.28 (1H, td, J = 11.2, 2.2 Hz), 3.55 (1H, d, J = 11.2 Hz), 3.60 (3H, s), 3.69 (1H, d, J = 13.2 Hz), 4.00 (1H, td, J = 11.2, 2.2 Hz), 4.07 (1H, m), 4.20 (1H, dd, J = 11.2, 2.2 Hz), 4.77 (1H, dd, J = 10.4, 2.0 Hz), 7.30 (2H, d, J = 8.0 Hz), 7.37 (1H, s), 7.47 (2H, d, J = 8.0 Hz), 8.16 (1H, dd, J = 4.8, 1.2 Hz), 8.89 (1H, d, J = 4.8 Hz), 9.28 (1H, d, J = 1.2 Hz) (CDCl$_3$) | 525 |
| 54 | 0.97 (1H, m), 1.22 (2H, m), 1.42 (2H, m), 1.60 (1H, m), 1.76 (2H, m), 1.95 (2H, m), 3.01 (1H, dd, J = 12.8, 10.8 Hz), 3.30 (1H, td, J = 11.2, 2.4 Hz), 3.52 (1H, d, J = 11.2 Hz), 3.56 (3H, s), 3.57 (1H, d, J = 12.8 Hz), 3.95 (1H, td, J = 11.2, 2.4 Hz), 4.16 (1H, dd, J = 11.2, 2.4 Hz), 4.66 (1H, m), 4.67 (1H, d, J = 10.8 Hz), 6.69 (1H, | 550 |

TABLE 4-continued

| Compound No. | $^1$H-NMR δ: | LC-MS (M + 1) |
|---|---|---|
| | s), 7.05 (2H, d, J = 8.0 Hz), 7.15 (1H, t, J = 8.0 Hz), 7.25 (2H, t, J = 8.0 Hz), 7.78 (2H, dd, J = 5.2, 1.2 Hz), 8.72 (2H, dd, J = 5.2, 1.2 Hz) (CDCl$_3$) | |
| 55 | 0.96 (1H, m), 1.20 (2H, m), 1.40 (2H, m), 1.60 (1H, m), 1.78 (2H, m), 1.95 (2H, m), 3.01 (1H, t, J = 11.7 Hz), 3.29 (1H, td, J = 11.6, 2.4 Hz), 3.51 (2H, m), 3.57 (3H, s), 3.96 (1H, t, J = 11.6 Hz), 4.16 (1H, d, J = 11.6 Hz), 4.66 (1H, m), 4.67 (1H, d, J = 9.0 Hz), 7.06 (2H, d, J = 8.0 Hz), 7.15 (1H, t, J = 8.0 Hz), 7.26 (2H, t, J = 8.0 Hz), 7.35 (1H, s), 8.11 (1H, d, J = 5.1 Hz), 8.87 (1H, d, J = 5.1 Hz), 9.28 (1H, s) (CDCl$_3$) | 551 |
| 56 | 0.57 (2H, m), 0.90 (1H, m), 0.99 (2H, m), 1.07 (2H, m), 1.39 (2H, m), 1.59 (1H, m), 1.74 (2H, m), 1.83 (2H, m), 3.16 (1H, dd, J = 12.8, 10.4 Hz), 3.38 (1H, td, J = 13.2, 2.4 Hz), 3.57 (1H, d, J = 13.2 Hz), 3.60 (3H, s), 3.71 (1H, d, J = 13.2 Hz), 4.02 (1H, td, J = 13.2, 2.4 Hz), 4.21 (1H, dd, J = 13.2, 2.4 Hz), 4.60 (1H, m), 4.79 (1H, dd, J = 10.4, 2.0 Hz), 6.70 (1H, s), 7.22 (2H, d, J = 8.4 Hz), 7.47 (2H, d, J = 8.4 Hz), 7.80 (2H, dd, J = 5.2, 1.2 Hz), 8.73 (2H, dd, J = 5.2, 1.2 Hz) (CDCl$_3$) | 514 |
| 57 | 0.50 (2H, m), 0.90 (1H, m), 0.99 (2H, m), 1.08 (2H, m), 1.40 (2H, m), 1.57 (1H, m), 1.73 (2H, m), 1.82 (2H, m), 3.15 (1H, dd, J = 12.8, 10.8 Hz), 3.37 (1H, td, J = 13.2, 2.4 Hz), 3.57 (1H, d, J = 13.2 Hz), 3.61 (3H, s), 3.70 (1H, d, J = 12.8 Hz), 4.03 (1H, td, J = 13.2, 2.4 Hz), 4.21 (1H, dd, J = 13.2, 2.4 Hz), 4.60 (1H, m), 4.79 (1H, dd, J = 10.8, 2.0 Hz), 7.23 (2H, d, J = 8.0 Hz), 7.36 (1H, s), 7.48 (2H, d, J = 8.0 Hz), 8.15 (1H, d, J = 5.2 Hz), 8.88 (1H, d, J = 5.2 Hz), 9.29 (1H, s) (CDCl$_3$) | 515 |
| 58 | 0.82 (1H, m), 1.05 (2H, m), 1.37 (2H, m), 1.65 (1H, m), 1.70 (2H, m), 1.82 (2H, m), 3.13 (1H, dd, J = 13.2, 10.6 Hz), 3.33 (1H, td, J = 13.6, 2.4 Hz), 3.55 (1H, d, J = 13.6 Hz), 3.59 (3H, s), 3.70 (1H, d, J = 13.2 Hz), 4.00 (1H, td, J = 13.6, 2.4 Hz), 4.17 (2H, m), 4.75 (1H, dd, J = 10.6, 2.0 Hz), 6.71 (1H, s), 7.07 (2H, d, J = 8.4 Hz), 7.38 (2H, d, J = 8.4 Hz), 7.47 (2H, t, J = 7.6 Hz), 7.56 (1H, t, J = 7.6 Hz), 7.76 (2H, d, J = 7.6 Hz), 7.81 (2H, dd, J = 4.4, 1.6 Hz), 8.74 (2H, dd, J = 4.4, 1.6 Hz) (CDCl$_3$) | 586 |
| 59 | 0.81 (1H, m), 1.05 (2H, m), 1.36 (2H, m), 1.63 (1H, m), 1.70 (2H, m), 1.81 (2H, m), 3.13 (1H, dd, J = 12.2, 10.8 Hz), 3.30 (1H, td, J = 13.2, 2.4 Hz), 3.54 (1H, d, J = 13.2 Hz), 3.60 (3H, s), 3.68 (1H, d, J = 12.2 Hz), 4.01 (1H, td, J = 13.2, 2.4 Hz), 4.15 (2H, m), 4.75 (1H, dd, J = 10.8, 2.0 Hz), 7.07 (2H, d, J = 7.6 Hz), 7.37 (1H, s), 7.38 (2H, d, J = 7.6 Hz), 7.48 (2H, t, J = 7.6 Hz), 7.56 (1H, t, J = 7.6 Hz), 7.77 (2H, d, J = 8.0 Hz), 8.18 (1H, dd, J = 5.2, 1.2 Hz), 8.90 (1H, d, J = 5.2 Hz), 9.29 (1H, d, J = 1.2 Hz) (CDCl$_3$) | 587 |
| 60 | 1.13 (1H, m), 1.39 (4H, m), 1.67 (1H, m), 1.82 (4H, m), 3.15 (1H, dd, J = 13.2, 10.8 Hz), 3.30 (1H, m), 3.39 (2H, t, J = 6.2 Hz), 3.52 (2H, m), 3.56 (3H, s), 3.62 (1H, d, J = 12.8 Hz), 3.69 (2H, br s), 3.97 (1H, td, J = 11.4, 2.4 Hz), 4.15 (1H, d, J = 11.4 Hz), 4.62 (1H, dd, J = 10.8, 2.4 Hz), 6.69 (1H, s), 6.87 (2H, d, J = 8.8 Hz), 7.27 (2H, d, J = 8.8 Hz), 7.80 (2H, dd, J = 4.8, 1.6 Hz), 8.71 (2H, dd, J = 4.8, 1.6 Hz) (CDCl$_3$) | 490 |
| 61 | 1.12 (1H, m), 1.38 (4H, m), 1.71 (1H, m), 1.83 (4H, m), 3.15 (1H, dd, J = 12.8, 10.4 Hz), 3.30 (1H, m), 3.39 (2H, t, J = 6.2 Hz), 3.51 (1H, m), 3.58 (3H, s), 3.62 (1H, m), 3.69 (1H, q, J = 6.2 Hz), 3.74 (1H, m), 3.98 (1H, td, J = 11.4, 2.0 Hz), 4.16 (1H, d, J = 11.4 Hz), 4.62 (1H, dd, J = 10.4, 2.0 Hz), 6.88 (2H, d, J = 8.4 Hz), 7.27 (2H, d, J = 8.4 Hz), 7.34 (1H, s), 8.15 (1H, dd, J = 5.2, 0.8 Hz), 8.87 (1H, d, J = 5.2 Hz), 9.27 (1H, d, J = 0.8 Hz) (CDCl$_3$) | 491 |
| 62 | 3.07-3.12 (2H, m), 3.62 (3H, s), 3.62-3.63 (1H, m), 3.76-3.80 (2H, m), 3.90-4.09 (5H, m), 4.38 (2H, br), 4.70 (1H, dd, J = 1.2 Hz, 4.2 Hz), 6.72 (1H, dd, J = 7.2 Hz, 7.3 Hz), 7.05-7.44 (4H, m), 8.31 (2H, d, J = 7.2 Hz), 8.48 (2H, d, J = 7.2 Hz), 8.90-8.96 (4H, m) (DMSO-d6). | 466 |
| 63 | 3.02-3.12 (4H, m), 3.51 (3H, s), 3.69-3.76 (2H, m), 3.90-4.07 (4H, m), 4.70 (1H, dd, J = 1.2 Hz, 10.2 Hz), 6.73 (1H, dd, J = 7.2 Hz, 7.3 Hz), 7.01-7.26 (6H, m), 7.43 (2H, d, J = 7.2 Hz), 8.21 (1H, dd, J = 1.2 Hz, 4.2 Hz), 9.00 (1H, d, J = 4.2 Hz), 9.30 (1H, d, J = 1.2 Hz) (DMSO-d6). | 467 |
| 64 | 0.86-1.24 (6H, m), 1.52-1.63 (7H, m), 2.33-2.36 (1H, m), 2.62-2.72 (1H, m), 2.96-3.04 (2H, m), 3.12-3.20 (1H, m), 3.46 (3H, s), 3.65-3.74 (2H, m), 3.83-3.86 (1H, m), 4.03-4.06 (1H, m), 4.69 (1H, dd, J = 1.2 Hz, 10.2 Hz), 6.83 (1H, s), 7.10 (2H, d, J = 7.2 Hz), 7.35 (2H, d, J = 7.2 Hz), 7.96 (2H, d, J = 4.2 Hz), 8.70 (2H, d, J = 4.2 Hz) (DMSO-d6). | 486 |
| 65 | 0.82-1.35 (7H, m), 1.59-1.66 (7H, m), 2.33-2.36 (1H, m), 2.60-2.66 (1H, m), 2.98-3.00 (2H, m), 3.04-3.18 (1H, m), 3.47 (3H, s), 3.67-4.03 (4H, m), 4.68 (1H, dd, J = 1.2 Hz, 10.2 Hz), 6.87 (1H, s), 7.10 (2H, d, J = 7.2 Hz), 7.38 (2H, d, J = 7.2 Hz), 8.20 (1H, dd, J = 1.2 Hz, 4.2 Hz), 9.02 (1H, d, J = 4.2 Hz), 9.29 (1H, d, J = 1.2 Hz) (DMSO-d6). | 487 |
| 66 | 1.05-1.95 (10H, m), 3.16 (1H, dd, J = 12.8, 10.4 Hz), 3.31 (1H, m), 3.37 (3H, s), 3.45 (4H, m), 3.54 (2H, m), 3.56 (3H, s), 3.57 (1H, d, J = 13.2 Hz), 3.97 (1H, td, J = 13.3, 2.4 Hz), 4.13 (1H, dd, J = 13.3, | 504 |

TABLE 4-continued

| Compound No. | ¹H-NMR δ: | LC-MS (M + 1) |
|---|---|---|
|  | 2.4 Hz), 4.60 (1H, dd, J = 10.4, 2.0 Hz), 6.69 (1H, s), 6.78 (2H, d, J = 8.8 Hz), 7.24 (2H, d, J = 8.8 Hz), 7.80 (2H, d, J = 4.8 Hz), 8.71 (2H, d, J = 4.8 Hz) (CDCl₃) |  |
| 67 | 1.18 (1H, m), 1.40 (4H, m), 1.70 (1H, m), 1.83 (4H, m), 3.16 (1H, dd, J = 13.2, 10.8 Hz), 3.31 (1H, m), 3.38 (3H, s), 3.45 (4H, m), 3.56 (4H, m), 3.57 (3H, s), 3.97 (1H, m), 4.13 (1H, m), 4.60 (1H, dd, J = 10.8, 2.4 Hz), 6.78 (2H, d, J = 8.8 Hz), 7.25 (2H, d, J = 8.8 Hz), 7.26 (1H, s), 8.15 (1H, d, J = 5.6 Hz), 8.86 (1H, d, J = 5.6 Hz), 9.27 (1H, s) (CDCl₃) | 505 |
| 68 | 1.27-1.98 (10H, m), 2.24 (1H, m), 3.09 (1H, dd, J = 10.8, 12.9 Hz), 3.30 (1H, m), 3.53-3.65 (2H, m), 3.57 (3H, m), 3.99 (1H, td, J = 2.1, 13.5 Hz), 4.16 (1H, dd, J = 2.1, 11.8 Hz), 4.69 (1H, dd, J = 2.4, 10.8 Hz), 6.70 (1H, s), 7.25 (1H, br.s), 7.37 (2H, d, J = 8.7 Hz), 7.56 (2H, d, J = 8.7 Hz), 7.78 (2H, d, J = 6.3 Hz), 8.71 (2H, d, J = 6.3 Hz) (CDCl₃) | 474 |
| 69 | 1.27-1.99 (10H, m), 2.20 (1H, t), 3.09 (1H, dd, J = 10.8, 12.9 Hz), 3.30 (1H, m), 3.51-3.67 (2H, m), 3.58 (3H, s), 3.99 (1H, td, J = 2.1, 13.5 Hz), 4.16 (1H, dd, J = 2.1, 11.8 Hz), 4.70 (1H, dd, J = 2.4, 10.8 Hz), 7.20 (1H, br.s), 7.35 (1H, s), 7.36 (2H, d, J = 8.4 Hz), 7.56 (2H, d, J = 8.4 Hz), 8.13 (1H, d, J = 5.1 Hz), 8.86 (1H, d, J = 5.4 Hz), 9.27 (1H, s) (CDCl₃) | 475 |
| 70 | 3.12 (1H, dd, J = 10.5, 12.9 Hz), 3.31 (1H, td, J = 3.0, 12.0 Hz), 3.54-3.68 (2H, m), 3.58 (3H, s), 4.01 (1H, td, J = 2.1, 11.4 Hz), 4.18 (1H, dd, J = 1.8, 11.7 Hz), 4.73 (1H, dd, J = 2.1, 10.5 Hz), 6.70 (1H, s), 7.42-7.57 (5H, m), 7.70 (2H, d, J = 8.1 Hz), 7.79 (2H, d, J = 6.0 Hz), 7.88 (2H, d, J = 8.1 Hz), 7.92 (1H, br.s), 8.71 (2H, d, J = 6.3 Hz) (CDCl₃) | 468 |
| 71 | 3.12 (1H, dd, J = 10.4, 12.9 Hz), 3.29 (1H, td, J = 3.0, 12.0 Hz), 3.52-3.66 (2H, m), 3.59 (3H, s), 4.01 (1H, td, J = 2.1, 11.4 Hz), 4.20 (1H, dd, J = 1.2, 11.1 Hz), 4.74 (1H, dd, J = 2.1, 10.5 Hz), 7.36 (1H, s), 7.43-7.55 (5H, m), 7.70 (2H, d, J = 8.4 Hz), 7.88 (2H, d, J = 8.4 Hz), 7.92 (1H, br.s), 8.14 (1H, d, J = 5.4 Hz), 8.87 (1H, d, J = 5.1 Hz), 9.27 (1H, d, J = 1.2 Hz) (CDCl₃) | 469 |
| 72 | 3.17 (1H, dd, J = 10.4, 12.9 Hz), 3.37 (1H, t, J = 11.4 Hz), 3.49 (3H, s), 3.60 (3H, s), 3.58-3.72 (2H, m), 4.01-4.20 (2H, m), 4.74 (1H, d, J = 10.5 Hz), 6.60-6.67 (2H, m), 6.71 (1H, s), 7.25-7.37 (1H, m), 7.31 (2H, d, J = 8.4 Hz), 7.45 (2H, d, J = 8.4 Hz), 7.81 (2H, d, J = 6.0 Hz), 8.24 (1H, d, J = 3.6 Hz), 8.72 (2H, d, J = 6.0 Hz) (CDCl₃) | 455 |
| 73 | 3.17 (1H, dd, J = 10.8, 12.9 Hz), 3.32 (1H, td, J = 2.8, 11.4 Hz), 3.49 (3H, s), 3.61 (3H, s), 3.54-3.71 (2H, m), 4.02 (1H, td, J = 2.4, 11.4 Hz), 4.18 (1H, dd, J = 11.7, 18.0 Hz), 4.74 (1H, dd, J = 2.3, 10.6 Hz), 6.61 (1H, d, J = 8.8 Hz), 6.65 (1H, d, J = 1.9 Hz), 7.26-7.36 (4H, m), 7.45 (2H, d, J = 8.4 Hz), 8.17 (1H, d, J = 6.5 Hz), 8.24 (1H, d, J = 3.5 Hz), 8.88 (1H, d, J = 5.1 Hz), 9.28 (1H, d, J = 1.1 Hz) (CDCl₃) | 456 |
| 74 | 0.84-0.89 (2H, m), 1.08-1.13 (2H, m), 1.51 (1H, m), 3.09 (1H, dd, J = 10.6, 13.0 Hz), 3.30 (1H, td, J = 2.9, 13.0 Hz), 3.52-3.65 (2H, m), 3.57 (3H, s), 3.98 (1H, td, J = 2.1, 11.4 Hz), 4.16 (1H, dd, J = 11.7, 18.0 Hz), 4.70 (1H, dd, J = 1.9, 10.3 Hz), 6.69 (1H, s), 7.36 (2H, d, J = 8.3 Hz), 7.50 (1H, br.s), 7.55 (2H, d, J = 8.3 Hz), 7.79 (2H, d, J = 6.0 Hz), 8.71 (2H, d, J = 6.0 Hz) (CDCl₃) | 432 |
| 75 | 0.86-0.90 (2H, m), 1.09-1.13 (2H, m), 1.51 (1H, m), 3.19 (1H, dd, J = 10.6, 13.0 Hz), 3.28 (1H, t, J = 9.9 Hz), 3.52-3.65 (2H, m), 3.59 (3H, s), 3.98 (1H, td, J = 2.1, 11.4 Hz), 4.16 (1H, dd, J = 11.7, 18.0 Hz), 4.70 (1H, dd, J = 1.9, 10.3 Hz), 7.24-7.44 (3H, m), 7.43 (1H, br.s), 7.56 (2H, d, J = 8.4 Hz), 8.13 (1H, d, J = 5.4 Hz), 8.86 (1H, d, J = 5.4 Hz), 9.27 (1H, s) (CDCl₃) | 433 |
| 76 | 1.05 (6H, d, J = 6.9 Hz), 1.74 (3H, s), 3.14 (1H, dd, J = 10.8, 13.2 Hz), 3.40 (1H, t, J = 2.9, 13.0 Hz), 3.55-3.74 (2H, m), 3.60 (3H, s), 4.02 (1H, td, J = 2.1, 11.4 Hz), 4.20 (1H, dd, J = 11.7, 18.0 Hz), 4.80 (1H, dd, J = 2.1, 10.5 Hz), 5.02 (1H, q, J = 6.9 Hz), 6.71 (1H, s), 7.15 (2H, d, J = 8.4 Hz), 7.48 (2H, d, J = 8.4 Hz), 7.80 (2H, d, J = 6.0 Hz), 8.73 (2H, d, J = 6.0 Hz) (CDCl₃) | 448 |
| 77 | 1.05 (6H, d, J = 6.8 Hz), 1.74 (3H, s), 3.14 (1H, dd, J = 10.6, 12.8 Hz), 3.35 (1H, td, J = 2.9, 11.4 Hz), 3.54-3.71 (2H, m), 3.61 (3H, s), 4.03 (1H, td, J = 2.4, 11.6 Hz), 4.20 (1H, dd, J = 11.7, 18.0 Hz), 4.80 (1H, dd, J = 2.1, 10.6 Hz), 5.03 (1H, q, J = 6.8 Hz), 7.15 (2H, d, J = 8.3 Hz), 7.27 (1H, s), 7.48 (2H, d, J = 8.3 Hz), 8.15 (1H, dd, J = 1.1, 5.2 Hz), 8.88 (1H, d, J = 5.1 Hz), 9.28 (1H, d, J = 1.2 Hz) (CDCl₃) | 449 |
| 78 | 1.23 (9H, s), 3.09 (1H, dd, J = 10.5, 12.9 Hz), 3.27 (1H, td, J = 3.0, 12.0 Hz), 3.51-3.64 (2H, m), 3.58 (3H, s), 3.99 (1H, td, J = 2.1, 11.4 Hz), 4.18 (1H, dd, J = 11.7, 18.0 Hz), 4.70 (1H, dd, J = 2.1, 10.5 Hz), 6.70 (1H, s), 7.33 (1H, br.s), 7.38 (2H, d, J = 8.4 Hz), 7.57 (2H, d, J = 8.4 Hz), 7.78 (2H, d, J = 6.0 Hz), 8.70 (2H, d, J = 5.7 Hz) (CDCl₃) | 448 |

TABLE 4-continued

| Compound No. | ¹H-NMR δ: | LC-MS (M + 1) |
|---|---|---|
| 79 | 1.23 (9H, s), 3.09 (1H, dd, J = 10.5, 12.9 Hz), 3.27 (1H, td, J = 3.0, 12.0 Hz), 3.51-3.64 (2H, m), 3.58 (3H, s), 3.99 (1H, td, J = 2.1, 11.4 Hz), 4.18 (1H, dd, J = 11.7, 18.0 Hz), 4.70 (1H, dd, J = 2.1, 10.5 Hz), 7.34 (1H, s), 7.40 (2H, d, J = 12.3 Hz), 7.43 (1H, br.s), 7.59 (2H, d, J = 12.3 Hz), 8.13 (1H, d, J = 5.4 Hz), 8.86 (1H, d, J = 5.1 Hz), 9.27 (1H, d, J = 1.5 Hz) (CDCl₃) | 449 |
| 80 | 1.62-1.68 (5H, m), 1.89 (6H, m), 2.04-2.11 (3H, m), 3.10-3.73 (6H, m), 3.56 (3H, s), 3.96 (1H, t, J = 12.6 Hz), 4.14 (1H, d, J = 11.7 Hz), 4.60 (1H, d, J = 9.9 Hz), 6.69 (1H, s), 6.79 (2H, d, J = 6.6 Hz), 7.17 (2H, d, J = 7.0 Hz), 7.80 (2H, br.d), 8.71 (2H, br.d) (CDCl₃) | 498 |
| 81 | 1.63-1.67 (5H, m), 1.84-1.90 (6H, m), 2.12 (3H, m), 3.14 (1H, dd, J = 10.5, 12.9 Hz), 3.29 (1H, td, J = 3.0, 12.0 Hz), 3.40 (1H, br.s), 3.51-3.62 (2H, m), 3.57 (3H, s), 3.74 (1H, m), 3.97 (1H, td, J = 2.4, 11.8 Hz), 4.13 (1H, dd, J = 2.4, 11.7 Hz), 4.60 (1H, dd, J = 2.1, 10.5 Hz), 6.78 (2H, d, J = 10.8 Hz), 7.18 (2H, d, J = 10.8 Hz), 7.35 (1H, s), 8.16 (1H, dd, J = 1.2, 5.1 Hz), 8.86 (1H, d, J = 5.1 Hz), 9.27 (1H, s) (CDCl₃) | 499 |
| 82 | 1.35-1.67 (12H, m), 2.07 (3H, m), 2.79 (3H, s), 3.14 (1H, dd, J = 10.5, 12.9 Hz), 3.29 (1H, td, J = 3.0, 12.0 Hz), 3.54-3.69 (1H, td, J = 3.0, 12.0 Hz), 3.54-3.69 (2H, m), 3.58 (3H, s), 3.99 (1H, td, J = 2.4, 11.8 Hz), 4.17 (1H, dd, J = 2.4, 11.7 Hz), 4.70 (1H, dd, J = 2.1, 10.5 Hz), 6.70 (1H, s), 7.16 (2H, d, J = 8.1 Hz), 7.30 (2H, d, J = 8.1 Hz), 7.80 (2H, d, J = 6.3 Hz), 8.72 (1H, d, J = 6.3 Hz) (CDCl₃) | 512 |
| 83 | 1.52-1.73 (12H, m), 2.06 (3H, m), 2.78 (3H, s), 3.14 (1H, dd, J = 10.5, 12.9 Hz), 3.29 (1H, td, J = 3.0, 12.0 Hz), 3.53-3.68 (2H, m), 3.59 (3H, s), 3.99 (1H, td, J = 2.4, 11.7 Hz), 4.17 (1H, dd, J = 2.4, 11.7 Hz), 4.68 (1H, dd, J = 2.1, 10.5 Hz), 7.16 (2H, d, J = 8.2 Hz), 7.31 (2H, d, J = 8.2 Hz), 7.35 (1H, s), 8.16 (1H, d, J = 5.3 Hz), 8.88 (1H, d, J = 5.2 Hz), 9.28 (1H, d, J = 1.1 Hz) (CDCl₃) | 513 |
| 84 | 1.58-2.05 (14H, m), 3.15 (1H, dd, J = 10.5, 12.9 Hz), 3.30 (1H, td, J = 3.3, 12.0 Hz), 3.53-3.62 (3H, m), 3.56 (3H, s), 3.97 (1H, td, J = 2.1, 11.8 Hz), 4.00 (1H, m), 4.14 (1H, td, J = 2.1, 4.4 Hz), 4.58 (1H, dd, J = 2.1, 10.5 Hz), 6.59 (2H, d, J = 8.0 Hz), 6.69 (1H, s), 7.19 (2H, d, J = 8.0 Hz), 7.80 (2H, d, J = 6.3 Hz), 8.70 (2H, d, J = 6.3 Hz) (CDCl₃) | 498 |
| 85 | 1.58-2.04 (14H, m), 3.14 (1H, dd, J = 10.8, 12.9 Hz), 3.28 (1H, td, J = 3.0, 12.0 Hz), 3.57-3.61 (3H, m), 3.57 (3H, s), 4.00 (1H, td, J = 2.1, 11.7 Hz), 4.07 (1H, m), 4.14 (1H, td, J = 2.1, 11.4 Hz), 4.57 (1H, dd, J = 1.8, 10.5 Hz), 6.60 (2H, d, J = 8.7 Hz), 7.19 (2H, d, J = 8.7 Hz), 7.34 (1H, s), 8.15 (2H, dd, J = 0.9, 3.1 Hz), 8.86 (1H, d, J = 5.1 Hz), 9.27 (1H, s) (CDCl₃) | 499 |
| 86 | 1.40-1.85 (10H, m), 2.06-2.11 (4H, m), 2.78 (1H, dd, J = 10.5, 12.9 Hz), 3.30 (1H, td, J = 3.3, 12.0 Hz), 3.53-3.62 (3H, m), 3.56 (3H, s), 3.97 (1H, td, J = 2.1, 11.8 Hz), 4.00 (1H, m), 4.14 (1H, td, J = 2.1, 4.4 Hz), 4.58 (1H, dd, J = 2.1, 10.5 Hz), 6.59 (2H, d, J = 8.0 Hz), 6.69 (1H, s), 7.19 (2H, d, J = 8.0 Hz), 7.80 (2H, d, J = 6.3 Hz), 8.70 (2H, d, J = 6.3 Hz) (CDCl₃) | 512 |
| 87 | 1.26-1.86 (10H, m), 2.06-2.11 (4H, m), 2.78 (3H, s), 3.14 (1H, dd, J = 10.8, 13.2 Hz), 3.20 (1H, s), 3.30 (1H, td, J = 3.0, 12.0 Hz), 3.51-3.65 (2H, m), 3.58 (3H, s), 3.99 (1H, td, J = 2.7, 11.4 Hz), 4.14 (1H, td, J = 11.7, 18.0 Hz), 4.60 (1H, dd, J = 2.1, 10.5 Hz), 7.07 (2H, d, J = 11.0 Hz), 7.29 (2H, d, J = 11.0 Hz), 7.35 (1H, s), 8.16 (1H, dd, J = 1.5, 5.4 Hz), 8.87 (1H, d, J = 5.4 Hz), 9.27 (1H, s) (CDCl₃) | 513 |
| 88 | 1.90 (1H, s), 2.24-2.28 (1H, m), 3.14 (1H, dd, J = 10.5, 12.9 Hz), 3.30 (1H, td, J = 3.0, 12.0 Hz), 3.53-3.58 (2H, m), 3.56 (3H, s), 3.84-4.13 (8H, m), 4.60 (1H, dd, J = 2.1, 10.5 Hz), 6.60 (2H, d, J = 8.7 Hz), 6.69 (1H, s), 7.20 (2H, d, J = 8.7 Hz), 7.79 (2H, d, J = 6.3 Hz), 8.70 (2H, d, J = 6.3 Hz) (CDCl₃) | 434 |
| 89 | 1.90 (1H, s), 2.24-2.28 (1H, m), 3.14 (1H, dd, J = 10.5, 12.9 Hz), 3.30 (1H, td, J = 3.0, 12.0 Hz), 3.53-3.58 (2H, m), 3.56 (3H, s), 3.84-4.13 (8H, m), 4.60 (1H, dd, J = 2.1, 10.5 Hz), 6.62 (2H, d, J = 8.7 Hz), 7.32 (2H, d, J = 8.4 Hz), 7.36 (1H, s), 8.15 (1H, d, J = 4.8 Hz), 8.86 (1H, d, J = 5.1 Hz), 9.28 (1H, s) (CDCl₃) | 435 |
| 90 | 1.90-1.96 (1H, m), 2.20-2.25 (1H, m), 2.88 (3H, s), 3.15 (1H, dd, J = 10.8, 12.9 Hz), 3.30 (1H, td, J = 3.0, 12.0 Hz), 3.53-3.64 (2H, m), 3.57 (3H, s), 3.75-4.13 (6H, m), 4.48 (1H, dd, J = 1.8, 10.5 Hz), 6.89 (1H, s), 6.83 (2H, d, J = 8.7 Hz), 7.27 (2H, d, J = 8.7 Hz), 7.80 (2H, d, J = 6.3 Hz), 8.71 (2H, d, J = 6.3 Hz) (CDCl₃) | 448 |
| 91 | 1.90-1.97 (1H, m), 2.20-2.25 (1H, m), 2.88 (3H, s), 3.15 (1H, dd, J = 10.5, 12.9 Hz), 3.51-3.62 (2H, m), 3.58 (3H, s), 3.75-4.13 (7H, m), 4.44 (1H, m), 4.62 (1H, dd, J = 2.1, 10.5 Hz), 6.83 (2H, d, J = 8.7 Hz), 7.29 (2H, d, J = 8.7 Hz), 7.34 (1H, s), 8.15 (1H, dd, J = 1.2, 5.1 Hz), 8.85 (1H, d, J = 5.1 Hz), 9.27 (1H, d, J = 1.2 Hz) (CDCl₃) | 449 |
| 92 | 1.89 (3H, s), 3.12 (1H, dd, J = 10.8, 13.2 Hz), 3.28 (3H, s), 3.30 (1H, td, J = 10.5, 12.9 Hz), 3.54-3.74 (2H, m), 3.60 (3H, | 421 |

TABLE 4-continued

| Compound No. | ¹H-NMR δ: | LC-MS (M + 1) |
|---|---|---|
| | s), 4.02 (1H, td, J = 2.7, 11.4 Hz), 4.19 (1H, dd, J = 11.7, 18.0 Hz), 4.76 (1H, dd, J = 1.8, 10.5 Hz), 7.25 (2H, d, J = 8.4 Hz), 7.36 (1H, s), 7.48 (2H, d, J = 8.4 Hz), 8.13 (1H, d, J = 5.1 Hz), 8.87 (1H, d, J = 5.1 Hz), 9.28 (1H, s) (CDCl$_3$) | |
| 93 | 1.90 (1H, m), 2.85 (1H, m), 2.90-2.93 (2H, m), 3.16 (1H, dd, J = 10.8, 12.9 Hz), 3.54-3.64 (2H, m), 3.57 (3H, s), 4.00 (2H, td, J = 2.1, 11.8 Hz), 4.14 (1H, dd, J = 2.1, 10.5 Hz), 4.62 (1H, dd, J = 2.1, 10.5 Hz), 5.00 (1H, m), 6.69 (1H, s), 6.72 (2H, d, J = 5.5 Hz), 7.25 (2H, d, J = 5.5 Hz), 7.20-7.37 (4H, m), 7.80 (2H, d, J = 6.0 Hz), 8.72 (2H, d, J = 6.0 Hz) (CDCl$_3$) | 480 |
| 94 | 1.92 (1H, m), 2.59 (1H, m), 2.88-3.03 (2H, m), 3.12-3.29 (2H, m), 3.34-3.63 (2H, m), 3.59 (3H, s), 4.01 (1H, t, J = 8.7 Hz), 4.16 (1H, d, J = 12.7 Hz), 4.61 (1H, d, J = 10.5 Hz), 5.03 (1H, m), 6.74 (2H, d, J = 8.4 Hz), 7.25 (2H, d, J = 8.4 Hz), 7.24-7.37 (6H, m), 8.16 (1H, d, J = 5.1 Hz), 8.87 (1H, d, J = 5.1 Hz), 9.28 (1H, s) (CDCl$_3$) | 481 |
| 95 | 2.04-2.31 (2H, m), 2.13 (3H, s), 2.94 (3H, s), 3.10-3.61 (7H, m), 3.57 (3H, s), 3.94-4.18 (2H, m), 4.62 (1H, m), 5.43 (1H, m), 6.58 (2H, m), 7.28 (2H, m), 7.34 (1H, s), 8.14 (1H, d, J = 4.8 Hz), 8.85 (1H, d, J = 5.1 Hz), 9.27 (1H, s) (CDCl$_3$) | 490 |
| 96 | 2.64 (4H, t, J = 4.5 Hz), 3.10 (1H, dd, J = 10.5, 12.9 Hz), 3.16 (2H, s), 3.30 (1H, td, J = 10.5, 12.9 Hz), 3.53-3.66 (2H, m), 3.58 (3H, s), 3.79 (4H, t, J = 4.5 Hz), 3.99 (1H, t, J = 11.7 Hz), 4.18 (1H, d, J = 9.3 Hz), 4.72 (1H, d, J = 10.5 Hz), 6.71 (1H, s), 7.32 (2H, d, J = 8.7 Hz), 7.40 (2H, d, J = 8.7 Hz), 7.79 (2H, d, J = 6.0 Hz), 8.71 (2H, d, J = 6.0 Hz), 9.11 (1H, br.s) (CDCl$_3$) | 491 |
| 97 | 2.66 (4H, t, J = 4.5 Hz), 3.11 (1H, dd, J = 10.0, 12.7 Hz), 3.15 (2H, s), 3.32 (1H, td, J = 10.5, 12.9 Hz), 3.50-3.66 (2H, m), 3.60 (3H, s), 3.79 (4H, t, J = 4.5 Hz), 3.99 (1H, t, J = 11.7 Hz), 4.18 (1H, d, J = 9.0 Hz), 4.72 (1H, d, J = 10.5 Hz), 6.71 (1H, s), 7.32 (2H, d, J = 8.7 Hz), 7.40 (2H, d, J = 8.7 Hz), 8.13 (1H, d, J = 5.1 Hz), 8.87 (1H, d, J = 5.1 Hz), 9.28 (1H, s) (CDCl$_3$) | 492 |
| 98 | 2.36 (3H, s), 2.53-2.67 (8H, s), 3.11 (1H, dd, J = 10.0, 12.7 Hz), 3.16 (2H, s), 3.34 (1H, t, J = 9.0 Hz), 3.47-3.61 (2H, m), 3.57 (3H, s), 3.99 (1H, t, J = 11.8 Hz), 4.17 (1H, d, J = 11.8 Hz), 4.72 (1H, d, J = 8.3 Hz), 6.70 (1H, s), 7.39 (2H, d, J = 8.5 Hz), 7.61 (2H, d, J = 8.4 Hz), 7.80 (2H, d, J = 6.2 Hz), 8.71 (2H, d, J = 6.2 Hz), 9.18 (1H, br.s) (CDCl$_3$) | 504 |
| 99 | 2.34 (3H, s), 2.52-2.67 (8H, s), 3.12 (1H, dd, J = 10.0, 12.7 Hz), 3.16 (2H, s), 3.29 (1H, td, J = 12.3, 2.7 Hz), 3.52-3.71 (2H, m), 3.59 (3H, s), 4.00 (1H, t, J = 9.6 Hz), 4.18 (1H, d, J = 11.4 Hz), 4.72 (1H, d, J = 8.7 Hz), 7.32 (1H, s), 7.38 (2H, d, J = 8.3 Hz), 7.61 (2H, d, J = 8.3 Hz), 8.14 (1H, d, J = 4.8 Hz), 8.86 (1H, d, J = 5.1 Hz), 9.19 (1H, br.s), 9.28 (1H, s) (CDCl$_3$) | 505 |
| 100 | 2.81 (4H, t, J = 5.1 Hz), 3.10 (1H, dd, J = 10.8, 13.2 Hz), 3.23 (2H, s), 3.28 (4H, t, J = 5.1 Hz), 3.40 (1H, m), 3.52-3.66 (2H, m), 3.57 (3H, s), 3.99 (1H, td, J = 2.1, 11.8 Hz), 4.15 (1H, d, J = 11.4 Hz), 4.72 (1H, dd, J = 2.1, 10.5 Hz), 6.70 (1H, s), 6.90-6.98 (4H, m), 7.30 (1H, d, J = 7.8 Hz), 7.40 (2H, d, J = 8.7 Hz), 7.62 (2H, d, J = 8.4 Hz), 7.79 (2H, d, J = 6.3 Hz), 8.71 (2H, d, J = 6.3 Hz), 9.19 (1H, br.s) (CDCl$_3$) | 566 |
| 101 | 2.81 (4H, t, J = 4.9 Hz), 3.10 (1H, dd, J = 10.2, 12.8 Hz), 3.23 (2H, s), 3.28 (4H, t, J = 4.9 Hz), 3.30 (1H, m), 3.51-3.67 (2H, m), 3.59 (3H, s), 3.99 (1H, td, J = 2.1, 11.8 Hz), 4.15 (1H, d, J = 11.4 Hz), 4.72 (1H, dd, J = 2.1, 10.5 Hz), 6.91-6.98 (4H, m), 7.26-7.41 (4H, m), 7.61 (2H, d, J = 8.6 Hz), 8.14 (1H, d, J = 6.2 Hz), 8.86 (1H, d, J = 5.1 Hz), 9.20 (1H, br.s), 9.27 (1H, br.s) (CDCl$_3$) | 567 |
| 201 | 1.90-2.14 (6H, m), 2.95-3.18 (8H, m), 3.46 (3H, s), 3.65-3.69 (2H, m), 3.87-3.91 (1H, m), 4.03-4.07 (3H, m), 4.68 (1H, dd, J = 1.2 Hz, 10.2 Hz), 6.84 (1H, s), 6.96 (2H, d, J = 7.2 Hz), 7.38 (2H, d, J = 7.2 Hz), 7.96 (2H, d, J = 4.2 Hz), 8.68 (2H, d, J = 4.2 Hz) (CDCl$_3$) | 476 |
| 202 | 1.94-2.17 (6H, m), 2.97-3.18 (8H, m), 3.50 (3H, s), 3.67-3.72 (2H, m), 3.86-3.90 (1H, m), 4.03-4.09 (3H, m), 4.68 (1H, dd, J = 1.2 Hz, 10.2 Hz), 6.96 (2H, d, J = 7.2 Hz), 7.00 (1H, s), 7.38 (2H, d, J = 7.2 Hz), 8.19 (1H, dd, J = 1.2 Hz, 4.2 Hz), 8.99 (1H, d, J = 4.2 Hz), 9.30 (1H, d, J = 1.2 Hz) (CDCl$_3$) | 477 |
| 203 | 1.41-1.44 (2H, m), 1.48-1.58 (4H, m), 1.82-1.87 (2H, m), 2.32-2.39 (6H, m), 2.97-3.05 (1H, m), 3.17-3.20 (1H, m), 3.45 (3H, s), 3.64-3.69 (2H, m), 3.86-3.90 (1H, m), 3.97-4.01 (3H, m), 4.67 (1H, dd, J = 1.2 Hz, 10.2 Hz), 6.84 (1H, s), 6.93 (2H, d, J = 7.2 Hz), 7.35 (2H, d, J = 7.2 Hz), 7.96 (2H, d, J = 4.2 Hz), 8.69 (2H, d, J = 4.2 Hz) (CDCl$_3$) | 490 |
| 204 | 1.41-1.44 (2H, m), 1.52-1.60 (4H, m), 1.92-1.96 (2H, m), 2.52-2.83 (6H, m), 2.97-3.05 (1H, m), 3.17-3.20 (1H, m), 3.49 (3H, s), | 491 |

TABLE 4-continued

| Compound No. | $^1$H-NMR δ: | LC-MS (M + 1) |
|---|---|---|
|  | 3.67-3.72 (2H, m), 3.86-3.90 (1H, m), 3.97-4.07 (3H, m), 4.67 (1H, dd, J = 1.2 Hz, 10.2 Hz), 6.93 (2H, d, J = 7.2 Hz), 7.00 (1H, s), 7.36 (2H, d, J = 7.2 Hz), 8.20 (1H, dd, J = 1.2 Hz, 4.2 Hz), 8.99 (1H, d, J = 4.2 Hz), 9.29 (1H, d, J = 1.2 Hz) (CDCl$_3$) |  |
| 205 | 1.83-1.88 (2H, m), 2.14 (3H, s), 2.31-2.45 (9H, m), 2.98-3.05 (1H, m), 3.13-3.20 (1H, m), 3.26-3.30 (1H, m), 3.45 (3H, s), 3.67-3.69 (2H, m), 3.86-3.88 (1H, m), 3.97-4.02 (3H, m), 4.67 (1H, dd, J = 1.2 Hz, 10.2 Hz), 6.84 (1H, s), 6.93 (2H, d, J = 7.2 Hz), 7.35 (2H, d, J = 7.2 Hz), 7.96 (2H, d, J = 4.2 Hz), 8.68 (2H, d, J = 4.2 Hz) (CDCl$_3$) | 505 |
| 206 | 1.83-1.88 (2H, m), 2.14 (3H, s), 2.31-2.45 (9H, m), 2.98-3.05 (1H, m), 3.14-3.20 (1H, m), 3.26-3.30 (1H, m), 3.47 (3H, s), 3.67-3.72 (2H, m), 3.86-3.90 (1H, m), 3.97-4.02 (3H, m), 4.67 (1H, dd, J = 1.2 Hz, 10.2 Hz), 6.93 (2H, d, J = 7.2 Hz), 7.00 (1H, s), 7.36 (2H, d, J = 7.2 Hz), 8.20 (1H, dd, J = 1.2 Hz, 4.2 Hz), 8.99 (1H, d, J = 4.2 Hz), 9.29 (1H, d, J = 1.2 Hz) (CDCl$_3$) | 506 |
| 207 | 1.19-1.50 (5H, m), 1.57-1.79 (3H, m), 2.03-2.06 (2H, m), 3.08 (1H, dd, J = 12.9, 10.5 Hz), 3.16 (1H, m), 3.53-3.58 (1H, m), 3.58 (3H, s), 3.65-3.69 (1H, m), 3.97-4.04 (2H, m), 4.18-4.21 (1H, m), 4.80 (1H, d, J = 10.5 Hz), 5.95 (1H, d, J = 8.4 Hz), 6.71 (1H, s), 7.48 (2H, d, J = 8.1 Hz), 7.77-7.80 (4H, m), 8.71 (2H, d, J = 6.0 Hz) (CDCl$_3$) | 474 |
| 208 | 1.22-1.47 (5H, m), 1.63-1.79 (3H, m), 2.03-2.06 (2H, m), 3.07 (1H, dd, J = 12.9, 10.5 Hz), 3.16 (1H, m), 3.52-3.59 (1H, m), 3.59 (3H, s), 3.61-3.67 (1H, m), 3.96-4.01 (2H, m), 4.18-4.21 (1H, m), 4.79 (1H, dd, J = 10.5, 2.1 Hz), 5.95 (1H, d, J = 7.8 Hz), 7.36 (1H, s), 7.48 (2H, d, J = 8.4 Hz), 7.79 (2H, d, J = 8.4 Hz), 8.11 (1H, dd, J = 5.1, 1.2 Hz), 8.86 (1H, d, J = 5.4 Hz), 9.28 (1H, d, J = 1.2 Hz) (CDCl$_3$) | 475 |
| 209 | 3.09 (1H, dd, J = 12.9, 10.8 Hz), 3.31 (1H, m), 3.46-3.53 (1H, m), 3.58 (3H, s), 3.65-3.70 (3H, m), 3.84-3.87 (2H, m), 4.00 (1H, m), 4.18-4.21 (1H, m), 4.81 (1H, d, J = 8.4 Hz), 6.61 (1H, m), 6.71 (1H, s), 7.50 (2H, d, J = 8.4 Hz), 7.75 (2H, d, J = 6.0 Hz), 7.84 (2H, d, J = 8.4 Hz), 8.71 (2H, d, J = 6.0 Hz) (CDCl$_3$) | 436 |
| 210 | 3.08 (1H, dd, J = 12.9, 10.8 Hz), 3.29 (1H, m), 3.52-3.56 (1H, m), 3.59 (3H, s), 3.63-3.68 (3H, m), 3.83-3.88 (2H, m), 4.01 (1H, m), 4.18-4.21 (1H, m), 4.81 (1H, dd, J = 12.9, 2.4 Hz), 6.65 (1H, m), 7.36 (1H, s), 7.51 (2H, d, J = 8.4 Hz), 7.84 (2H, d, J = 8.4 Hz), 8.10 (1H, dd, J = 5.7, 1.5 Hz), 8.86 (1H, d, J = 5.1 Hz), 9.27 (1H, d, J = 1.2 Hz) (CDCl$_3$) | 437 |
| 211 | 2.99-3.14 (7H, m), 3.31 (1H, m), 3.54-3.58 (1H, m), 3.58 (3H, s), 3.64-3.69 (1H, m), 4.00 (1H, m), 4.17-4.22 (1H, m), 4.81 (1H, d, J = 10.5, 2.1 Hz), 6.71 (1H, s), 7.46 (4H, s), 7.79 (2H, d, J = 4.8 Hz, 1.5 Hz), 8.71 (2H, dd, J = 4.8 Hz, 1.5 Hz) (CDCl$_3$) | 420 |
| 212 | 2.99-3.14 (7H, m), 3.28 (1H, m), 3.53-3.57 (1H, m), 3.59 (3H, s), 3.61-3.66 (1H, m), 4.01 (1H, m), 4.17-4.22 (1H, m), 4.77 (1H, d, J = 10.5, 2.4 Hz), 7.37 (1H, s), 7.47 (4H, s), 8.14 (1H, dd, J = 5.4 Hz, 1.5 Hz), 8.88 (1H, d, J = 5.1 Hz), 9.28 (1H, s). (CDCl$_3$) | 421 |
| 213 | 2.99 (3H, s), 3.09 (1H, t, J = 11.9 Hz), 3.38 (2H, m), 3.59 (3H, s), 3.67 (1H, d, J = 11.7 Hz), 4.01 (1H, t, J = 11.6 Hz), 4.19 (1H, d, J = 11.7 Hz), 4.73 (1H, d, J = 10..2 Hz), 5.32 (1H, s), 6.72 (1H, s), 7.28 (2H, d, J = 8.4 Hz), 7.40 (2H, d, J = 8.4 Hz), 7.86 (2H, d, J = 4.8 Hz), 8.66 (2H, d, J = 4.8 Hz) (CDCl$_3$) | 442 |
| 214 | 3.04 (3H, s), 3.10 (1H, dd, J = 10.8 Hz, 12.8 Hz), 3.29 (1H, td, J = 3.0 Hz, 12.0 Hz), 3.52-3.65 (2H, m), 3.59 (3H, s), 4.00 (1H, td, J = 2.4 Hz, 11.0 Hz), 4.18 (1H, dd, J = 1.8 Hz, 11.4 Hz), 4.73 (1H, dd, J = 2.1 Hz, 10.5 Hz), 6.67 (1H, br.s), 7.26-7.29 (3H, m), 7.42 (2H, d, J = 8.4 Hz), 8.14 (1H, dd, J = 1.2 Hz, 5.1 Hz), 8.87 (1H, d, J = 5.1 Hz), 9.28 (1H, d, J = 1.2 Hz) (CDCl$_3$) | 443 |
| 215 | 1.50 (2H, m), 1.67 (4H, t, J = 5.7 Hz), 2.54 (4H, m), 3.08 (2H, s), 3.11 (1H, dd, J = 2.4 Hz, 13.2 Hz), 3.30 (1H, td, J = 3.0 Hz, 11.9 Hz), 3.53-3.66 (2H, m), 3.58 (3H, s), 3.99 (1H, t, J = 2.4 Hz, 11.6 Hz), 4.16 (1H, dd, J = 1.5 Hz, 11.7 Hz), 4.71 (1H, dd, J = 1.8 Hz, 10.2 Hz), 6.70 (1H, s), 7.39 (2H, d, J = 8.7 Hz), 7.62 (2H, d, J = 8.4 Hz), 7.79 (2H, d, J = 6.0 Hz), 8.71 (2H, d, J = 6.3 Hz), 9.33 (1H, br.s) (CDCl$_3$) | 489 |
| 216 | 1.51 (2H, m), 1.60-1.67 (4H, m), 2.55 (4H, m), 3.04 (2H, s), 3.11 (1H, dd, J = 2.4 Hz, 13.2 Hz), 3.29 (1H, td, J = 3.0 Hz, 11.9 Hz), 3.51-3.63 (2H, m), 3.58 (3H, s), 3.99 (1H, t, J = 2.4 Hz, 11.6 Hz), 4.17 (1H, dd, J = 1.5 Hz, 11.7 Hz), 4.71 (1H, dd, J = 1.8 Hz, 10.2 Hz), 6.89 (1H, s), 7.38 (2H, d, J = 8.7 Hz), 7.61 (2H, d, J = 8.7 Hz), 7.95 (1H, d, J = 5.1 Hz), 8.51 (1H, d, J = 4.8 Hz), 8.55 (1H, d, J = 3.0 Hz), 9.34 (1H, br.s) (CDCl$_3$) | 490 |
| 217 | 1.85 (4H, m), 2.27 (4H, m), 3.10 (1H, dd, J = 10.8 Hz, 12.9 Hz), 3.29 (2H, s), 3.33 (1H, m), 3.53-3.66 (2H, m), 3.62 (3H, s), 3.99 (1H, td, J = 2.1 Hz, 11.7 Hz), 4.18 (1H, dd, J = 2.4 Hz, 12.0 Hz), 4.71 (1H, dd, J = 2.1 Hz, 10.5 Hz), 6.70 (1H, s), 7.38 (2H, d, J = 8.4 Hz), 7.62 (2H, d, J = 6.0 Hz), 7.79 (2H, d, J = 3.0 Hz), 8.71 (2H, d, J = 6.3 Hz), 9.16 (1H, br.s) (CDCl$_3$) | 475 |
| 218 | 1.87 (4H, m), 2.70 (4H, m), 3.09 (1H, dd, J = 10.8 Hz, 12.9 Hz), 3.28 (1H, m), 3.30 (2H, s), 3.58-3.67 (2H, m), 3.59 (3H, s), 4.00 (1H, td, J = 2.1 Hz, 11.7 Hz), 4.16 (1H, dd, J = 2.4 Hz, 12.0 Hz), 4.71 (1H, dd, J = 2.1 Hz, 10.5 Hz), 7.26 (1H, s), 7.35 (2H, d, J = 8.7 Hz), 7.62 (2H, d, | 476 |

TABLE 4-continued

| Compound No. | ¹H-NMR δ: | LC-MS (M + 1) |
|---|---|---|
| | J = 8.7 Hz), 8.13 (1H, d, J = 6.3 Hz), 8.86 (1H, d, J = 5.1 Hz), 9.16 (1H, br.s), 9.28 (1H, s) (CDCl₃) | |
| 219 | 2.39 (6H, s), 3.06-3.14 (1H, m), 3.09 (2H, s), 3.31 (1H, td, J = 3.0 Hz, 12.0 Hz), 3.53-3.66 (2H, m), 3.57 (3H, s), 3.96 (1H, td, J = 2.0 Hz, 11.3 Hz), 4.17 (1H, d, J = 9.7 Hz), 4.71 (1H, dd, J = 2.6 Hz, 10.5 Hz), 6.70 (1H, s), 7.39 (2H, d, J = 8.4 Hz), 7.63 (2H, d, J = 8.5 Hz), 7.79 (2H, d, J = 6.1 Hz), 8.71 (2H, d, J = 6.0 Hz), 9.16 (1H, br.s) (CDCl₃) | 449 |
| 220 | 2.39 (6H, s), 3.07-3.14 (1H, m), 3.09 (2H, s), 3.28 (1H, td, J = 3 Hz, 12 Hz), 3.52-3.64 (2H, m), 3.59 (3H, s), 4.00 (1H, td, J = 3.2 Hz, 11.3 Hz), 4.17 (1H, d, J = 9.7 Hz), 4.71 (1H, dd, J = 2.1 Hz, 10.5 Hz), 7.26 (1H, s), 7.39 (2H, d, J = 8.4 Hz), 7.63 (2H, d, J = 8.5 Hz), 8.14 (1H, dd, J = 1.4 Hz, 5.4 Hz), 8.86 (1H, d, J = 5.1 Hz), 9.17 (1H, br.s), 9.27 (1H, d, J = 1.2 Hz) (CDCl₃) | 450 |
| 221 | 3.09 (1H, dd, J = 12.9, 10.5 Hz), 3.31 (1H, m), 3.53-3.58 (1H, m), 3.58 (3H, s), 3.67-3.71 (1H, m), 4.01 (1H, ddd, J = 11.7 Hz, 11.7 Hz, 2.4 Hz), 4.18-4.22 (1H, m), 4.82 (1H, dd, J = 10.5 Hz, 2.1 Hz), 6.71 (1H, s), 7.52 (2H, d, J = 8.1 Hz), 7.79 (2H, dd, J = 4.5 Hz, 1.5 Hz), 7.86 (2H, d, J = 8.1 Hz), 8.72 (2H, dd, J = 4.5, 1.5 Hz) (CDCl₃) | 392 |
| 222 | 3.09 (1H, dd, J = 12.8 Hz, 10.7 Hz), 3.29 (1H, ddd, J = 12.3 Hz, 12.3 Hz, 3.1 Hz), 3.53-3.57 (1H, m), 3.60 (3H, s), 3.64-3.69 (1H, m), 4.02 (1H, ddd, J = 11.7 Hz, 11.7 Hz, 2.3 Hz), 4.21 (1H, dd, J = 12.6 Hz, 2.0 Hz), 4.81 (1H, dd, J = 10.4 Hz, 1.9 Hz), 7.36 (1H, s), 7.52 (2H, d, J = 8.1 Hz), 7.87 (2H, d, J = 8.1 Hz), 8.12 (1H, d, J = 5.3 Hz), 8.86 (1H, d, J = 5.1 Hz), 9.28 (1H, s) (CDCl₃) | 393 |
| 223 | 2.30 (3H, s), 2.64-2.80 (8H, m), 2.82 (2H, t, J = 7.2 Hz), 3.11-3.15 (1H, m), 3.26-3.32 (1H, m), 3.53-3.63 (2H, m), 3.59 (3H, s), 3.98-4.02 (1H, m), 4.10-4.18 (3H, m), 4.67 (1H, dd, J = 1.2 Hz, 10.2 Hz), 6.93 (1H, s), 6.94 (2H, d, J = 7.2 Hz), 7.31 (2H, d, J = 7.2 Hz), 7.78 (2H, d, J = 4.2 Hz), 8.71 (2H, d, J = 4.2 Hz) (CDCl₃) | 491 |
| 224 | 1.52-1.93 (6H, m), 3.11 (1H, dd, J = 12.9, 10.5 Hz), 3.30-3.37 (3H, m), 3.54-3.58 (1H, m), 3.58 (3H, s), 3.65-3.74 (3H, m), 4.00 (1H, m), 4.19 (1H, dd, J = 11.7, 2.1 Hz), 4.78 (1H, dd, J = 10.5, 2.1 Hz), 6.71 (1H, s), 7.38-7.45 (4H, m), 7.79 (2H, d, J = 5.4 Hz), 8.72 (2H, m) (CDCl₃) | 460 |
| 225 | 1.60-1.69 (6H, m), 3.10 (1H, dd, J = 12.9, 10.5 Hz), 3.27-3.35 (3H, m), 3.52-3.57 (1H, m), 3.59 (3H, s), 3.61-3.67 (3H, m), 4.01 (1H, m), 4.17-4.19 (1H, m), 4.78 (1H, dd, J = 10.5, 2.4 Hz), 7.36 (1H, s), 7.41-7.48 (4H, m), 8.13 (1H, dd, J = 5.1, 1.2 Hz), 8.88 (1H, d, J = 5.1 Hz), 9.28 (1H, d, J = 1.2 Hz) (CDCl₃) | 461 |
| 226 | 3.04 (1H, dd, J = 10.5 Hz, 12.6 Hz), 3.27 (1H, td, J = 11.7 Hz, 2.4 Hz), 3.48-3.58 (2H, m), 3.50 (3H, s), 3.97 (1H, td, J = 2.1 Hz, 11.7 Hz), 4.18 (1H, dd, J = 11.8 Hz, 2.1 Hz), 4.67 (1H, d, J = 10.5 Hz), 7.11 (1H, br.s), 7.13 (2H, d, J = 8.4 Hz), 7.27-7.55 (6H, m), 7.80 (2H, d, J = 7.2 Hz), 8.12 (1H, dd, J = 1.2 Hz, 5.1 Hz), 8.87 (1H, d, J = 5.1 Hz), 9.27 (1H, d, J = 0.9 Hz) (CDCl₃) | 505 |
| 227 | 3.07 (1H, m), 3.14 (3H, d, J = 4.4 Hz), 3.30 (1H, t, J = 11.8 Hz), 3.48-3.58 (2H, m), 3.50 (3H, s), 4.00 (1H, t, J = 11.6 Hz), 4.18 (1H, d, J = 11.6 Hz), 4.75 (1H, d, J = 10.4 Hz), 6.09 (1H, br.s), 6.71 (1H, s), 7.26 (2H, d, J = 7.5 Hz), 7.49 (2H, d, J = 8.1 Hz), 7.78 (1H, d, J = 5.5 Hz), 7.93 (1H, br.s), 8.71 (2H, d, J = 5.7 Hz) (CDCl₃). | 437 |
| 228 | 3.11 (1H, dd, J = 12.9 Hz, 10.8 Hz), 3.32 (1H, td, J = 3.0 Hz, 12.0 Hz), 3.52-3.67 (2H, m), 3.58 (3H, s), 3.99 (1H, td, J = 2.1 Hz, 11.7 Hz), 4.17 (1H, d, J = 11.7 Hz), 4.73 (1H, dd, J = 1.5 Hz, 9.9 Hz), 6.71 (1H, s), 7..25-7.47 (8H, m), 7.72 (1H, br.s), 7.78 (2H, d, J = 6.0 Hz), 8.70 (2H, d, J = 6.0 Hz) (CDCl₃). | 499 |
| 229 | 3.11 (1H, dd, J = 12.9 Hz, 10.5 Hz), 3.14 (3H, d, J = 4.5 Hz), 3.30 (1H, td, J = 12..0 Hz, 3.0 Hz), 3.53-3.67 (2H, m), 3.59 (3H, s), 4.01 (1H, td, J = 2.4 Hz, 12.0 Hz), 4.18 (1H, dd, J = 2.1 Hz, 11.7 Hz), 4.75 (1H, dd, J = 2.1 Hz, 10.5 Hz), 6.11 (1H, br.s), 7.28 (2H, d, J = 8.4 Hz), 7.35 (1H, s), 7.50 (2H, d, J = 8.4 Hz), 8.00 (1H, d, J = 6.6 Hz), 8.12 (1H, d, J = 5.4 Hz), 8.87 (1H, d, J = 5.1 Hz), 9.27 (1H, d, J = 1.2 Hz) (CDCl₃). | 438 |
| 230 | 3.11 (1H, dd, J = 12.9 Hz, 10.5 Hz), 3.30 (1H, td, J = 12.0 Hz, 3.0 Hz), 3.33-3.67 (2H, m), 3.59 (3H, s), 4.00 (1H, td, J = 2.4 Hz, 12.0 Hz), 4.18 (1H, dd, J = 2.1 Hz, 11.7 Hz), 4.75 (1H, dd, J = 2.1 Hz, 10.5 Hz), 7.26-7.48 (10H, m), 8.15 (1H, d, J = 5.4 Hz), 8.87 (1H, d, J = 5.1 Hz), 9.27 (1H, s) (CDCl₃) | 500 |
| 231 | 3.07-3.14 (1H, m), 3.30-3.34 (1H, m), 3.53-3.65 (5H, m), 3.79 (3H, s), 3.96-4.02 (1H, m), 4.15-4.19 (1H, m), 4.71 (1H, dd, J = 1.2 Hz, 10.2 Hz), 6.70 (1H, s), 6.73 (1H, br.s), 7.26-7.38 (4H, m), 7.79 (2H, d, J = 4.2 Hz), 8.71 (2H, d, J = 4.2 Hz) (DMSO-d6) | 422 |
| 232 | 3.06-3.10 (1H, m), 3.25-3.31 (1H, m), 3.51-3.63 (5H, m), 3.79 (3H, s), 3.96-4.00 (1H, m), 4.16-4.20 (1H, m), 4.69 (1H, dd, J = 1.2 Hz, 10.2 Hz), 6.68 (1H, br), 7.33-7.44 (5H, m), 8.13 (1H, dd, J = 1.2 Hz, 4.2 Hz), 8.86 (1H, d, J = 4.2 Hz), 9.27 (1H, d, J = 1.2 Hz) (DMSO-d6) | 423 |
| 233 | 1.84-1.88 (4H, m), 2.49-2.55 (3H, m), 2.69-2.71 (2H, m), 2.78-2.82 (1H, m), 3.08-3.15 (1H, m), 3.24-3.32 (1H, m), 3.53-3.64 (2H, m), 3.57 (3H, s), 3.99-4.14 (5H, m), 4.68 (1H, dd, J = 1.2 Hz, 10.2 Hz), | 492 |

TABLE 4-continued

| Compound No. | ¹H-NMR δ: | LC-MS (M + 1) |
|---|---|---|
| | 6.95 (1H, s), 6.95 (2H, d, J = 6.8 Hz), 7.33 (2H, d, J = 6.8 Hz), 7.78 (2H, d, J = 4.2 Hz), 8.71 (2H, d, J = 4.2 Hz) (CDCl₃) | |
| 234 | 1.78-1.85 (4H, m), 2.50-2.55 (3H, m), 2.70-2.72 (2h, m), 2.79-2.82 (1H, m), 3.08-3.12 (1H, m), 3.23-3.28 (1H, m), 3.52-5.62 (2H, m), 3.58 (3H, s), 4.00-4.15 (5H, m), 4.67 (1H, dd, J = 1.2 Hz, 10.2 Hz), 6.97 (2H, d, J = 6.8 Hz), 7.32 (2H, d, J = 6.8 Hz), 8.13 (1H, dd, J = 1.2 Hz, 4.2 Hz), 8.86 (1H, d, J = 4.2 Hz), 9.27 (1H, d, J = 1.2 Hz) (CDCl₃) | 493 |
| 235 | 3.06-3.10 (1H, m), 3.24-3.32 (1H, m), 3.48-3.65 (9H, m), 3.73-3.77 (4H, m), 3.96-4.02 (1H, m), 4.12-4.18 (1H, m), 4.68 (1H, dd, J = 1.2 Hz, 10.2 Hz), 6.40 (1H, br), 6.97 (1H, s), 7.34-7.41 (4H, m), 7.78 (2H, d, J = 4.2 Hz), 8.71 (2H, d, J = 4.2 Hz) (CDCl₃) | 477 |
| 236 | 3.06-3.10 (1H, m), 3.18-3.28 (1H, m), 3.48-3.62 (9H, m9, 3.74-3.77 (4H, m), 3.92-4.00 (1H, m), 4.15-4.20 (1H, m), 4.68 (1H, dd, J = 1.2 Hz, 10.2 Hz), 6.43 (1H, br.s), 7.34-7.41 (5H, m), 8.14 (1H, dd, J = 1.2 Hz, 4.2 Hz), 8.86 (1H, d, J = 4.2 Hz), 9.27 (1H, d, J = 1.2 Hz) (CDCl₃) | 478 |
| 237 | 3.04 (6H, s), 3.14-3.18 (1H, m), 3.26-3.34 (1H, m), 3.52-3.64 (5H, m), 3.95-4.01 (1H, m), 4.14-4.18 (1H, m), 4.68 (1H, dd, J = 1.2 Hz, 10.2 Hz), 6.38 (1H, br.s), 6.97 (1H, s), 7.33 (2H, d, J = 7.2 Hz), 7.42 (2H, d, J = 7.2 Hz), 7.80 (2H, d, J = 4.2 Hz), 8.71 (2H, d, J = 4.2 Hz) (CDCl₃) | 435 |
| 238 | 3.05 (6H, s), 3.10-3.14 (1H, m), 3.27-3.34 (1H, m), 3.51-3.62 (5H, m), 3.96-4.02 (1H, m), 4.15-4.20 (1H, m), 4.67 (1H, dd, J = 1.2 Hz, 10.2 Hz), 6.37 (1H, br.s), 7.28-7.43 (5H, m), 8.15 (1H, dd, J = 1.2 Hz, 4.2 Hz), 8.87 (1H, d, J = 4.2 Hz), 9.27 (1H, d, J = 1.2 Hz) (CDCl₃) | 436 |
| 239 | 3.11 (1H, dd, J = 10.8 Hz, 13.2 Hz), 3.31 (1H, td, J = 12.1 Hz, 3.0 Hz), 3.54-3.67 (2H, m), 3.59 (3H, s), 4.00 (1H, td, J = 11.7 Hz, 1.8 Hz), 4.20 (1H, d, J = 11.7 Hz), 4.34 (2H, s), 4.73 (1H, dd, J = 1.8 Hz, 10.5 Hz), 6.72 (1H, br.s), 7.19-7.42 (10H, m), 8.14 (1H, dd, J = 0.9 Hz, 5.1 Hz), 8.86 (1H, d, J = 5.1 Hz), 9.26 (1H, s) (CDCl₃) | 519 |
| 240 | 2.87 (6H, s), 2.99 (1H, dd, J = 10.6 Hz, 13.3 Hz), 3.21 (1H, td, J = 12.1 Hz, 3.0 Hz), 3.47-3.50 (3H, m), 3.55 (3H, s), 3.92 (1H, td, J = 2.1 Hz, 11.7 Hz), 4.11-4.16 (1H, m), 4.59 (1H, dd, J = 1.9 Hz, 10.4 Hz), 7.02 (2H, m), 7.19-7.42 (10H, m), 8.14 (1H, dd, J = 0.9 Hz, 5.1 Hz), 8.86 (1H, d, J = 5.1 Hz), 9.26 (1H, s) (CDCl₃) | 598 |
| 241 | 3.09 (1H, dd, J = 10.6 Hz, 12.8 Hz), 3.28 (1H, td, J = 12.1 Hz, 3.0 Hz), 3.52-3.67 (2H, m), 3.58 (3H, s), 3.92 (1H, td, J = 2.1 Hz, 11.7 Hz), 4.17 (1H, m), 4.75 (1H, dd, J = 2.4 Hz, 10.8 Hz), 7.34 (2H, d, J = 8.7 Hz), 7.51 (1H, d, J = 8.7 Hz), 8.05 (1H, m), 8.10 (1H, br.s), 8.13 (1H, dd, J = 1.2 Hz, 5.1 Hz), 8.43-8.45 (2H, m), 8.51 (2H, dd), 8.86 (1H, d, J = 5.1 Hz), 9.27 (1H, d, J = 1.2 Hz) (CDCl₃) | 501 |
| 242 | 3.05 (1H, dd, J = 10.7 Hz, 12.9 Hz), 3.30 (1H, td, J = 12.2 Hz, 3.0 Hz), 3.51-3.62 (2H, m), 3.56 (3H, s), 3.96 (1H, td, J = 11.4 Hz, 2.0 Hz), 4.00-4.17 (1H, m), 4.67 (1H, dd, J = 1.9 Hz, 10.4 Hz), 6.71 (1H, s), 7.13 (2H, d, J = 8.6 Hz), 7.27 (2H, d, d, J = 8.6 Hz), 7.41-7.46 (3H, m), 7.54 (1H, t, J = 7.4 Hz), 7.78-7.80 (4H, m), 8.71 (2H, d, J = 6.0 Hz) (CDCl₃). | 504 |
| 243 | 3.11 (1H, dd, J = 10.8 Hz, 13.2 Hz), 3.31 (1H, td, J = 12.1 Hz, 3.0 Hz), 3.54-3.67 (2H, m), 3.59 (3H, s), 4.00 (1H, td, J = 11.7 Hz, 7.8 Hz), 4.20 (1H, d, J = 11.7 Hz), 4.34 (2H, s), 4.73 (1H, dd, J = 9.8 Hz, 10.5 Hz), 6.68 (1H, s), 6.94 (1H, br.s), 7.19-7.41 (9H, m), 7.83 (2H, dd, J = 1.5 Hz, 4.5 Hz), 8.69 (2H, dd, J = 1.2 Hz, 4.5 Hz) (CDCl₃) | 518 |
| 244 | 2.87 (6H, s), 2.97 (1H, dd, J = 10.6 Hz, 13.3 Hz), 3.14 (1H, td, J = 12.1 Hz, 3.0 Hz), 3.46-3.60 (2H, m), 3.53 (3H, s), 3.90 (1H, m), 4.08-4.16 (1H, m), 4.57 (1H, dd, J = 1.9 Hz, 10.4 Hz), 6.70 (1H, s), 7.01 (2H, d, J = 8.7 Hz), 7.17-7.20 (3H, m), 7.45 (1H, t, J = 8.1 Hz), 7.57 (1H, d), 7.76 (2H, dd, J = 1.5 Hz, 4.5 Hz), 8.21 (1H, d, J = 7.8 Hz), 8.33 (1H, d, J = 8.6 Hz), 8.48 (1H, d, J = 7.8 Hz), 8.71 (1H, dd, J = 1.5 Hz, 4.5 Hz) (CDCl₃) | 597 |
| 245 | 3.09 (1H, dd, J = 10.8 Hz, 12.8 Hz), 3.28 (1H, td, J = 7.0 Hz, 12.0 Hz), 3.52-3.67 (2H, m), 3.58 (3H, s), 4.00 (1H, td, J = 12.0 Hz, 3.1 Hz), 4.18 (1H, d, J = 12.0 Hz), 4.75 (1H, dd, J = 2.4 Hz, 10.8 Hz), 6.71 (1H, s), 7.36-7.54 (5H, m), 7.78 (2H, d, J = 4.8 Hz), 7.90 (1H, br.s), 8.10 (1H, d), 8.20 (1H, br.s), 8.47 (1H, d, J = 5.1 Hz), 8.61 (1H, d, J = 2.7 Hz), 8.70 (2H, d, J = 4.8 Hz) (CDCl₃) | 500 |
| 246 | 3.06-3.11 (1H, m), 3.26-3.32 (1H, m), 3.53-3.65 (5H, m), 3.95-3.99 (1H, m), 4.15-4.18 (1H, m), 4.68 (1H, dd, J = 1.2 Hz, 10.2 Hz), 5.21 (2H, s), 6.70 (1H, s), 6.79 (1H, br), 7.35-7.45 (9H, m), 7.80 (2H, d, J = 7.2 Hz), 8.71 (2H, d, J = 7.2 Hz) (CDCl₃) | 498 |
| 247 | 2.63-2.68 (2H, m), 2.97-3.12 (3H, m), 3.22-3.32 (1H, m), 3.54-3.64 (5H, m), 3.98-4.04 (1H, m), 4.14-4.18 (1H, m), 4.68 (1H, dd, J = 1.2 Hz, 10.2 Hz), 4.68 (1H, s), 6.78 (1H, d, J = 7.2 Hz), 7.20-7.26 (2H, m), 7.79 (2H, d, J = 4.2 Hz), 7.97 (1H, br.s), 8.72 (2H, d, J = 4.2 Hz) (CDCl₃) | 418 |
| 248 | 2.63-2.68 (2H, m), 2.98-3.15 (3H, m), 3.21-3.32 (1H, m), 3.53-3.63 (5H, m), 3.96-4.01 (1H, m), 4.15-4.20 (1H, m), 4.66 (1H, dd, J = 1.2 Hz, 10.2 Hz), 6.78 (1H, d, J = 7.2 Hz), 7.21-7.26 (2H, m), | 419 |

TABLE 4-continued

| Compound No. | $^1$H-NMR δ: | LC-MS (M + 1) |
|---|---|---|
| | 7.36 (1H, s), 7.59 (1H, br.s), 8.13 (1H, dd, J = 1.2 Hz, 4.2 Hz), 8.57 (1H, d, J = 4.2 Hz), 9.28 (1H, d, J = 1.2 Hz) (CDCl$_3$) | |
| 249 | 1.36 (6H, s), 2.50 (2H, s), 3.09-3.16 (1H, m), 3.34-3.39 (1H, m), 3.55-3.67 (5H, m), 3.99-4.05 (1H, m), 4.16-4.20 (1H, m), 4.70 (1H, dd, J = 1.2 Hz, 10.2 Hz), 6.71 (1H, s), 6.79 (1H, d, J = 7.2 Hz), 7.21 (1H, dd, J = 1.2 Hz, 7.2 Hz), 7.34 (1H, d, J = 1.2 Hz), 7.73 (1H, br), 7.78 (2H, d, J = 4.2 Hz), 8.72 (2H, d, J = 4.2 Hz) (CDCl$_3$) | 446 |
| 250 | 1.36 (6H, s), 2.50 (2H, s), 3.08-3.16 (1H, m), 3.32-3.36 (1H, m), 3.51-3.62 (5H, m), 3.97-4.05 (1H, m), 4.17-4.21 (1H, m), 4.71 (1H, dd, J = 1.2 Hz, 10.2 Hz), 6.78 (1H, d, J = 7.2 Hz), 7.22-7.26 (2H, m), 7.35 (1H, s), 7.83 (1H, br.s), 8.13 (1H, dd, J = 1.2 Hz, 4.2 Hz), 8.87 (1H, d, J = 4.2 Hz), 9.28 (1H, d, J = 1.2 Hz) (CDCl$_3$) | 447 |
| 251 | 3.06-3.11 (1H, m), 3.24-3.31 (1H, m), 3.51-3.62 (5H, m), 3.9604.02 (1H, m), 4.16-4.20 (1H, m), 4.67 (1H, dd, J = 1.2 Hz, 10.2 Hz), 5.22 (2H, s), 6.74 (1H, br), 7.26 (1H, s), 7.36-7.45 (9H, m), 8.14 (1H, dd, J = 1.2 Hz, 4.2 Hz), 8.87 (1H, d, J = 4.2 Hz), 9.28 (1H, d, J = 1.2 Hz) (CDCl$_3$) | 499 |
| 252 | 1.31 (3H, t, J = 7.2 Hz), 3.07-3.11 (1H, m), 3.28-3.33 (1H, m), 3.53-3.65 (5H, m), 3.96-4.00 (1H, m), 4.15-4.26 (3H, m), 4.68 (1H, dd, J = 1.2 Hz, 10.2 Hz), 6.70 (1H, s), 6.72 (1H, br.s), 7.36 (2H, d, J = 7.2 Hz), 7.40 (2H, d, J = 7.2 Hz), 7.78 (2H, d, J = 4.2 Hz), 8.72 (2H, d, J = 4.2 Hz) (CDCl$_3$) | 436 |
| 253 | 1.32 (3H, t, J = 7.2 Hz), 3.07-3.10 (1H, m), 3.27-3.31 (1H, m), 3.52-3.63 (5H, m), 3.96-4.01 (1H, m), 4.16-4.27 (3H, m), 4.69 (1H, dd, J = 1.2 Hz, 10.2 Hz), 6.65 (1H, br.s), 7.33-7.44 (5H, m), 8.14 (1H, dd, J = 1.2 Hz, 4.2 Hz), 8.87 (1H, d, J = 4.2 Hz), 9.28 (1H, d, J = 1.2 Hz) (CDCl$_3$) | 437 |
| 254 | 3.11 (1H, dd, J = 12.9 Hz, 10.5 Hz), 3.30-3.43 (1H, m), 3.54-3.58 (1H, m), 3.64 (3H, s), 3.64-3.75 (9H, m), 4.01 (1H, m), 4.17 (1H, m), 4.78 (1H, dd, J = 10.5 Hz, 2.1 Hz), 6.71 (1H, s), 7.44-7.50 (4H, m), 7.79 (2H, dd, J = 5.1 Hz, 1.5 Hz), 8.71 (2H, d, J = 4.8 Hz, 1.5 Hz) (CDCl$_3$) | 461 |
| 255 | 3.09 (1H, dd, J = 12.9 Hz, 10.5 Hz), 3.28 (1H, m), 3.56-3.58 (1H, m), 3.59 (3H, s), 3.61-3.75 (9H, m), 4.02 (1H, m), 4.17 (1H, m), 4.78 (1H, dd, J = 10.5 Hz, 2.1 Hz), 7.36 (1H, s), 7.43-7.51 (4H, m), 8.13 (1H, dd, J = 5.1 Hz, 1.2 Hz), 8.87 (1H, d, J = 5.1 Hz, 2.1 Hz), 9.28 (1H, d, J = 0.9 Hz) (CDCl$_3$) | 462 |
| 256 | 2.16 (3H, s), 2.79 (1H, dd, J = 12.6 Hz, 9.9 Hz), 3.28-3.36 (1H, m), 3.54-3.61 (1H, m), 3.61 (3H, s), 3.81-3.84 (1H, m), 3.84 (3H, s), 4.00 (1H, m), 4.18-4.22 (1H, m), 5.02 (1H, dd, J = 9.6 Hz, 1.8 Hz), 6.69 (1H, s), 6.86 (1H, d, J = 9.0 Hz), 7.09 (1H, m), 7.46 (1H, d, J = 2.4 Hz), 7.60 (1H, dd, J = 8.7 Hz, 2.7 Hz), 7.82 (2H, dd, J = 4.5 Hz, 1.5 Hz), 8.71 (2H, dd, J = 4.8 Hz, 1.5 Hz) (CDCl$_3$) | 436 |
| 257 | 2.17 (3H, s), 2.80 (1H, dd, J = 12.9 Hz, 10.2 Hz), 3.29-3.34 (1H, m), 3.52-3.57 (1H, m), 3.63 (3H, s), 3.79-3.83 (1H, m), 3.85 (3H, s), 4.00 (1H, ddd, J = 12.0 Hz, 12.0 Hz, 2.4 Hz), 4.18 (1H, dd, J = 11.7 Hz, 2.4 Hz), 5.02 (1H, d, J = 14.1 Hz), 6.69 (1H, s), 6.86 (1H, d, J = 8.7 Hz), 7.15 (1H, s), 7.35 (1H, s), 7.48 (1H, d, J = 2.4 Hz), 7.58 (1H, dd, J = 8.7z, 2.7 Hz), 8.20 (1H, dd, J = 5.1, 1.2 Hz), 8.87 (1H, d, J = 5.4 Hz), 9.28 (1H, d, J = 1.2 Hz) (CDCl$_3$) | 437 |
| 258 | 2.19 (3H, s), 3.07-3.14 (1H, m), 3.27-3.46 (1H, m), 3.52-3.57 (1H, m), 3.58 (3H, s), 3.66-3.71 (1H, m), 3.94-4.02 (1H, m), 4.15-4.19 (1H, m), 4.74 (1H, d, J = 9.6 Hz), 6.70 (1H, s), 7.16 (1H, m), 7.31-7.40 (3H, m), 7.71 (1H, s), 7.80 (2H, d, J = 3.9 Hz), 8.72 (2H, d, J = 3.9 Hz) (CDCl$_3$) | 406 |
| 259 | 2.20 (3H, s), 3.10 (1H, dd, J = 13.2 Hz, 10.5 Hz), 3.29-3.34 (1H, m), 3.50-3.54 (1H, m), 3.62 (3H, s), 3.72-3.79 (1H, m), 3.98 (1H, ddd, J = 11.7 Hz, 11.7 Hz, 2.4 Hz), 4.11 (1H, m), 4.76 (1H, dd, J = 10.5, 2.1 Hz), 7.16-7.21 (2H, m), 7.35-7.38 (3H, m), 7.76 (1H, s), 8.18 (1H, d, J = 5.4 Hz), 8.91 (1H, d, J = 5.4 Hz), 9.28 (1H, d, J = 0.9 Hz) (CDCl$_3$) | 407 |
| 260 | 1.23 (6H, t, J = 7.2 Hz), 3.06-3.13 (1H, m), 3.28-3.42 (5H, m), 3.52-3.63 (5H, m), 3.94-4.00 (1H, m), 4.14-4.18 (1H, m), 4.70 (1H, dd, J = 1.2 Hz, 10.2 Hz), 6.38 (1H, br.s), 6.70 (1H, s), 7.30 (2H, d, J = 7.2 Hz), 7.41 (2H, d, J = 7.2 Hz), 7.79 (2H, d, J = 4.2 Hz), 8.71 (2H, d, J = 4.2 Hz) (CDCl$_3$) | 463 |
| 261 | 1.24 (6H, t, J = 7.3 Hz), 3.06-3.13 (1H, m), 3.26-3.42 (5H, m), 3.51-3.62 (5H, m), 3.96-4.00 (1H, m), 4.14-4.17 (1H, m), 4.68 (1H, dd, J = 1.2 Hz, 10.2 Hz), 6.31 (1H, br.s), 7.32-7.38 (3H, m), 7.43 (2H, d, J = 7.2 Hz), 8.14 (1H, dd, J = 1.2 Hz, 4.2 Hz), 8.87 (1H, d, J = 4.2 Hz), 9.27 (1H, d, J = 1.2 Hz) (CDCl$_3$) | 464 |
| 262 | 3.08-3.13 (1H, m), 3.28-3.33 (1H, m), 3.54-3.64 (7H, m), 3.96-4.03 (1H, m), 4.15-4.20 (1H, m), 4.68 (1H, dd, J = 1.2 Hz, 10.2 Hz), 6.71 (1H, s), 6.90 (1H, d, J = 7.2 Hz), 7.26 (1H, d, J = 7.2 Hz), 7.33 (1H, d, J = 1.2 Hz), 7.78 (2H, d, J = 4.2 Hz), 8.00 (1H, br.s), 8.72 (2H, d, J = 4.2 Hz) (CDCl$_3$) | 404 |
| 263 | 3.08-3.13 (1H, m), 3.28-3.32 (1H, m), 3.52-3.62 (7H, m), 3.96-4.02 (1H, m), 4.16-4.20 (1H, m), 4.69 (1H, dd, J = 1.2 Hz, 10.2 Hz), 6.89 (1H, d, J = 7.2 Hz), 7.25-7.35 (3H, m), 7.84 (1H, br), 8.12 (1H, dd, | 405 |

TABLE 4-continued

| Compound No. | ¹H-NMR δ: | LC-MS (M + 1) |
|---|---|---|
| | J = 1.2 Hz, 4.2 Hz), 8.86 (1H, d, J = 4.2 Hz), 9.28 (1H, d, J = 1.2 Hz) (CDCl₃) | |
| 264 | 3.10 (1H, dd, J = 10.6 Hz, 12.8 Hz), 3.29 (1H, td, J = 12.1 Hz, 2.5 Hz), 3.52-3.66 (2H, m), 3.60 (3H, s), 4.03 (1H, td, J = 11.7 Hz, 7.2 Hz), 4.20 (1H, d, J = 11.6 Hz), 4.48 (2H, s), 4.73 (1H, dd, J = 10.5 Hz, 2.1 Hz), 7.34 (2H, d, J = 6.4 Hz), 7.36 (1H, br.s), 7.45 (2H, d, J = 5.6 Hz), 8.13 (1H, d, J = 5.6 Hz), 8.88 (1H, d, J = 5.2 Hz), 9.28 (1H, d, J = 1.3 Hz) (CDCl₃) | 477 |
| 265 | 3.12 (1H, dd, J = 10.5 Hz, 12.9 Hz), 3.33 (1H, m), 3.57-3.69 (2H, m), 3.58 (3H, s), 4.00 (1H, td, J = 11.7 Hz, 2.4 Hz), 4.19 (1H, dd, J = 11.7 Hz, 2.1 Hz), 4.48 (2H, s), 4.73 (1H, dd, J = 10.8 Hz, 2.4 Hz), 6.72 (1H, s), 7.34 (2H, d, J = 6.3 Hz), 7.42 (2H, d, J = 6.3 Hz), 7.85 (2H, d, J = 6.0 Hz), 8.66 (2H, d, J = 6.3 Hz) (CDCl₃) | 476 |
| 266 | 3.03 (3H, s), 3.10 (1H, dd, J = 13.2 Hz, 10.5 Hz), 3.24 (1H, m), 3.53-3.57 (1H, m), 3.58 (3H, s), 3.66-3.71 (1H, m), 4.00 (1H, m), 4.15-4.19 (1H, m), 4.75 (1H, dd, J = 10.5 Hz, 2.1 Hz), 6.71 (1H, s), 6.92 (1H, s), 7.20-7.42 (4H, m), 7.80 (2H, dd, J = 4.5 Hz, 1.5 Hz), 8.72 (2H, dd, J = 4.8 Hz, 1.5 Hz). (CDCl₃) | 442 |
| 267 | 3.04 (3H, s), 3.10 (1H, dd, J = 12.9 Hz, 10.8 Hz), 3.23 (1H, m), 3.53-3.58 (1H, m), 3.59 (3H, s), 3.68-3.72 (1H, m), 3.99 (1H, m), 4.15-4.20 (1H, m), 4.77 (1H, dd, J = 10.2 Hz, 1.6 Hz), 7.03 (1H, s), 7.21-7.43 (5H, m), 8.15 (1H, d, J = 5.1 Hz), 8.89 (1H, d, J = 5.4 Hz), 9.27 (1H, s) (CDCl₃) | 443 |
| 268 | 2.73 (6H, s), 3.11 (1H, dd, J = 10.6 Hz, 12.9 Hz), 3.35 (1H, td, J = 12.6 Hz, 3.3 Hz), 3.55-3.41 (2H, m), 3.61 (3H, s), 4.03 (1H, td, J = 11.7 Hz, 2.1 Hz), 4.20 (1H, dd, J = 11.4 Hz, 2.1 Hz), 4.83 (1H, dd, J = 10.5 Hz, 1.8 Hz), 6.72 (1H, s), 7.61 (2H, d, J = 8.4 Hz), 7.81-7.84 (4H, m), 8.81 (2H, m) (CDCl₃) | 456 |
| 269 | 2.73 (6H, s), 3.11 (1H, dd, J = 10.6 Hz, 12.9 Hz), 3.35 (1H, td, J = 12.6 Hz, 3.3 Hz), 3.55-3.41 (2H, m), 3.61 (3H, s), 4.03 (1H, td, J = 11.7 Hz, 2.1 Hz), 4.20 (1H, dd, J = 11.4 Hz, 2.1 Hz), 4.83 (1H, dd, J = 10.5 Hz, 1.8 Hz), 7.36 (1H, s), 7.62 (2H, d, J = 8.4 Hz), 7.83 (2H, d, J = 8.4 Hz), 8.12 (1H, d, J = 1.2 Hz), 8.88 (1H, d, J = 5.1 Hz), 9.29 (1H, d, J = 1.2 Hz) (CDCl₃). | 457 |
| 270 | 0.68 (1H, m), 1.15 (3H, d, J = 3.4 Hz), 1.25 (2H, m), 1.44 (1H, m), 3.09 (1H, t, J = 11.7 Hz), 3.29 (1H, t, J = 11.1 Hz), 3.52-3.64 (2H, m), 3.57 (3H, s), 3.98 (1H, dd, J = 10.4 Hz, 11.0 Hz), 4.16 (1H, d, J = 11.3 Hz), 4.69 (1H, d, J = 9.9 Hz), 6.70 (1H, s), 7.35 (2H, d, J = 8.1 Hz), 7.55 (2H, d, J = 7.4 Hz), 7.63 (1H, br.s), 7.79 (2H, d, J = 4.9 Hz), 8.71 (2H, d, J = 4.9 Hz) (CDCl₃) | 446 |
| 271 | 0.69 (1H, m), 1.14 (3H, d, J = 3.4 Hz), 1.25 (2H, m), 1.44 (1H, m), 3.09 (1H, t, J = 11.7 Hz), 3.29 (1H, t, J = 11.1 Hz), 3.52-3.64 (2H, m), 3.57 (3H, s), 3.98 (1H, dd, J = 10.4 Hz, 11.0 Hz), 4.16 (1H, d, J = 11.3 Hz), 4.69 (1H, d, J = 9.9 Hz), 7.27 (1H, s), 7.36 (2H, d, J = 7.5 Hz), 7.55 (1H, br.s), 7.56 (2H, d, J = 7.5 Hz), 8.14 (1H, d, J = 4.7 Hz), 8.86 (1H, d, J = 5.0 Hz), 9.27 (1H, s) (CDCl₃). | 447 |
| 272 | 1.61-1.94 (8H, m), 2.69 (1H, t, J = 8.1 Hz), 3.09 (1H, dd, J = 10.8 Hz, 12.8 Hz), 3.25 (1H, td, J = 3.0 Hz, 12.0 Hz), 3.52-3.64 (2H, m), 3.57 (3H, s), 3.98 (1H, td, J = 12.0 Hz, 2.1 Hz), 4.15 (1H, dd, J = 12.0 Hz, 1.5 Hz), 4.70 (1H, dd, J = 10.8 Hz, 2.1 Hz), 6.70 (1H, s), 7.32 (1H, br.s), 7.35 (2H, d, J = 8.4 Hz), 7.56 (2H, d, J = 8.4 Hz), 7.78 (2H, d, J = 4.8 Hz), 8.71 (2H, d, J = 4.8 Hz) (CDCl₃) | 460 |
| 273 | 1.61-1.95 (8H, m), 2.69 (1H, t, J = 8.1 Hz), 3.09 (1H, dd, J = 10.8 Hz, 12.8 Hz), 3.25 (1H, td, J = 3.0 Hz, 12.0 Hz), 3.51-3.63 (2H, m), 3.58 (3H, s), 3.99 (1H, td, J = 12.0 Hz, 2.1 Hz), 4.16 (1H, dd, J = 12.0 Hz, 1.5 Hz), 4.70 (1H, dd, J = 10.8 Hz, 2.1 Hz), 7.27 (1H, s), 7.31 (1H, br.s), 7.36 (2H, d, J = 8.4 Hz), 7.57 (2H, d, J = 8.4 Hz), 8.14 (1H, dd, J = 5.4 Hz, 1.5 Hz), 8.86 (1H, d, J = 5.1 Hz), 9.27 (1H, d, J = 1.2 Hz) (CDCl₃) | 461 |
| 274 | 0.69 (2H, m), 1.32 (2H, m), 1.72 (3H, s), 3.09 (1H, dd, J = 10.8 Hz, 13.4 Hz), 3.30 (1H, td, J = 7.0 Hz, 12.0 Hz), 3.52-3.64 (2H, m), 3.57 (3H, s), 4.01 (1H, td, J = 11.4 Hz, 2.1 Hz), 4.15 (1H, d, J = 12.0 Hz), 4.69 (1H, d, J = 9.48 Hz), 6.70 (1H, s), 7.37 (2H, d, J = 8.4 Hz), 7.53 (1H, br.s), 7.55 (2H, d, J = 8.4 Hz), 7.79 (2H, d, J = 4.5 Hz), 8.71 (2H, dd, J = 4.5 Hz, 1.5 Hz) (CDCl₃) | 446 |
| 275 | 0.69 (2H, m), 1.32 (2H, m), 1.49 (3H, s), 3.09 (1H, dd, J = 10.8 Hz, 1.2.8 Hz), 3.27 (1H, td, J = 7.0 Hz, 12.0 Hz), 3.51-3.62 (2H, m), 3.55 (3H, s), 4.02 (1H, td, J = 12.5 Hz, 2.3 Hz), 4.17 (1H, dd, J = 12.0 Hz, 1.9 Hz), 4.70 (1H, dd, J = 10.5 Hz, 2.1 Hz), 7.35 (1H, s), 7.37 (2H, d, J = 6.7 Hz), 7.51 (1H, br.s), 7.54 (2H, d, J = 6.7 Hz), 8.14 (1H, dd, J = 5.4 Hz, 1.5 Hz), 8.86 (1H, d, J = 5.1 Hz), 9.27 (1H, d, J = 1.1 Hz) (CDCl₃) | 447 |
| 276 | 1.56 (6H, s), 3.03 (1H, br.s), 3.10 (1H, dd, J = 10.7 Hz, 13.0 Hz), 3.30 (1H, td, J = 2.9 Hz, 12.2 Hz), 3.53-3.65 (2H, m), 3.57 (3H, s), 3.99 (1H, td, J = 11.4 Hz, 1.9 Hz), 4.16 (1H, dd, J = 11.5 Hz, 1.8 Hz), 4.71 (1H, dd, J = 10.4 Hz, 2.0 Hz), 6.70 (1H, s), 7.38 (2H, d, J = 8.5 Hz), 7.63 (2H, d, J = 8.5 Hz), 7.80 (2H, d, J = 5.9 Hz), 8.70 (2H, d, J = 6.2 Hz), 8.80 (1H, br.s) (CDCl₃) | 450 |

TABLE 4-continued

| Compound No. | ¹H-NMR δ: | LC-MS (M + 1) |
|---|---|---|
| 277 | 1.57 (6H, s), 2.16 (1H, br.s), 3.10 (1H, dd, J = 10.7 Hz, 13.0 Hz), 3.30 (1H, td, J = 2.9 Hz, 12.2 Hz), 3.52-3.64 (2H, m), 3.59 (3H, s), 4.00 (1H, td, J = 11.4 Hz, 1.9 Hz), 4.16 (1H, dd, J = 11.5 Hz, 1.8 Hz), 4.71 (1H, dd, J = 10.4 Hz, 2.0 Hz), 7.25 (1H, s), 7.39 (2H, d, J = 8.4 Hz), 7.63 (2H, d, J = 8.4 Hz), 8.14 (1H, d, J = 5.4 Hz), 8.75 (1H, br.s), 8.86 (1H, d, J = 5.1 Hz), 9.27 (1H, d, J = 1.2 Hz) (CDCl₃) | 451 |
| 278 | 2.97-3.04 (1H, m), 3.20-3.25 (1H, m), 3.33 (1H, br.s), 3.48 (3H, s), 3.70-3.82 (2H, m), 3.86-3.94 (1H, m), 4.07-4.11 (1H, m), 4.86 (1H, dd, J = 1.2 Hz, 10.2 Hz), 7.02 (1H, s), 7.58 (2H, d, J = 6.8 Hz), 7.97 (2H, d, J = 6.8 Hz), 8.20 (1H, dd, J = 1.2 Hz, 4.2 Hz), 8.99 (1H, d, J = 4.2 Hz), 9.29 (1H, d, J = 1.2 Hz) (CDCl₃) | 394 |
| 279 | 1.45 (3H, s), 1.47 (3H, s), 3.08-3.37 (3H, m), 3.19 (3H, s), 3.48 (3H, s), 3.58-3.67 (2H, m), 3.58 (3H, s), 4.00 (1H, td, J = 11.5 Hz, 1.8 Hz), 4.76 (1H, dd, J = 10.5 Hz, 2.1 Hz), 6.70 (1H, s), 7.24 (2H, d, J = 8.3 Hz), 7.43 (2H, d, J = 8.3 Hz), 7.80 (2H, d, J = 6.1 Hz), 8.72 (2H, d, J = 6.1 Hz) (CDCl₃) | 478 |
| 280 | 1.45 (3H, s), 1.47 (3H, s), 3.08-3.37 (4H, m), 3.20 (3H, s), 3.38 (3H, s), 3.59 (3H, s), 4.01 (1H, t, J = 11.5 Hz), 4.20 (1H, d, J = 11.8 Hz), 4.75 (1H, d, J = 10.6 Hz), 7.25 (2H, d, J = 7.9 Hz), 7.36 (1H, s), 7.44 (2H, d, J = 7.8 Hz), 8.15 (1H, d, J = 5.1 Hz), 8.88 (1H, d, J = 4.8 Hz), 9.27 (1H, s) (CDCl₃) | 479 |
| 281 | 1.20 (6H, s), 3.11 (1H, dd, J = 10.5 Hz, 12.9 Hz), 3.30-3.37 (1H, m), 3.32 (3H, s), 3.54 (1H, m), 3.60 (3H, s), 3.71 (1H, d, J = 12.9 Hz), 4.01 (1H, td, J = 11.7 Hz, 2.1 Hz), 4.20 (1H, dd, J = 11.8 Hz, 2.1 Hz), 4.37 (1H, br.s), 4.80 (1H, dd, J = 10.2 Hz, 1.8 Hz), 6.71 (1H, s), 7.29 (2H, d, J = 8.4 Hz), 7.49 (2H, d, J = 8.4 Hz), 7.79 (2H, d, J = 6.0 Hz), 8.73 (2H, d, J = 6.0 Hz) (CDCl₃) | 464 |
| 282 | 1.21 (6H, s), 3.11 (1H, dd, J = 10.5 Hz, 12.9 Hz), 3.30-3.37 (1H, m), 3.32 (3H, s), 3.50 (1H, m), 3.60 (3H, s), 3.71 (1H, d, J = 12.9 Hz), 4.01 (1H, td, J = 11.7 Hz, 2.4 Hz), 4.20 (1H, dd, J = 11.8 Hz, 2.1 Hz), 4.37 (1H, br.s), 4.80 (1H, dd, J = 10.2 Hz, 1.8 Hz), 7.25 (2H, d, J = 8.1 Hz), 7.31 (1H, s), 7.49 (2H, d, J = 8.1 Hz), 8.13 (1H, d, J = 5.0 Hz), 8.88 (1H, d, J = 5.1 Hz), 9.28 (1H, s) (CDCl₃) | 465 |
| 283 | 0.84-0.88 (2H, m), 1.09-1.12 (2H, m), 1.52 (1H, m), 3.10 (1H, dd, J = 12.9 Hz, 10.5 Hz), 3.27-3.46 (1H, m), 3.52-3.56 (1H, m), 3.57 (3H, s), 3.69 (1H, dd, J = 12.9 Hz, 1.8 Hz), 3.97 (1H, m), 4.15-4.18 (1H, m), 4.74 (1H, dd, J = 10.5 Hz, 2.1 Hz), 6.70 (1H, s), 7.13 (1H, m), 7.33-7.37 (2H, m), 7.57 (1H, s), 7.80 (2H, dd, J = 4.5, 1.5 Hz), 7.81 (1H, s), 8.72 (2H, dd, J = 4.5 Hz, 1.5 Hz) (CDCl₃) | 432 |
| 284 | 0.86-0.91 (2H, m), 1.08-1.12 (2H, m), 1.50 (1H, m), 3.11 (1H, dd, J = 13.2 Hz, 10.8 Hz), 3.31 (1H, m), 3.50-3.54 (1H, m), 3.58 (3H, s), 3.70 (1H, m), 3.96 (1H, m), 4.17 (1H, dd, J = 11.7 Hz, 2.4 Hz), 4.76 (1H, dd, J = 10.5 Hz, 2.1 Hz), 7.15 (1H, m), 7.31-7.40 (4H, m), 7.85 (1H, s), 8.17 (1H, dd, J = 6.0 Hz, 1.2 Hz), 8.90 (1H, d, J = 5.4 Hz), 9.28 (1H, s) (CDCl₃) | 433 |
| 285 | 0.82-0.86 (2H, m), 1.07-1.10 (2H, m), 1.52 (1H, m), 2.81 (1H, dd, J = 12.3 Hz, 10.2 Hz), 3.31 (1H, m), 3.54-3.58 (1H, m), 3.61 (3H, s), 3.80-3.83 (1H, m), 3.84 (3H, s), 4.00 (1H, m), 4.18 (1H, m), 5.05 (1H, d, J = 8.1 Hz), 6.69 (1H, s), 6.85 (1H, d, J = 8.7 Hz), 7.32 (1H, m), 7.53-7.57 (2H, m), 7.82 (2H, dd, J = 4.5, 1.5 Hz), 8.72 (2H, dd, J = 4.5, 1.5 Hz) (CDCl₃) | 462 |
| 286 | 0.83-0.86 (2H, m), 1.07-1.10 (2H, m), 1.52 (1H, m), 2.81 (1H, dd, J = 12.6 Hz, 10.2 Hz), 3.31 (1H, m), 3.52-3.57 (1H, m), 3.63 (3H, s), 3.78-3.82 (1H, m), 3.84 (3H, s), 4.00 (1H, m), 4.19 (1H, m), 5.05 (1H, d, J = 8.4 Hz), 6.85 (1H, d, J = 8.7 Hz), 7.32 (1H, m), 7.34 (1H, s), 7.47-7.59 (2H, m), 8.20 (1H, d, J = 5.4 Hz), 8.87 (1H, d, J = 5.4 Hz), 9.28 (1H, d, J = 1.2 Hz) (CDCl₃) | 463 |
| 287 | 2.77 (1H, m), 2.98 (3H, s), 3.36 (1H, m), 3.54-3.59 (1H, m), 3.62 (3H, s), 3.83-3.86 (1H, m), 3.86 (3H, s), 4.03 (1H, m), 4.22 (1H, m), 5.04 (1H, d, J = 9.3 Hz), 6.44 (1H, s), 6.70 (1H, s), 6.89 (1H, d, J = 8.7 Hz), 7.30-7.39 (1H, m), 7.32 (1H, m), 7.82 (2H, d, J = 5.1 Hz), 8.71 (2H, d, J = 5.1 Hz) (CDCl₃) | 472 |
| 288 | 2.76 (1H, dd, J = 12.9 Hz, 10.5 Hz), 2.98 (3H, s), 3.34 (1H, ddd, J = 12.6 Hz, 12.6 Hz, 3.0 Hz), 3.53-3.57 (1H, m), 3.63 (3H, s), 3.81-3.85 (1H, m), 3.87 (3H, s), 4.00 (1H, ddd, J = 11.7 Hz, 11.7 Hz, 2.4 Hz), 4.22 (1H, dd, J = 11.7 Hz, 2.1 Hz), 5.04 (1H, dd, J = 10.2 Hz, 1.8 Hz), 6.32 (1H, s), 6.90 (1H, d, J = 8.7 Hz), 7.26-7.29 (1H, m), 7.35 (1H, s), 7.40 (1H, d, J = 2.7 Hz), 8.19 (1H, d, J = 2.7 Hz), 8.87 (1H, d, J = 2.4 Hz), 9.28 (1H, d, J = 0.9 Hz) (CDCl₃) | 473 |
| 289 | 2.90-3.00 (1H, m), 3.15-3.20 (1H, m), 3.45 (3H, s), 3.65-3.71 (2H, m), 3.84-3.91 (1H, m), 4.03-4.07 (1H, m), 4.57 (2H, s), 4.68 (1H, dd, J = 1.2 Hz, 10.2 Hz), 6.84 (1H, s), 6.93-7.01 (3H, m), 7.97 (2H, d, J = 4.2 Hz), 8.70 (2H, d, J = 4.2 Hz), 10.75 (1H, br.s) (CDCl₃) | 420 |
| 290 | 2.92-3.00 (1H, m), 3.13-3.20 (1H, m), 3.47 (3H, s), 3.67-3.74 (2H, m), 3.85-3.92 (1H, m), 4.03-4.07 (1H, m), 4.56 (2H, s), 4.68 (1H, dd, J = 1.2 Hz, 10.2 Hz), 6.94-7.02 (4H, m), 8.20 (1H, dd, J = 1.2 Hz, 4.2 Hz), | 421 |

TABLE 4-continued

| Compound No. | $^1$H-NMR δ: | LC-MS (M + 1) |
|---|---|---|
|  | 9.00 (1H, d, J = 4.2 Hz), 9.30 (1H, d, J = 1.2 Hz), 10.75 (1H, br.s) (CDCl$_3$) |  |
| 291 | 1.22-1.62 (2H, m), 1.44-1.46 (2H, m), 3.10 (1H, dd, J = 10.7 Hz, 13.0 Hz), 3.30 (1H, td, J = 2.9 Hz, 12.2 Hz), 3.51-3.63 (2H, m), 3.58 (3H, s), 4.00 (1H, td, J = 11.4 Hz, 1.9 Hz), 4.16 (1H, dd, J = 11.5 Hz, 1.8 Hz), 4.27 (1H, br.s), 4.71 (1H, dd, J = 10.4 Hz, 2.0 Hz), 7.27 (1H, s), 7.39 (2H, d, J = 8.5 Hz), 7.62 (2H, d, J = 8.5 Hz), 8.14 (1H, d, J = 5.4 Hz), 8.84 (1H, br.s), 8.86 (1H, d, J = 5.1 Hz), 9.27 (1H, d, J = 1.2 Hz) (CDCl$_3$) | 449 |
| 292 | 1.15-1.17 (2H, m), 1.37-1.42 (2H, m), 3.10 (1H, dd, J = 10.7 Hz, 13.0 Hz), 3.30 (1H, td, J = 2.9 Hz, 12.2 Hz), 3.49 (3H, s), 3.52-3.64 (2H, m), 3.59 (3H, s), 4.00 (1H, td, J = 11.4 Hz, 1.9 Hz), 4.16 (1H, dd, J = 11.5 Hz, 1.8 Hz), 4.71 (1H, dd, J = 10.4 Hz, 2.0 Hz), 7.27 (1H, s), 7.39 (2H, d, J = 8.5 Hz), 7.62 (2H, d, J = 8.5 Hz), 8.14 (1H, d, J = 5.4 Hz), 8.51 (1H, br.s), 8.86 (1H, d, J = 5.1 Hz), 9.27 (1H, d, J = 1.2 Hz) (CDCl$_3$) | 463 |

Experiment 1: Inhibitory Activity of the Medicament of the Present Invention Against P-GS1 Phosphorylation by Bovine Cerebral TPK1

A mixture containing 100 mM MES-sodium hydroxide (pH 6.5), 1 mM magnesium acetate, 0.5 mM EGTA, 5 mM B-mercaptoethanol, 0.02% Tween 20, 10% glycerol, 12 μg/ml P-GS1, 41.7 μM [γ-$^{32}$P] ATP (68 kBq/ml), bovine cerebral TPK1 and a compound shown in Table (a final mixture contained 1.7% DMSO deriving from a solution of a test compound prepared in the presence of 10% DMSO) was used as a reaction system. The phosphorylation was started by adding ATP, and the reaction was conducted at 25° C. for 2 hours, and then stopped by adding 21% perchloric acid on ice cooling. The reaction mixture was centrifuged at 12,000 rpm for 5 minutes and adsorbed on P81 paper (Whatmann), and then the paper was washed four times with 75 mM phosphoric acid, three times with water and once with acetone. The paper was dried, and the residual radioactivity was measured using a liquid scintillation counter. The results are shown in the table below. The test compound markedly inhibited the P-GS1 phosphorylation by TPK1. The results strongly suggest that the medicaments of the present invention inhibit the TPK1 activity, thereby suppress the Aβ neurotoxicity and the PHF formation, and that the medicaments of the present invention are effective for preventive and/or therapeutic treatment of Alzheimer disease and the above-mentioned diseases.

TABLE 5

| Compound No. | IC$_{50}$ (nM) |
|---|---|
| 6 | 3.4 |
| 24 | 6.4 |
| 50 | 4.8 |
| 70 | 5.1 |
| 100 | 5.2 |
| 091 | 6.1 |
| 202 | 0.43 |
| 210 | 5.4 |
| 220 | 0.48 |
| 231 | 5.8 |
| 237 | 9.7 |

Experiment 2: Inhibitory Activity on Tau Phosphorylation in vivo

Test compound was administered to male CD-1 mice of 5-6 weeks weighing 25-35 g (Charles River Japan, inc.) at 1, 3, 10, 30 mg/kg p.o. (0.5% Tween/H$_2$O suspension) and after 1 h, mice were decapitated and cortex was promptly removed, followed by being frozen in liquid N$_2$. Cortex was directly homogenized with 2.3% SDS homogenization buffer (62.5 mM Tris-HCl, 2.3% SDS, 1 mM each of EDTA, EGTA and DTT, protease inhibitor cocktail (sigma P2714) containing 0.2 μM 4-(2-Aminoethyl)benzenesulfonyl fluoride (AEBSF), 13 μM bestatin, 1.4 μM E-64, 0.1 mM leupeptin, 30 nM aprotinin, pH 6.8) and centrifuged at 15000×g for 15 min at 4° C. Protein concentrations were determined using DC protein assay kit (BIO-RAD). Supernatants were diluted with sample buffer (62.5 mM Tris-HCl, 25% glycerol, 2% SDS, 0.01% Bromophenol Blue, pH 6.8) to adjust the protein concentrations around 0.5-2 mg/mg and then boiled for 5 min. 10 μg of samples were applied on 10% SDS-PAGE mini slab gels and transferred onto PVDF membranes. Membranes were incubated with PBS containing 5% non-fat milk for 1 h at r.t. and then probed with pS396 anti-body (BIOSOURCE) over night at 4° C. Anti-rabbit IgG HRP-conjugated anti-body (Promega) was used as secondary anti-body. Membranes were visualized by ECL kit (Amerasham Bioscience) and detected by LAS1000 (Fuji Photo Film).

FORMULATION EXAMPLE (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

INDUSTRIAL APPLICABILITY

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A compound represented by the formula (I), an optically active isomer thereof, or a pharmaceutical acceptable salt thereof;

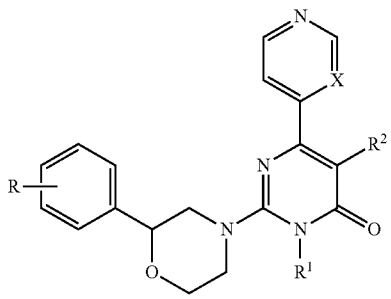

wherein each symbol is as defined below;
X represents CH or N;
$R^1$ represents a $C_1$-$C_{12}$ alkyl;
$R^2$ represents a hydrogen atom;
R represents
a formula (1);

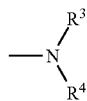

in the formula (1), $R^3$ represents a hydrogen atom, or a $C_1$-$C_6$ alkyl which may be substituted by hydroxyl or a $C_1$-$C_6$ alkoxy;
$R^4$ represents
a formula (3)

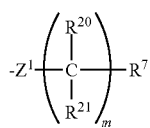

wherein m represents 0 or an integer of 1 to 4,
$Z^1$ represents a carbonyl group,
R20 and R21 are the same or different and each represents a hydrogen atom or a $C_1$-$C_6$ alkyl;

$R^7$ represents a $C_1$-$C_6$ alkyl which may be substituted by hydroxyl or halogen atom,
a $C_3$-$C_7$ cycloalkyl which may be substituted by $C_1$-$C_6$ alkyl, hydroxyl or $C_1$-$C_6$ alkoxy,
a $C_6$-$C_{10}$ aryl which may be substituted by N,N-di-$C_1$-$C_6$ alkylamino,
a heterocyclic group which may be substituted by phenyl or $C_1$-$C_6$ alkyl, or
a $C_1$-$C_6$ alkoxy which may be substituted by phenyl.

2. The compound, an optically active isomer thereof, or a pharmaceutically acceptable salt thereof according to claim 1, wherein $R^1$ is methyl group.

3. A compound according to claim 1 selected from the group consisting of:
N-(4-(4-(1-Methyl-6-oxo-4-(pyridin-4-yl)-1,6-dihydropyrimidin-2-yl)morpholin-2-yl)-phenyl)-acetamide,
N-(4-(4-(1,6-Dihydro-1-methyl-6-oxo-4,4'-bipyrimidin-2-yl)morpholin-2-yl)phenyl)-acetamide,
2-(2-(4-Cyclopropylcarbonylamino)phenyl)morpholin-4-yl)-3-methyl-6-pyridin-4-yl-3H-pyrimidin-4-one,
2-(2-(4-Cyclopropylcarbonylamino)phenyl)morpholin-4-yl)-3-methyl-6-pyrimidin-4-yl-3H-pyrimidin-4-one,
N- {4-[(2S)-4-(1-Methyl-6-oxo-4-pyridin-4-yl-1,6-dihydropyrimidin-2-yl)morpholin-2-yl]phenyl}-2-pyrrolidin-1-ylacetamide,
N- {4-[(2S)-4-(1-Methyl-6-oxo-1,6-dihydro-4,4'-bipyrimidin-2-yl)morpholin-2-yl]Phenyl}-2-pyrrolidin-1-ylacetamide,
N2,N2-Dimethyl-N1- {4-[(2S)-4-(1-methyl-6-oxo- 1,6-dihydro-4,4'-bipyrimidin-2-yl)-morpholin-2-yl]phenyl}glycinamide,
Methyl {4-[(2S)-4-(1-methyl-6-oxo-4-pyridin-4-yl-1,6-dihydropyrimidin-2-yl)-morpholin-2-yl]phenyl}carbamate,
Ethyl {4-[(2S)-4-(1-methyl-6-oxo-1,6-dihydro-4,4'-bipyrimidin-2-yl)morpholin-2-yl]-phenyl}carbamate,
N-{4-Methoxy-3-[(2S)-4-(1-methyl-6-oxo-4-pyridin-4-yl-1,6-dihydropyrimidin-2-yl)-morpholin-2-yl]phenyl}acetamide,
N-{4-Methoxy-3-[(2S)-4-(1-methyl-6-oxo-1,6-dihydro-4,4'-bipyrimidin-2-yl)morpholin-2-yl]phenyl}acetamide, and
N- { 3-[(2S)-4-(1-Methyl-6-oxo-4-pyridin-4-yl- 1,6-dihydropyrimidin-2-yl)morpholin-2-yl]phenyl}acetamide,
an optically active isomer thereof, or a pharmaceutically acceptable salt thereof.

4. A composition comprising as an active ingredient the compound represented by the formula (I) and an optically active isomer thereof, or a pharmaceutically acceptable salt thereof according to claim 1.

* * * * *